United States Patent [19]

Golias et al.

[11] 4,242,730

[45] Dec. 30, 1980

[54] SINGLE SCAN MICROPROCESSOR-CONTROLLED DENSITOMETER

[75] Inventors: Tipton Golias; Gene A. Butts; Robert A. Swift, all of Beaumont, Tex.

[73] Assignee: Helena Laboratories Corporation, Beaumont, Tex.

[21] Appl. No.: 19,041

[22] Filed: Mar. 9, 1979

[51] Int. Cl.³ ............................................. G06F 15/42
[52] U.S. Cl. .................................. 364/416; 364/417; 364/525; 364/582; 364/900; 346/33 A; 356/39; 356/432
[58] Field of Search ............... 364/416, 417, 525, 582, 364/558, 415, 900; 356/39, 432; 235/92 PC; 358/107; 346/33 A

[56] References Cited

U.S. PATENT DOCUMENTS

| | | | |
|---|---|---|---|
| 3,706,877 | 12/1972 | Clifford, Jr. et al. | 364/558 |
| 3,982,528 | 9/1976 | Phillips | 364/417 X |
| 4,005,434 | 1/1977 | Golias et al. | 364/525 X |
| 4,006,737 | 2/1977 | Cherry | 364/417 X |
| 4,124,894 | 11/1978 | Vick et al. | 364/417 |

*Primary Examiner*—Edward J. Wise
*Attorney, Agent, or Firm*—Cullen, Sloman, Cantor, Grauer, Scott & Rutherford

[57] ABSTRACT

A microprocessor-controlled densitometer system for optically scanning a blood sample or the like and generating an electric analog signal which is a function of the optical density of the scanned sample. The electrical analog signal is processed and converted into digital data for storage in a memory as raw sample data to be retained until the next given sample is scanned. Under microprocessor control, a CRT device displays a reconstructed optical density analog waveform pattern representative of the generated electrical analog signal and may be normalized for full-scale readings. While the optical density analog waveform pattern is displayed on the CRT device, the operator may visually inspect and edit the analog waveform pattern by manually positioning a cursor signal along the CRT displayed analog waveform pattern for addressing selected positions thereon and modify the analog waveform pattern by keyboard entries which add, delete, or modify fraction boundary locations, delete portions of the analog waveform pattern from computations, etc., via keyboard entries and under microprocessor control. Once the operator is satisfied with the edited analog waveform pattern and the various fraction boundaries displayed on the CRT device, a keyboard command to the microprocessor enables the displayed and edited optical density waveform pattern or any integral or selected portion thereof to be graphically recorded as an analog profile trace on a fixed record medium and may, under microprocessor control, cause a printer to print fraction identifying information and numerical data such as ratios or percentages involving the area under the analog waveform pattern or particular fractions thereof, amplitude ratios, or scaled values calculated by the microprocessor onto the record medium and preferably in a position proximate to the fraction or portion of the profile traced to which such data pertains. The method and apparatus of the present system enables the displaying and editing of the analog waveform pattern, the calculation of desired numerical data, the recording of the profile trace and the printing of the calculated data without requiring that the sample be scanned a second time and without disturbing the digital data stored in the memory which represents the originally generated electrical analog waveform since the reconstruction of the display, the editing, and the numerical calculations are done under microprocessor control using only stored data and operator-entered keyboard commands.

30 Claims, 42 Drawing Figures

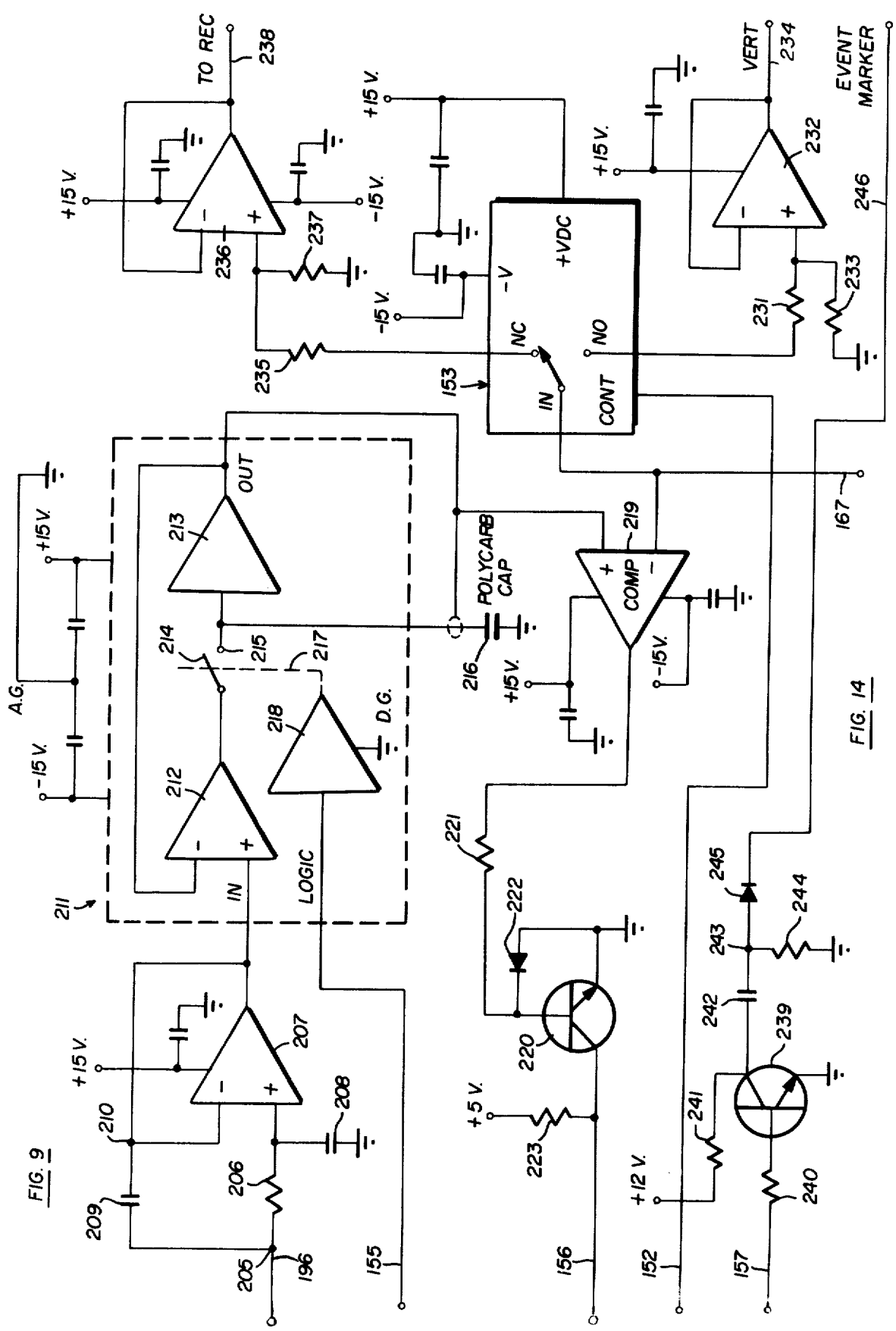

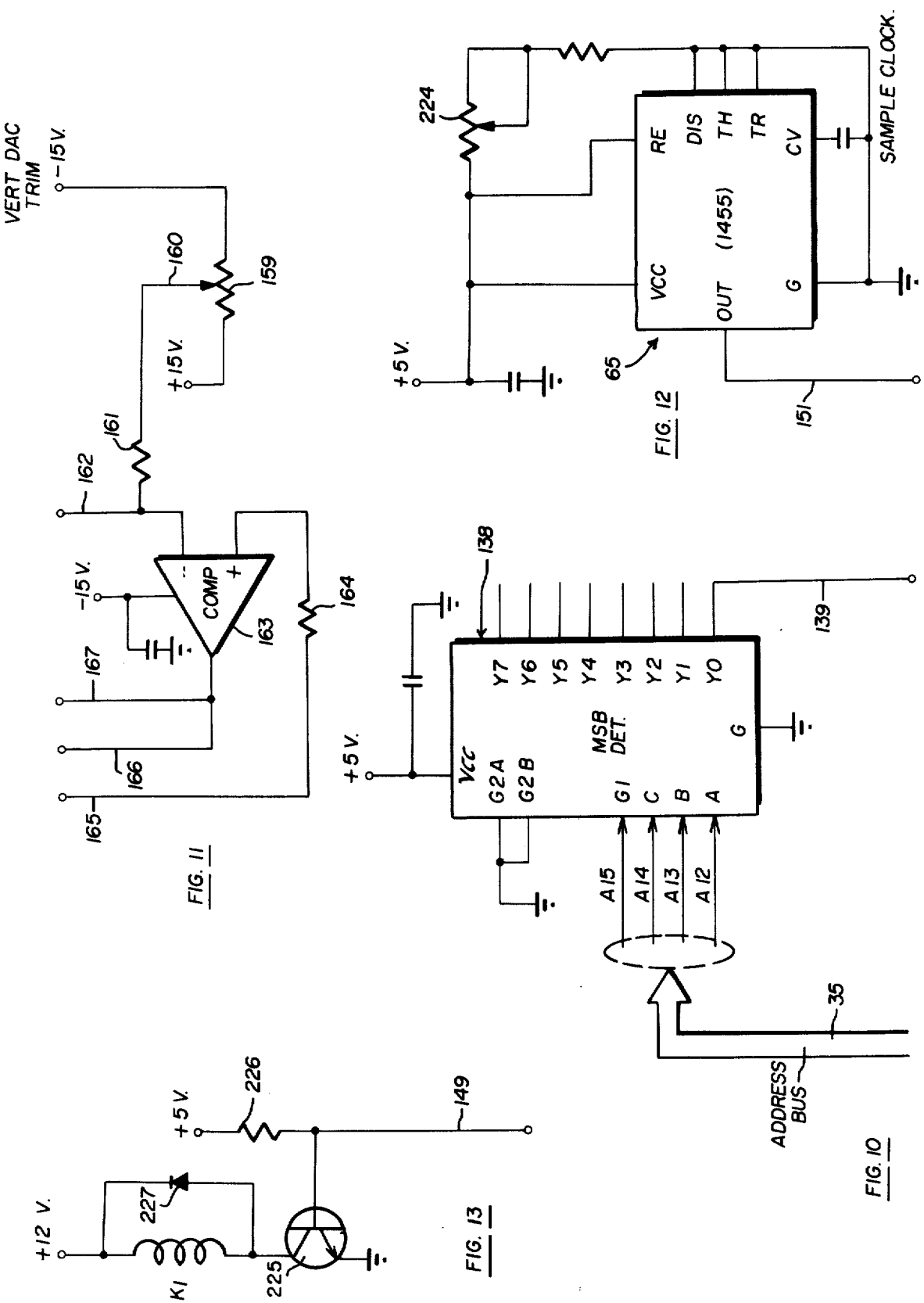

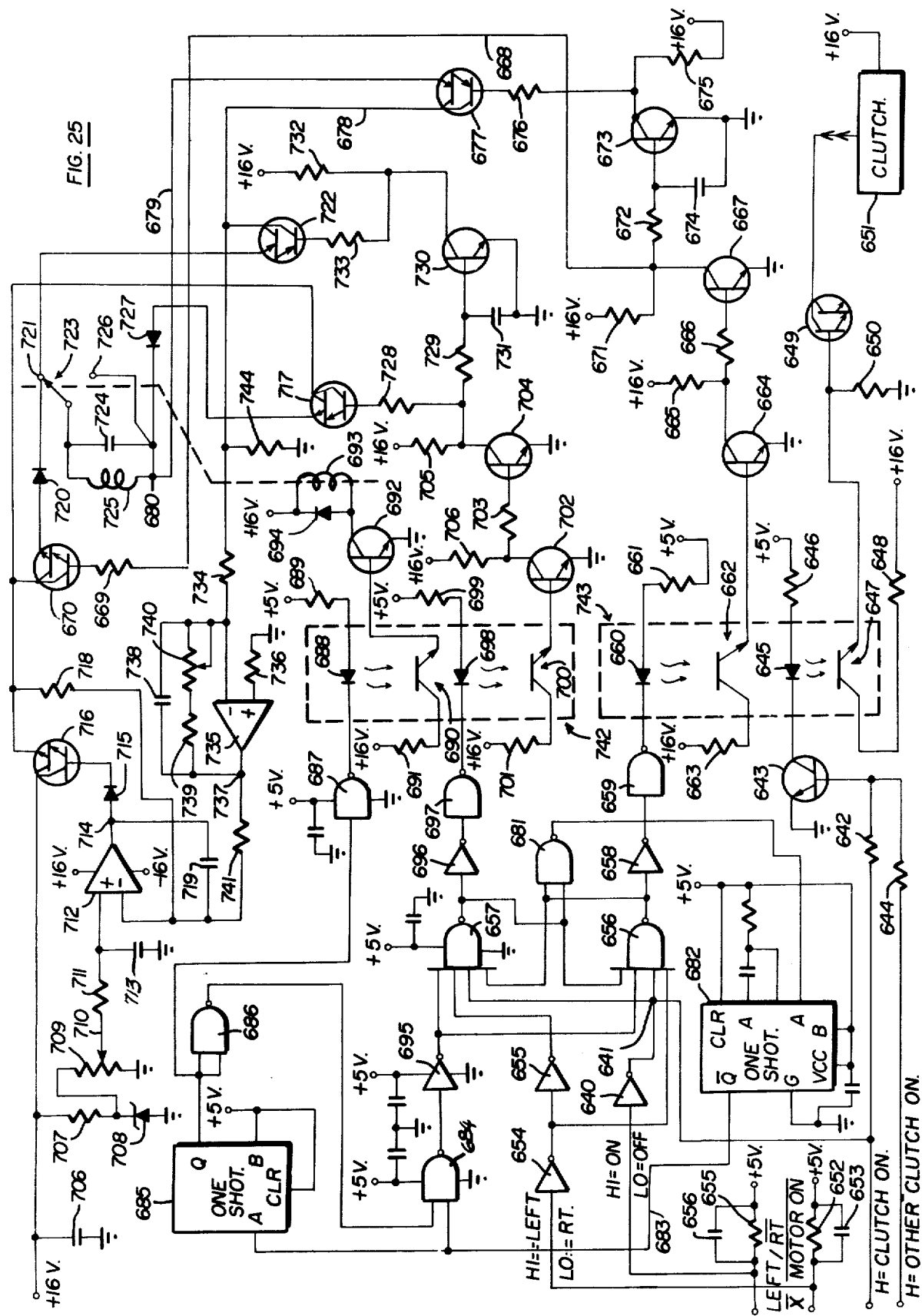

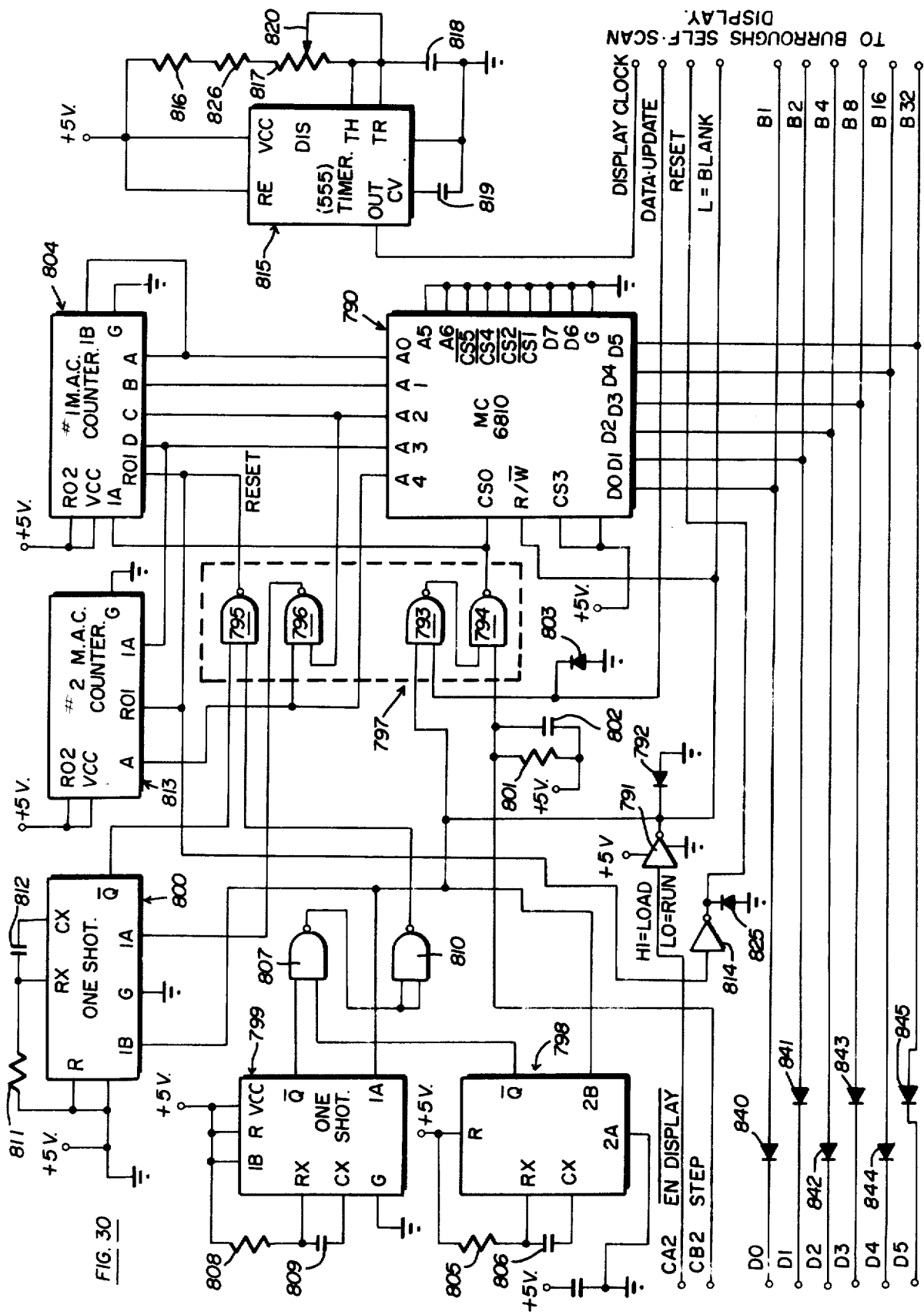

SINGLE SCAN MICROPROCESSOR-CONTROLLED DENSITOMETER

BACKGROUND OF THE INVENTION

1. Field of the Invention

This invention relates generally to densitometers and, more particularly, to an improved method and apparatus for graphically displaying densitometer output information under microprocessor control so as to eliminate the need for optically scanning the sample to be analyzed a second time.

2. Statement of the Prior Art

Densitometers are well-known as devices which scan a sample and provide an output signal or graphical display indicative of the optical density, transmittance, absorption or the like of the scanned sample.

One well-known use of the densitometer is to scan a sample of blood which has been prepared by the electrophoresis process. Electrophoresis of blood samples isolates various proteins in the blood, known as albumin, alpha-1 globulin, alpha-2 globulin, beta-globulin and gamma-globulin. The electrophoresis technique separates these proteins from each other and then the sample may be processed or scanned in a densitometer. Each of the proteins exhibits a different light absorption characteristic or pattern and the light absorption patterns are graphically displayed by the densitometer to indicate the presence and quantity of each of these proteins.

In optical density analysis, the amount of light passing through the sample is an inverse logarithmic function of the optical density of the sample. Thus, if the optical density of the sample is doubled, the transmitted light is reduced by a factor of ten. The light transmitted through a sample falls on a photo-responsive element which generates electrical signals having a current proportional to the amount of transmitted light. The current output of the photo-responsive element is, therefore, also a logarithmic function of the optical density which then is converted into analog or time-varying signals directly proportional to the optical density pattern of the scan sample. The analog signals drive a graphic display unit to provide a permanent curve or record of the optical density pattern. All this is well-known.

In addition to scanning densitometry which measures the emergent radiation passing through a sample as a measure of the sample's density either by transmittance or absorbance measurements, fluorescent densitometry is gaining wide acceptance in clinical laboratories. Some materials, when excited by energy of a short wavelength, re-emit light of a longer wavelength. The procedures presently used in laboratories fluoresce efficiently when excited by light at 366nm. The ultraviolet energy is used only to excite the fluorescent material and, unlike transmission densitometry, is not the light used for quantitation. The only light detected and measured in fluorescent densitometry is the light emitted by the sample and the relationship between the emitted light of the sample and its concentration is linear rather than logarithmic as it is with transmission densitometry. Hence, with fluorescent techniques, a linear rather than a logarithmic amplifier may be used for measurement purposes.

In either case, the electrical analog signals generated by the photo-responsive elements, when graphically displayed, exhibit a series of peaks and valleys. In the analysis of blood, the area under the optical density curve and bounded by the two adjacent valleys separated by one peak, is representative of the quantity of each protein in the sample and is referred to as a sample fraction. The important data is the relative percentage of each protein and the selection of these fraction boundaries, i.e., the precise locations of these valleys is somewhat arbitrary and results in inaccurate analysis of the blood sample. The problem is not unique to evaluation of blood samples, but is common to optical and magnetic density valuations and, in fact, to all evaluations of analog data.

There are various prior art systems which have considered this problem which provide a standardized graphical display of the densitometer output. For example, U.S. Pat. Nos. 3,185,820 issued May 25, 1965 to A. P. Williams, et al; 3,553,444 issued on Jan. 5, 1971 to P. P. Tong; 3,706,877 issued Dec. 19, 1972 to G. F. Clifford, Jr., et al; 3,767,899 issued Oct. 23, 1973 to L. D. Barter; 3,784,789 issued on Jan. 8, 1974 to J. A. Vandenbroek; 3,842,422 issued Oct. 15, 1974 to J. A. Vandenbroek; 3,902,813 issued Sep. 2, 1975 to J. A. Vandenbroek, et al. and 4,005,434 issued on Jan. 25, 1977 to T. L. Golias, et al. disclose various systems for analyzing the densitometer output and for minimizing the problems involved. The densitometer output is graphically displayed as an analog signal or curve indicative of optical density and a second signal which is the integral of the optical density, i.e., the area under the optical density curve, and which may be either analog, or numerical or both. In each of these patents, various analog computational circuitry is employed.

There are three common techniques for determining the location of the fraction boundaries or valleys. In the first technique, the densitometer includes circuitry to automatically detect the valleys between the peaks based upon changes in the slope of the curve, integrate the area under the curve between valleys and print out the integral in numerical form. Then, in order to determine the percent of each protein, the operator of the equipment has to add the printed values to obtain a denominator and then calculate each percent by dividing each printed value by the calculated denominator.

Not only is this time consuming, but if, in fact, the computer system erroneously selected a particular boundary location, the results are useless to the physician evaluating the blood sample. Hence, the results of the computer print-out cannot conveniently be utilized for subsequent evaluation if the physician analyzing the blood sample disagrees with the particular boundary decisions made by the computer.

A second type of system provides two graphic displays, the first being the optical density of the scanned sample and the second being the integral of the optical density pattern. These are plotted or traced on graph paper and at a later time, the physician can select the particular boundaries for each protein. Then the area under the curve is calculated by actually manually counting the number of squares under the curve between each pair of boundaries which is equivalent to the aforementioned printed values. Again, the percentage of each protein is then calculated by the addition and division procedure explained previously. Again, however, this requires laborious manual counting as well as manual calculations resulting in lost time and increasing the potential for error.

Finally, the third type of system provides both of these techniques together, i.e., a numerical print-out and a curve so that the boundaries may be manually selected if the position is not satisfied with the automatically selected boundaries. However, this still does not eliminate the manual counting and addition-division procedure for obtaining percentages of each protein.

Therefore, a fourth technique has been devised as illustrated in the more recent of the above-identified patents whereby the densitometer output is graphically displayed as an analog signal or curve indicative of optical density and the computer-selected fraction boundaries are displayed as well. The operator is then allowed to inspect and edit the curve and he may add, delete or modify boundary decisions so that a second scan of the same sample will provide more accurate information. Furthermore, techniques have been developed to obtain maximum utilization of the optical density curve by determining the maximum optical density or maximum peak value of a particular sample during a first scan and then adjusting the values of the optical density curve so that the maximum value comes as near to a full scale reading as possible and is assigned a value of unity for normalizing the graphic display without distortion and thereby providing more pronounced valleys or fraction boundaries.

Additionally, systems have been evolved which normalize not only the optical density curve but also normalize the integral of the optical density pattern once the technician or physician operating the system has satisfied himself as to the location of each fraction boundary for each protein thereby eliminating the aforementioned addition, division steps and allowing direct computer evaluation.

Several of the systems of the prior art employ analog devices which utilize two separate and distinct scans of each sample with a delay between successive scans. On the first scan, the analog computer records the scanned optical density pattern by recording it on graph paper or the like and the operator is able to make all of the fraction boundary decisions based on his observation of the plotted optical density curve before he provides his information to an integrating unit which receives the electrical representations of the signal.

In such systems, the time-varying electrical input signals are provided to both the recorder and to a delay unit and the sheet of paper carrying the plot of the optical density curve is passed beneath a cursor. The distance between the printer and the cursor is sufficient to give an operator time to study the curve that emerges and make decisions relative to fraction boundaries. When a point on the curve responding to a boundary, as determined by the operator, passes under the cursor, a switch is pushed providing a signal relative to the boundary and the delayed output signal is provided to an integrator in a timed relation to the passage of the curve under the cursor so that when the button is pressed the integral count is returned to zero. Simultaneously, a second marker produces an appropriate blip on the chart paper to identify the boundaries of the fractions which are being calculated.

Since operators considered this a very demanding and tiring operation and since it is highly subject to human failure due to the time pressures put on the operator as the paper passes beneath the cursor and the time lag between the operator decision to modify a boundary and the pressing of the button to effect the change, more automatic systems have been devised whereby machine decisions are conveyed to an operator to allow the operator to modify machine decisions before the integrals are actually calculated. But even in such systems, a re-scanning of the original sample or a re-scanning of the marked up or modified graph paper is required. The room for human error is still too great and the accuracy of the results is insufficient for many purposes. A fully automatic computer system which minimizes the possibility for human error, optimizes normalization and calculation accuracy and requires only a single rather than a double scan is required.

The present invention solves substantially all of the problems of the prior art in a single system by using a microprocessor-controlled densitometer system which requires only a single optical scan of the sample being analyzed and utilizes the computation capacity of a microprocessor to insure the accuracy of numerical calculations while insuring that machine-made boundary decisions are viewed on a CRT device by the operator who then edits the displayed optical density waveform pattern to add, delete or otherwise modify boundary decisions and the like prior to the actual integrations, ratio or percentage calculations, scalings, etc., and prior to the recording of the required analog profile trace on a fixed record medium and the corresponding printed information relating thereto.

SUMMARY OF THE INVENTION

One embodiment of the present invention contemplates a method of graphically displaying optical density patterns of a sample of blood or the like for subsequent evaluation. The method includes the steps of optically scanning a sample a single time to generate an electrical analog waveform which is a function of the optical density of the scanned sample. The electrical analog waveform is then converted into a set of digital signals which are stored in a memory as raw sample data. The stored raw sample data may be retrieved to reproduce or reconstruct the analog waveform which may be normalized and displayed on a CRT device for visual operator inspection without the need for rescanning the original sample. The operator may then edit the visually displayed analog waveform to selectively modify portions thereof while maintaining the raw sample data unchanged in memory. A graphical trace of the edited analog waveform may then be recorded on a fixed medium once the operator is satisfied with fraction boundary decisions and the like.

Additionally, the method contemplates that the editing operation may involve the generation of a cursor signal, the manual positioning of the cursor signal along the optical density waveform displayed on the CRT device for addressing the location of specific points thereon and the entering of keyboard commands to add, delete or otherwise modify boundary decisions addressed by the cursor position under microprocessor control and storing the values thereof for future microprocessor-controlled numerical calculations including integrations, amplitude scaling, and percentages and ratios thereof.

Likewise, the step of recording the graphical trace may include recording one or more graphical traces involving a selected one or more of the edited optical density waveform, some function of the optical density waveform, the area under the optical density curve or any given portion thereof, etc., and a digital printer may be used to print alphanumeric information including, for example, fraction identification and numerical values relating to percentages, ratios or scaled values of relative or absolute fraction values.

Yet further, the method of the present invention contemplates operation in an external mode wherein the total protein value of the scanned sample is manually entered on a keyboard for scaling purposes or in one of three different internal standard modes. In a first internal standard mode, a standard sample having a known protein value is actually scanned and the value entered into memory for future scaling purposes. In the second internal standard mode of operation, first and second known samples are scanned and the values stored in memory. The actual calculated value for the scanned samples are then compared to the stored internal standards and the more appropriate of the two is selected as the standard sample value for scaling and the like. In the third internal standard mode, the total protein information is derived from a value input directly by the user.

Additionally, a known optical density standard may be selected by the user for obtaining a print-out of fractions of optical density values in which the amplitudes of the scan patterns will be scaled to represent their optical density by amplitude. Lastly, the method of the present invention contemplates a single step method of manual scanning or auto step scanning, and either preprogrammed or user programmed being scan and end scan locations may be used.

The apparatus of the present invention contemplates a microprocessor-based densitometer for graphing the relevant optical density patterns of a blood sample or the like and includes means for optically scanning the samples and generating an electrical analog waveform pattern related to the optical density of the sample. Means for converting the electrical analog waveform pattern into digital sample data are provided as are memory means for storing the digital sample data. Means are provided for retrieving the stored digital sample data and reconstructing a normalized version of the analog waveform pattern without rescanning the sample. CRT means are used for visually displaying the reconstructed analog waveform pattern for inspection by an operator and editing means enable the operator to selectively modify portions of the waveform pattern to alter fraction boundary decisions and the like as desired. Means are provided for graphically recording the edited optical density waveform pattern or various functions or integrals thereof.

Additionally, means are provided for processing the generated electrical analog waveform pattern through a selected one of either a linear input amplifier or a logarithmic input amplifier depending upon the nature of the optical scanning means. A microprocessor-based computational system may be used for retrieving, reconstructing, and normalizing the analog waveform pattern and for controlling the CRT display means, the editing means and the recording means subject to operator-entered keyboard commands.

The editing means may include means for generating a cursor signal, means for manually positioning the cursor signal along the waveform pattern for addressing particular locations thereon and keyboard-controlled means for selectively adding, deleting or otherwise modifying portions of the waveform pattern addressed by the cursor for modifying the wave form or altering integral boundary decisions.

A printer may be provided for printing alpha numeric information onto the fixed record medium in proximity to the analog profile trace of the optical density function for identification purposes and for providing numerical data to aid in the evalution thereof. The microprocessor may be programmed to calculate any of the number of desired ratios, percentages, etc., involving the amplitude or area under the optical density curve and similar pertinent data.

The microprocessor-controlled densitometer of the present invention provides a highly accurate and reliable graphical recording of the desired optical density functions and the numerical data corresponding thereto with only a single scan of the original sample being required and without requiring the handling or rescanning of the fixed record medium. This is possible since the microprocessor enables the reconstruction of the optical density pattern and its display on a CRT or an oscilloscope-type device so that the operator can inspect and edit the displayed waveform at his leisure and make any desired adjustments to the waveform while it is still displayed on the scope including, but not limited to, adding, deleting or modifying fraction boundaries, deleting whole portions of the waveform from numerical calculations, etc.

Many other advantages and meritorious features of the present invention will be more fully understood from the following detailed description of the drawings and the preferred embodiment, the appended claims and the drawings, which are described briefly hereinbelow.

BRIEF DESCRIPTION OF THE DRAWINGS

FIG. 9 is a schematic diagram of the output end of the amplifier chain from the photomultiplier tube of FIG. 8 through the sample and hold circuit and its input to the PIA circuitry of FIG. 7;

FIG. 10 is a detailed block diagram representing a one-of-eight address decoder circuit is used to select the PIA's of FIG. 7;

FIG. 11 is a schematic diagram of the vertical DAC trim circuitry which inputs the analog signals to the I/O portion of the circuit of FIG. 7;

FIG. 12 is a detailed block diagram of the sample clock which supplies sample clock pulses to the PIA circuitry of FIG. 7 for controlling the sample rate of the analog input signal;

FIG. 13 is a schematic diagram of a relay coil activated by a command from the PIA circuitry of FIG. 7 for controlling various relay-operated switches and related circuits;

FIG. 14 is an electrical schematic diagram of the Event Marker generation circuitry which operates under the control of the PIA circuitry of FIG. 7;

FIG. 25 is an electrical schematic diagram of the motor control circuitry associated with the X-Y carriage of block 57 of FIG. 1;

FIG. 30 is a detailed block diagram of the recirculating memory portion of the display control system associated with the display of block 40 of FIG. 1;

FIG. 35 is an electrical schematic diagram of a portion of the carriage direction control circuitry associated with block 57 of FIG. 1;

DETAILED DESCRIPTION OF THE PREFERRED EMBODIMENT

Figure 1:
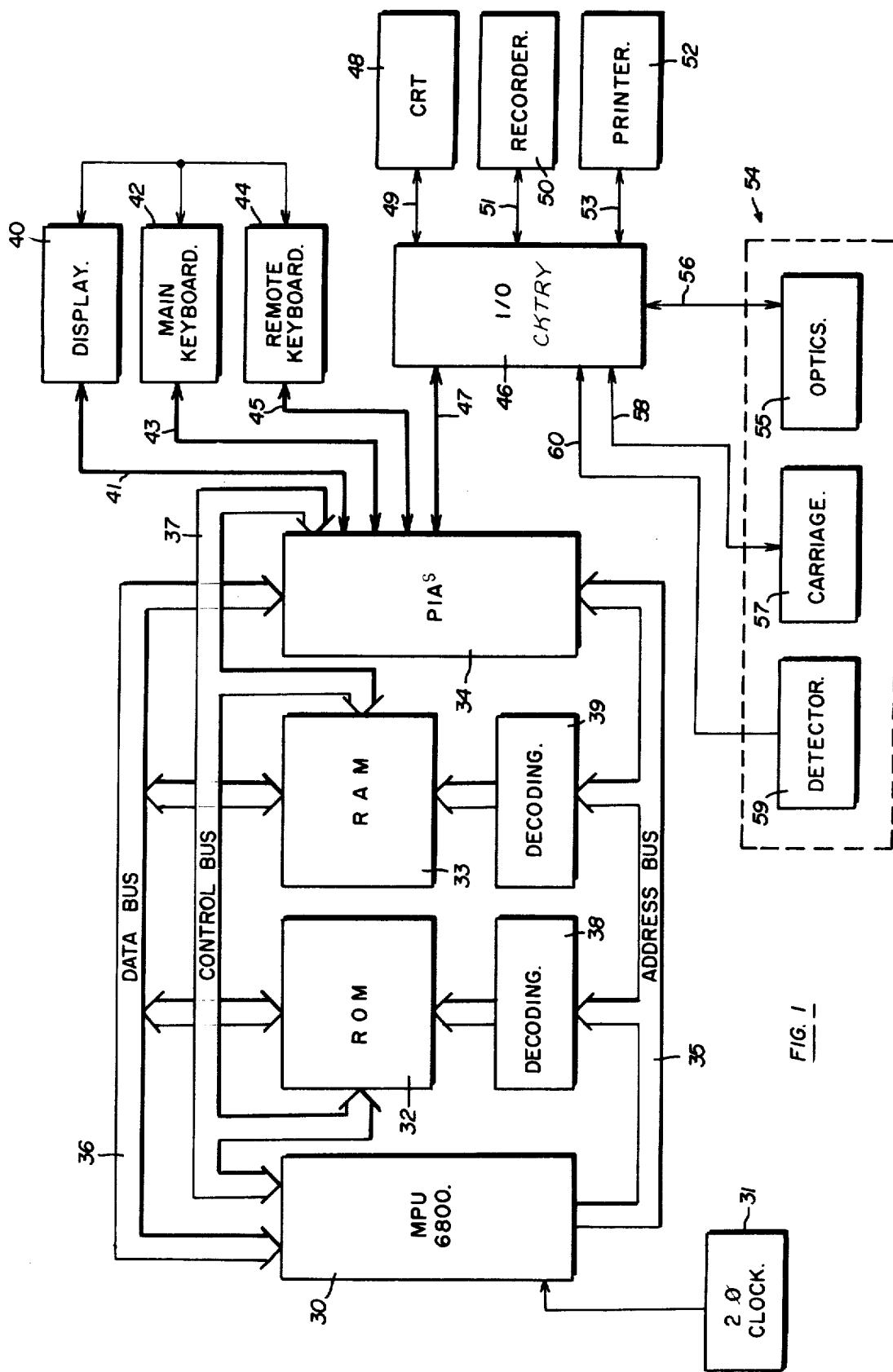
FIG. 1 is a block diagram representing the microprocessor-controlled densitometer system of the present invention.

FIG. 1 is a block diagram of the microprocessor-controlled densitometer system of the present invention. In the system of FIG. 1, the microprocessor 30 is a conventional Motorola MC6800B which is supplied with two phase clock pulses from a clock 31. The microprocessor 30 is interconnected to a Read Only Memory (ROM) 32, a Random Access Memory (RAM) 33, and Peripheral Interphase Adapters (PIAs), represented by block 34. The microprocessor 30 communicates with the ROM 32, the RAM 33 and the PIAs 34 through an address bus 35 which handles the sixteen address lines of the microprocessor as hereinafter described, a data bus 36 which handles the eight data lines of the microprocessor 30 and a control bus 37 which is used to represent the various control functions of the microprocessor 30. The address bus 35 may be supplied to an address decoding circuit 38 for chip selection and/or memory location addressing of the ROM 32 and another address decoding circuit 39 may be used to connect the address bus 35 to the RAM 33 for chip selection and/or addressing purposes as hereinafter described.

The Peripheral Interface Adapters 34 provide digital outputs for the microprocessor 30 and are used to interface with external modules. The PIA 34 may interface directly with the Self-Scan Display Panels of block 40 via communication path 41; with a main chassis keyboard 42 via communication path 43; and with a remote keyboard 44 via communication path 45. Since the display 40, the main keyboard 42 and the remote keyboard 44 utilize digital signals, they may interface directly with the PIAs 34 whereas many of the other circuits are analog in nature and require the I/O circuitry of block 46 to interface with the microprocessor 30 through the PIA 34.

The I/O block 46 is operatively coupled to the PIA 34 via communication path 47. Simultaneously, the I/O circuitry of block 46 is coupled to the cathode ray tube or oscilloscope circuitry of the CRT block 48 via communication path 49; to the recorder circuitry of block 50 through the communcation path 51; and to the digital printer 52 through the communication path 53. The I/O circuitry of block 46 is also connected to the optical scanning circuitry of dotted block 54 which includes the optical apparatus and associated control circuitry represented by block 55 which is operatively coupled to the I/O circuitry of block 46 via communication path 56; the scanning carriage and associated control circuitry of block 57 which is used to move the sample to be analyzed with respect to the optics of block 55 for scanning purposes and which is operatively coupled to the I/O circuitry of block 46 via path 58; and the optical detector and related circuitry of block 59 which supplies electrical analog signals from the photomultiplier tube of the detector 59 of the I/O circuitry of block 46 via communication path 60.

Before explaining the individual components of the system of FIG. 1 and the operation thereof, a brief overview might aid in understanding the overall system and its operation. The main controlling element of the microprocessor-controlled densitometer system of FIG. 1 is the microprocessor 30. It is, by itself, an integrated circuit capable of binary operations and a few "housekeeping" chores. Therefore, the microprocessor 30 requires various support circuits as seen in FIG. 1. Of primary importance is a program which is stored in ROM 32. This program contains the sequence of events or steps that the processor 30 must do or the operations it must execute for the system to function. It is this program that enables the processor 30 to perform the task of translating inputs to user desirable results. The program could also be stored in a RAM, off-loaded from a magnetic storage medium such as a cassette or floppy disk, or the like, as known in the art.

Since the microprocessor 30 must be able to communicate with its supporting circuits, the address bus 35, data bus 36 and control bus 37 are utilized. The other supporting circuits in addition to ROM 32 include the RAM 33 and the PIAs of block 34. The I/O circuitry of block 45 provides the processor 30 and its associated PIAs 34, which are basicly a digital system, with an interface to both external digital equipment such as the display 40, keyboards 42 and 44 and with analog devices or analog/digital devices such as the CRT 48, recorder 50, printer 52, and the optical scanning system 54.

Figure 2:
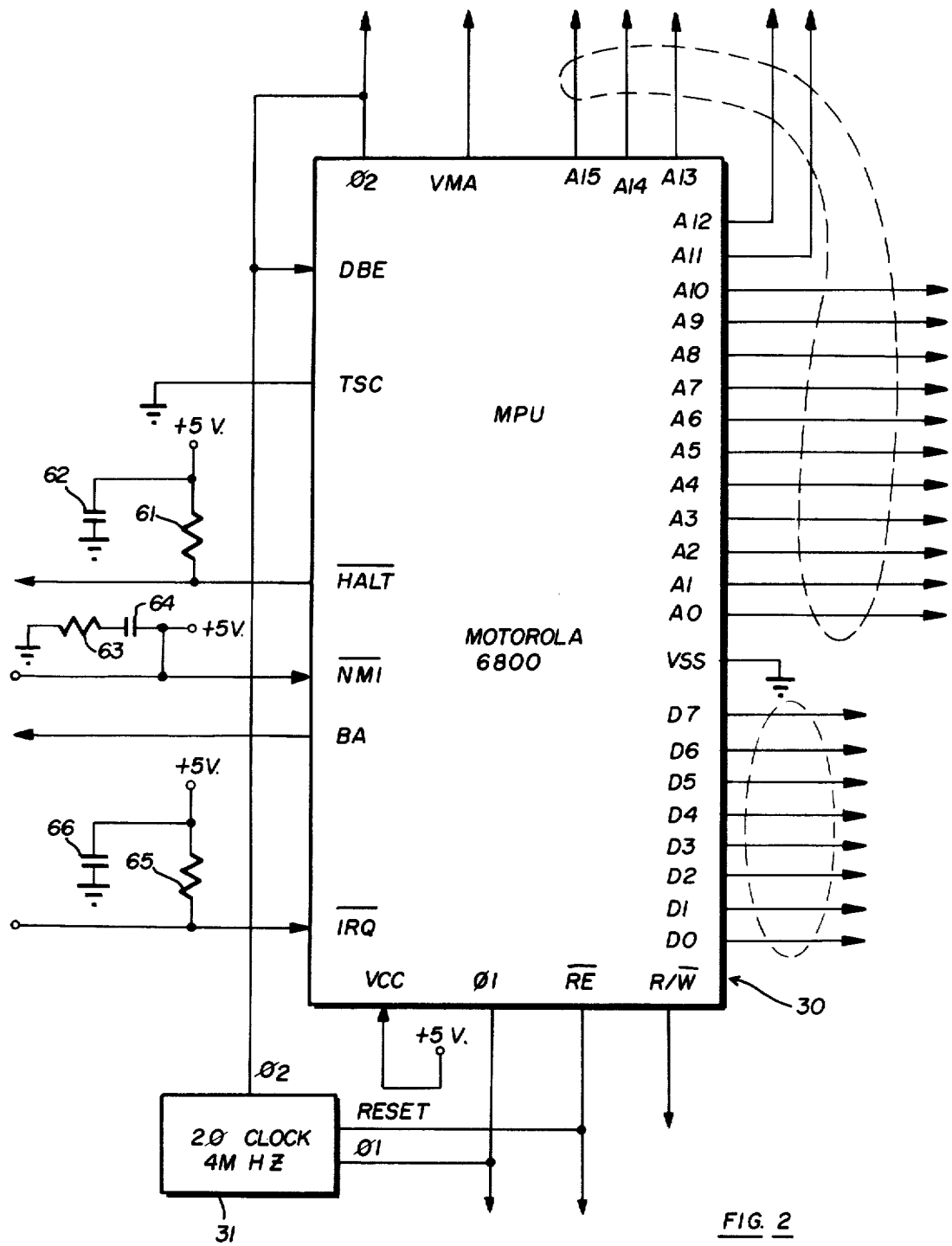
FIG. 2 illustrates, in greater detail, the microprocessor 30 of FIG. 1 and the various inputs and outputs used for addressing, data, and various control functions.

FIG. 2 illustrates the microprocessor unit 30 of the present invention and the two phase clock 31 associated therewith. As previously indicated, the microprocessor 30 is preferably a Motorola MC6800B although it will be understood that any similar microprocessor could be utilized. In fact, while the present system employs a microcomputer to control the densitometer system of the present invention, it will be understood that a complex digital circuit, a mini-computer or even a general purpose digital computer could also be utilized but cost considerations and the like heavily favor the use of the micro-computer at this time.

The inputs and outputs of the microprocessor 30 are all at TTL (5 volt logic) levels. The processor 30 has sixteen address lines designated A0 through A15 and eight data lines designated D0 through D7. Additionally, the processor 30 has a number of control lines which are collectively referred to as the control bus 37 as hereinafter described.

In operation, the microprocessor 30 will place a specific sixteen binary bit address on the address bus 35 by signals present at the sixteen address lines A0 through A15 and it may read or write an eight bit binary word to or from any associated device which responds to that address via the bi-directional data bus 36. The device responding to the particular address on the address bus 35 may be ROM 32 where the program is stored, RAM 33 where variables or data is stored, or an output interface device such as the PIAs of block 34. The point to be made is that every device connected to the address bus 35 and the data bus 36 has a specific and unique address of all of the 65,536 available memory locations on the sixteen bit address bus 35.

The $\overline{R/W}$ output of the processor 30 is referred to as the Read/Write line. It conveys to the bus devices if the processor is reading (a high signal) from a device or writing (a low signal) to a device. This $\overline{R/W}$ signal is applied to the control bus 37 through a conventional buffer circuitry. The Bus Available (BA) output signal from the processor 30 is not utilized in the present system but is made available in case future use is required. Similarly, the Halt ($\overline{HALT}$) input is tied high through a resistor 61 which connects the $\overline{HALT}$ input to a +5 source of potential to permit the processor 30 to operate but it is not otherwise used in the present system. A capacitor 62 couples the +5 volt source to digital ground. The Tri State Control for the address bus 35 (TSC) is tied low, by connecting it to ground, to keep the address bus 35 active at all times.

The processor 30 requires two separate and distinct input clock signals. These are referred to as the phase 1 signal $\phi 1$ and a phase 2 signal $\phi 2$ which are supplied to the inputs labeled $\phi 1$ and $\phi 2$ via the two phase clock of block 31 as hereinafter described. The processor 31 executes the read or write to the address location during the phase 2 clock cycles and therefore the Data Bus Enable input (DBE) is tied to the phase 2 clock input $\phi 2$ to enable the data bus outputs $D_0$ through $D_7$.

Another output from the processor 30 is labeled VMA which is an acronym for Valid Memory Address. The signal is used in conjunction with the phase 2 clock signal, the $\overline{R/W}$ and the address bus 35 in selecting various devices attached to the address bus 35. It signals those devices that the signal levels present on the sixteen address lines repesented by the address bus 35 contain a valid address which is to be responded to. There are times when the processor 30 will have an invalid set of signals on the address bus 35 resulting from internal data transfers and the like.

One of the remaining signals is the Reset input (RE). This signal originates in the two phase clock circuitry of block 31 and is generated at the power-on condition or when a MASTER RESET is initiated. The processor 30 has the requirement that the RESET input remain low for a minimum of eight machine cycles and this time duration is established by an R-C network in the clock circuitry of block 31, as conventionally known.

The two remaining inputs are interrupt inputs. The $\overline{IRQ}$ is the primary Interrupt Request Input and is most commonly used in the present system. It is tied to the MC6820 Peripheral Interphase Adapters of block 34 via the control bus 37. When one of the PIAs pulls its Interrupt Request line to a low signal level, the processor 30 will have its attention momentarily diverted from whatever it is doing to a program segment which sorts out which device pulled this line low. The processor 30 will then take any action required and return to the point in the program where it was prior to its $\overline{IRQ}$ being pulled low. At present, the interrupt-driven devices are the recorder of block 50, the printer of block 52, the oscilloscope cursor of block 48, and the X-Y axis carriage encoders and carriage limit switches of block 57.

The other interrupt input is the Non-Maskable Interrupt ($\overline{NMI}$) which is also an active low input. This input will gain control of or the attention of the processor 30 whenever it goes low. It is used in the densitometer system of the present application as a reset input for the main chassis keyboard of block 42. In some instances, however, the microprocessor 30 may fail to respond to this input, in which case the operator can utilize the Master Reset Key associated with the clock circuitry of block 31, as conventionally known. Both of the interrupt inputs, $\overline{IRQ}$ and $\overline{NMI}$ are pulled high through a resistor-capacitor pair coupled between the input and a +5 volt source of potential.

The +5 volt power is applied to the processor 30 at the VCC input, and the VSS input is connected to ground. In the present application, neither the +5 volt source of potential required for the processor 30 nor any of the other positive or negative power supplies required in the densitometer system of the present invention will be described since all of the power supply systems utilized in the present system are conventional and hence reference will be made only to the fact that a particular voltage level is applied but not to the circuitry which produced it.

The clock of block 31 is a conventional MC6875 clock chip which generates the two phase or bi-phase clock signals $\phi 1$ and $\phi 2$ required by the processor 30 and certain of the other circuits. The clock circuit of block 31 utilizes a four Megahertz crystal oscillator with the crystal by-passed by a damping capacitor to damper spurious oscillations by insuring proper loading. The first and second clock phases are supplied to the processor by the correspondingly designated processor inputs and each line to the processor has a small resistor in it (not shown) to suppress ringing and the like. The System Reset utilizes a capacitor to establish the time period which the reset signal $\overline{RE}$ is held low during the initial power on condition. A front panel switc, MASTER RESET, will also pull the $\overline{RE}$ input low through a limiting resistor to simulate a power on reset condition. Various other clock inputs which are not shown are configured to present false triggering and the like and the clock system of block 31 provides a highly accurate set of non-overlapping clock signals which are 180 degrees out-of-phase with one another.

Figure 3:
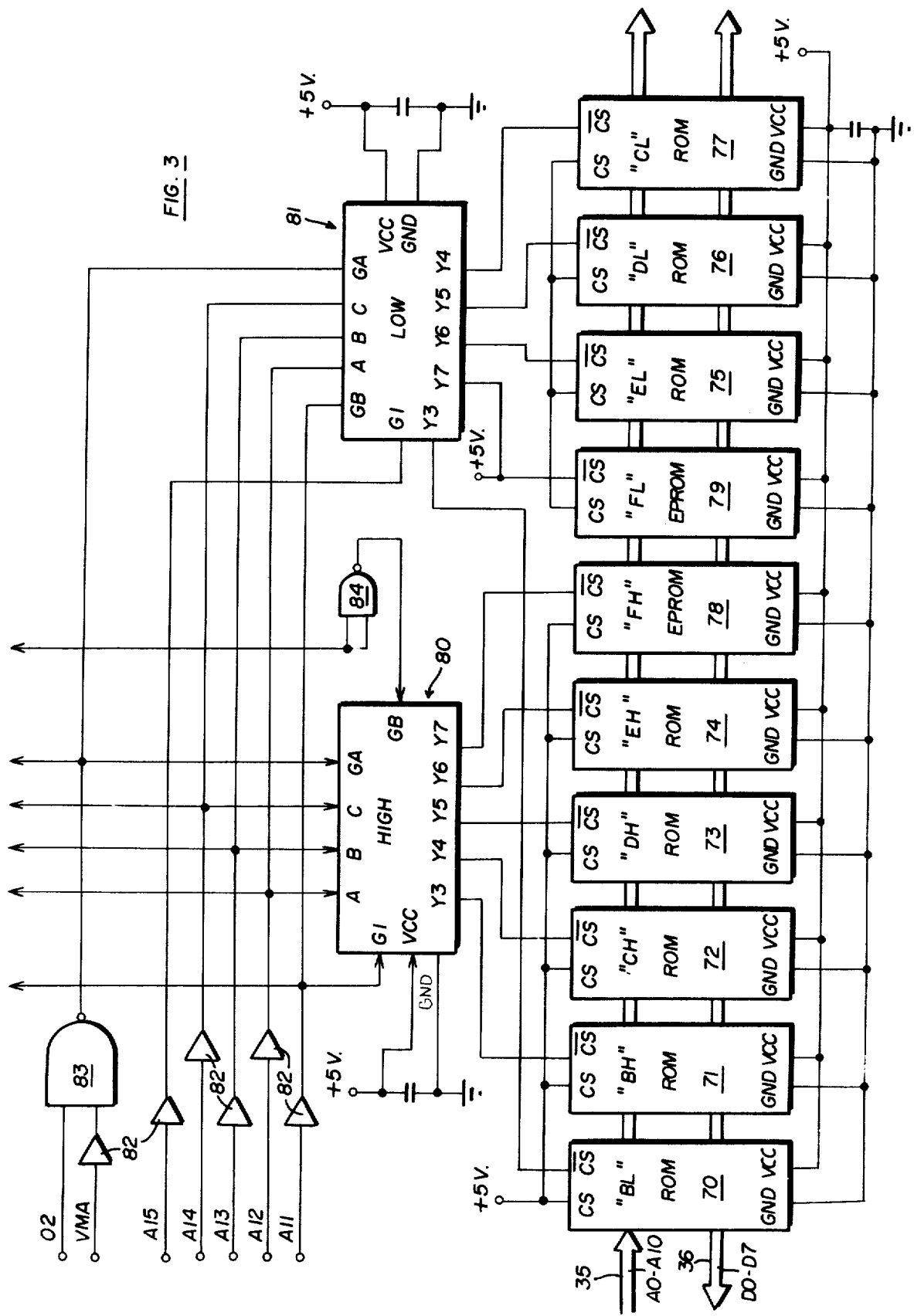
FIG. 3 is an electrical schematic diagram of the Read Only Memory of block 32 of FIG. 1.

FIG. 3 shows the address decoding circuitry of block 38 and the ROM circuitry of block 32 of FIG. 1 in more detail. In the circuit of FIG. 3, the Read Only Memory or ROM of block 32 includes eight individual Read Only Memory modules identified by reference numerals 70 through 77 and two Erasable Programmable Read Only Memories or EPROMs identified by reference numberals 78 and 79. Each of the units of ROM 70 through 77 and EPROMs 78, 79 are addressed by the first eleven address lines A0 through A10 of the address bus 35 and output the stored program data on the eight data lines D0 through D7 via the data bus 36. Each memory unit has its VCC input connected to the +5-volt source of potential and its ground input GND coupled directly to ground. As conventionally known, address buffers or drivers may be added at any point along the address bus 35, as required, and conventional data bus drivers may be added at any point along the data bus 36 to maintain proper signal levels.

To understand the address decoding accomplished by the circuitry of block 38 of FIG. 1 and, more specifically, the logic circuitry and decoders 80 and 81 of FIG. 3 which are used to perform the necessary chip select function and memory location addressing the following should be understood. All of the memory devices, ROMs 70 through 77 and EPROMs 78, 79, are used to contain some program information or some program and variables to enable restructuring of the system's capabilities, if desired. For all practical purposes, the ROMs 70-77 and EPROMs 78 and 79 are functionally equivalent and pin-for-pin compatible with one another.

To cover the address decoding four conditions must be examined. These consist of (1) a read from ROMs 70-77; (2) a read from EPROMs 78, 79; (3) a read from an address not available on the circuit of FIG. 3; and (4) a write to an address not available on the circuit of FIG. 3. The first two read functions are so similar that only the differences will be pointed out during the brief discussion which follows.

When the processor 30 requires program information from the ROMs or EPROMs of FIG. 3, the appropriate address is placed on the address bus 35. A0 is the least significant bit and A15 is most significant bit of address information. A0 through A10 are applied directly to each and every one of the ROM units 70 through 77 and the EPROM units 78 and 79 by way of conventional buffers, not shown, which drive the main address bus 35. The remaining addresses A11 through A15 are similarly buffered, as indicated by the buffers 82 in each of the address lines designated A11 through A15 of FIG. 3. The address lines A11 through A15 are then applied to the two decoders designated by reference numerals 80 and 81 which may be, for example, conventional 74S138 units. The decoders 80, 81 are used to produce the chip select function, or in other words, to select which one of the individual ROM units 70 through 77 or the individual EPROM units 78 and 79 is to be addressed by the signals of the address lines A0 though A10.

The G1 input of each of the decoders 80, 81 must be high for any output to be present. Since the buffered A15 address line is applied to the G1 input of both decoders 80, 81, the only addresses available in the configuration of FIG. 3 are above hex 8000. The GA input to each of the decoders 80 and 81 must be low and both of the GA inputs are connected to the output of a two input logical NAND gate 83. The first input of NAND gate 83 receives the phase two clock signal from the control bus 37 while the second input receives the buffered Valid Memory Address signal VMA from the control bus 37 via a conventional buffer unit 82. Therefore, when a valid memory address exists, the signal VMA is high and when the second clock phase goes high, the output of NAND gate 83 goes low and this is applied to the GA input of both of the decoders 80 and 81 for enabling same.

The GB input of each of the decoders 80 and 81 must also be in a low state to enable any output from the decoders 80 and 81 to be brought low. The buffered address line A11 is connected directly to the GB input of the second decoder 81 and simultaneously to both inputs of a logical NAND gate 84 whose output is connected directly to the GB input of the first decoder 80. Since NAND gate 84 is being used as a simple inverter on the buffered address line A11, a differentiation is provided between the 2K (2000 bytes) blocks of memory in the circuit of FIG. 3. For example, when the signal on address line A11 is low, indicating an address between hex B000 through B7FF, the low will be supplied to the GB input of the decoder 81 to allow its output Y3 to be brought low to select ROM 70 since the Y3 output of decoder 81 is connected directly to the chip select input $\overline{CS}$ of ROM 70 and the presence of a low at this Chip Select Input enables ROM 70 to be addressed by the address signals A0 through A10 on the address bus 35. The CS input of each of the ROMs 70 through 77 and EPROMs 78 and 79 are connected directly to a +5 volt source of potential to maintain the inputs in a high state.

Alternatively, if the signal on buffered address line A11 is high, the output of the NAND gate inverter 84 goes low and when this low is applied to the GB input of the decoder 80, its Y3 output goes low and is applied to the $\overline{CS}$ input of ROM 71 thereby selecting that particular 2K block of memory, which corresponds to addresses B800 through BFFF. In this manner, the decoders 80 and 81 will respond to the signals on the address lines A11 through A14 to bring one of the five outputs, Y3 through Y7 low to select a particular one of the individual ROM or EPROM units and hence differentiate between each of the various 2K blocks of memory represented thereby.

This produces an increment in the outputs of the decoders 80, 81, i.e., from Y3 to Y4, in 4K steps. Thus hex addresses "B" correspond to the Y3 outputs, "C" addresses correspond to the Y4 outputs, "D" addresses correspond to the Y5 outputs, "E" addresses correspond to the Y6 outputs and "F" addresses correspond to the Y7 outputs. Once again, the signal on the A11 line will select the particular high or low 2K block of memory address as illustrated above. Therefore, each of the sets of addresses B through F represents 4K memory address blocks which are addressed by the outputs of the decoders 80, 81 via the five outputs Y3 through Y7 and differentiations within the 4K blocks are provided by the selection of hgh or low 2K blocks by the signal on the buffered A11 line, and hence the enablement of either decoder 80 (High 2K blocks) or the decoder 81 (Low 2K blocks), respectively.

As previously stated, the lower addresses A0 through A10 are applied directly to the ROM 32 and RAM 33 memory units. Internal decoding of these addresses selects a unique or specific memory location within the chip or particular 2K memory block selected by the decoders 80 and 81 as described above. When one of the chip select inputs $\overline{CS}$ is low to select that particular 2K unit of memory and all other chip select inputs are high, the internal decoding of the signals on the address lines A0 through A10 will select a particuar eight bit segment of data which will be transferred to the data output lines D0 through D7 of the data bus 36 and at the end of the second clock phase, the processor 30 will accept this data from the bi-directional data bus 36.

The data bus directional control will now be explained with reference to FIG. 4. A ten input logical NAND gate 87 has its inputs connected to the $\overline{CS}$ chip select inputs of the ROMs 70 through 77 and EPROMs 78 and 79 of FIG. 3 which are referred to by the inputs designated BL, BH, CH, DH, EH, EL, DL, CL, FH, and FL, respectively, from FIG. 3. NAND gate 87 detects a chip select signal going low on any of the memory units of FIG. 3. Whenever one of the chip select signals $\overline{CS}$ goes low, the output of NAND gate 87 will go high. The high at the output of NAND gate 87 is inverted by the operation of NAND gate 88 which is configured as an inverter causing the output of NAND gate 88 to go low. The output from the output of NAND gate 88 is connected directly to one input of a two input logical NAND gate 89 whose second input receives the read/write signal R/$\overline{W}$ from the microprocessor 30 of FIG. 2 via buffer 90. Therefore, the output of NAND gate 89 is used to control the bi-directional non-inverting quad bus drivers of blocks 91 and 92. The bus drivers represented by blocks 91 and 92 are conventional 8T28 drivers with the first quad bus driver 91 receiving as its inputs the data outputs from data lines D4, D5, D6 and D7 from the memory units of FIG. 3 via the data bus 36 while the inputs of the quad driver of block 92 receives its inputs from the data lines D0, D1, D2 and D3 from the memory units of FIG. 3 via the data bus 36.

The SW and SR inputs of the data bus drivers 91 and 92 control the direction in which the bus drivers are attempting to deliver the signals. When the inputs SW and SR are at a high level, the drivers 91 and 92 will drive the data bus from the processor side but when a low signal is present at the SW and SR inputs, the data bus acts as an input and will drive the processor side with data.

Therefore, when the processor 30 is reading ROM or EPROM from the memory array of FIG. 3, the bus drivers 91 and 92 are driving off of the circuit. This occurs because whenever the memory is reading ROM or EPROM from FIG. 3, one of the inputs of NAND gate 87 is low causing its output to go high. The high at the output of NAND gate 87 causes a low to appear at the output of NAND gate 88 which forces the output of NAND gate 89 high without respect to the value of the R/$\overline{W}$ signal, since a write operation to ROM or EPROM is invalid anyway. This also occurs when the processor 30 writes to an address not found in the memory array of FIG. 3 for in that case, all inputs of NAND gate 87 will be high causing its output to be low. A low at the output of NAND gate 87 causes a high to appear at the output of NAND gate 88 to enable one input of NAND gate 89. However, the other input of NAND gate 89 will be low during a write condition causing the output of NAND gate 89 to be high causing the bus drivers 91 and 92 to drive data from the processor to the address in which it is being written.

However, when the processor 30 reads from some external address, the bus drivers 91 and 92 must transfer data from the external address, whether its a device or a memory unit, to the processor 30. Thus, the signal at the inputs SW and SR of the drivers 91 and 92 must be low. This low is accomplished only if both inputs of NAND gate 89 are high. The first input is high when the input of NAND GATE 88 and hence the output of NAND gate 87 is low which occurs only when all of its inputs are high indicating that none of the chip selects are actuated or, alternatively, that none of the ROMs or EPROMs of FIG. 3 are currently being addressed. The R/$\overline{W}$ signal is high indicating a read condition and therefore the low at the output of NAND gate 89 causes the drivers 91 and 92 to drive data to the processor 30.

The NAND gates 87, 88 and 89 and the buffer 90 act as a data direction control circuit for the bus drivers 91 and 92. This is needed to prevent the bus drivers from trying to drive the processor data inputs while reading from ROM or EPROM. These circuits also make sure that data is transferred in the proper direction during a read from or write to any other address not found in the memory units of FIG. 3.

Figure 5:
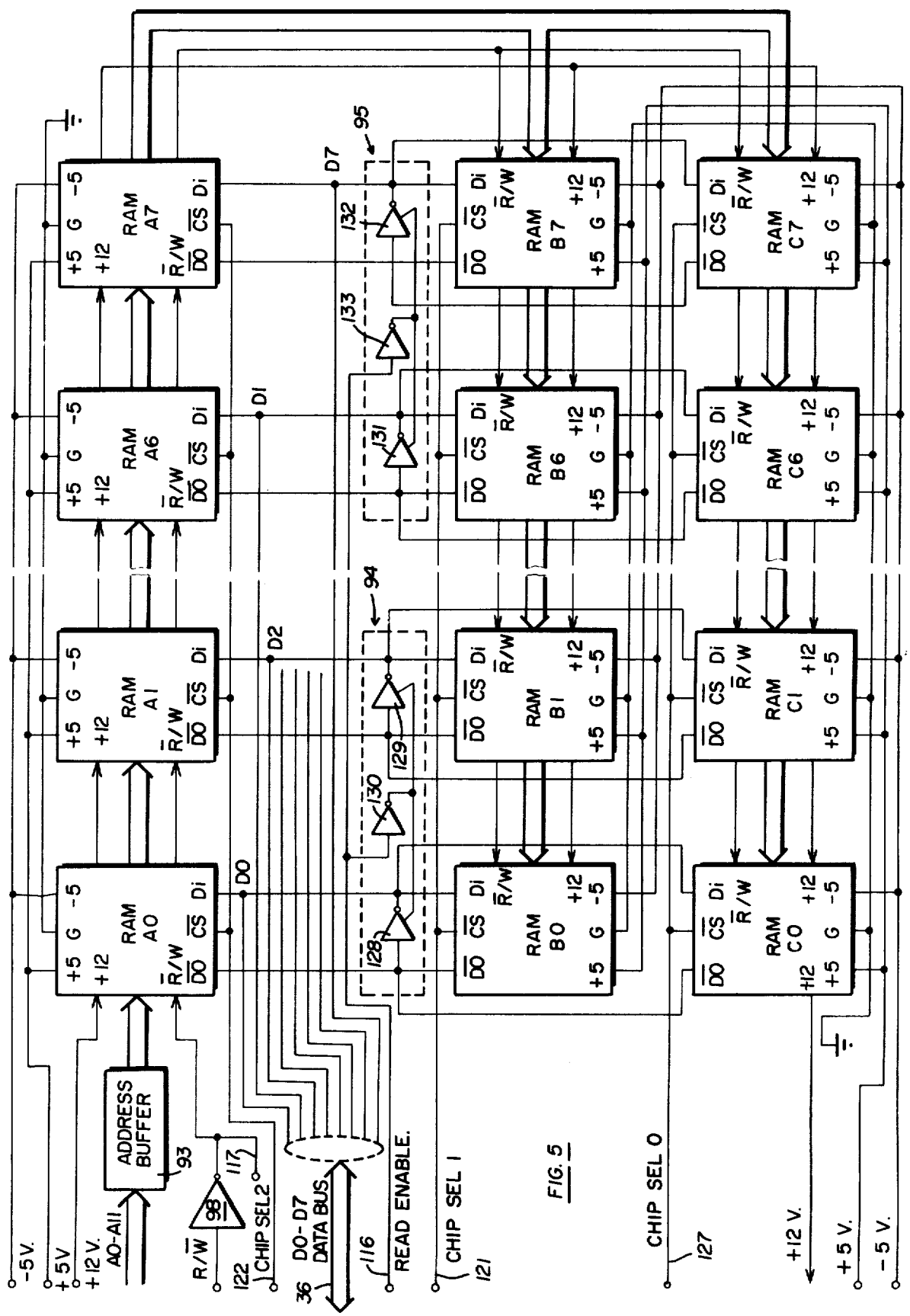
FIG. 5 in an electrical schematic diagram partially broken away, representing the Random Access Memory of block 33 of FIG. 1.
Figure 6:
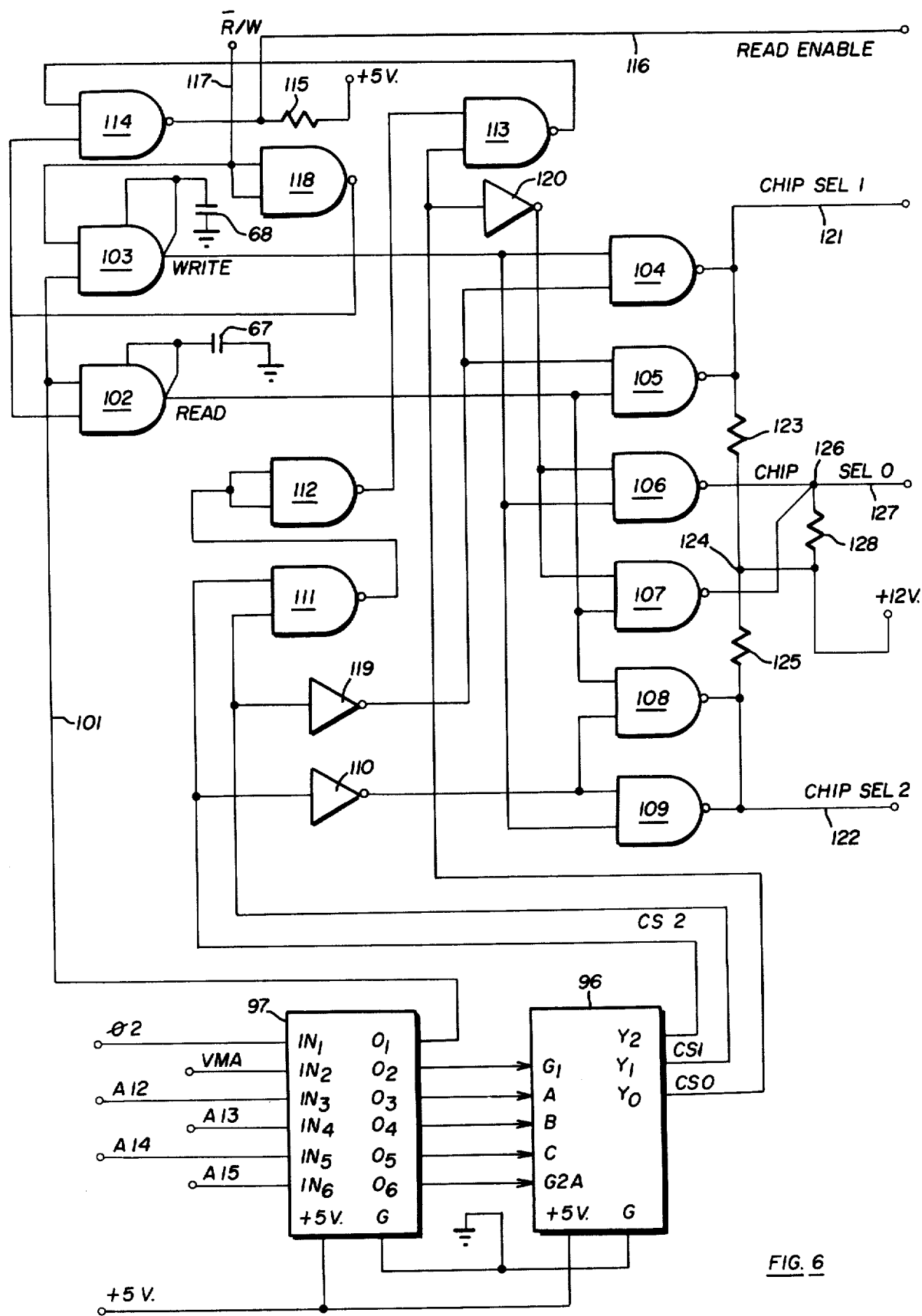
FIG. 6 is a schematic diagram of the chip select circuitry associated with the Random Access Memory of FIG. 5.

The random access memory of block 33 of FIG. 1 will now be discribed with reference to FIGS. 5 and 6. The random access memory of block 33 contains 12K (12,000) of eight bit bytes or read/write memory. This memory is used by the present system to store variables, such as math working registers, scanned pattern storage and the like. The memory contains 24 individual 4K by 1 RAM devices, such a conventional EMM 4200s which are arranged in an array of 3 rows "A", "B" and "C" each of which contains eight individual 4K by one RAM units and hence the individual RAM units are designated A0 through A7 for the first row, B0 through B7 for the second row, and C0 through C7 for the third row. The break lines in the circuitry of FIG. 5 indicate that the middle four memory units of each row have been eliminated for ease of discussion but it is to be understood that each row actually contains eight RAM units in the preferred embodiment of the present invention. It will of course be understood that any given size of memory can be used depending upon the type and quantity of information to be stored.

The circuitry of FIGS. 5 and 6, in addition to the 24 RAM units also includes an address buffer 93, data bus buffers indicated by the dotted blocks 94 and 95, and address decoding/chip select driver circuitry as illustrated in FIG. 6. Memory addresses for the random access memory of FIG. 5 run from 0000 to hex 2FFF. When the microprocessor 30 of FIG. 2 desires to access any of the random access memory locations of FIG. 5, it outputs the desired address on the address bus 35 and brings the VMA signal high during the first clock phase. The read/write line is also brought low at this time for the write mode. The addresses A0 through A11 are applied to all memory chips through the conventional address buffers of block 93 as indicated by the address bus designation extending through all of the RAM units A0-A7, B0-B7, and C0-C7.

The addresses A12 through A15 are applied to the decoder 96 of the circuit of FIG. 6 through the address buffer 97. The decoder 96 decodes which 4K bank the address is in, row A, row B or row C and brings its correct output Y0, Y1, Y2, respectively, low. These active low chip select signals are inverted and applied to the gating circuitry of FIG. 6 as hereinafter described. The outputs of the various gates will perform the actual chip selection on the RAM devices of FIG. 5 by pulling a unit chip select input $\overline{CS}$ low from the normal +12 volts supplied thereto by a pull-up resistor combination, not shown, but known in the art. Each 4K banks and therefore each of the rows A, B, and C has two logical NAND gates cntrolling their chip select inputs, one for the write mode and one for the read cycle. This is necessary due to the chip select input timing requirement of the memory devices themselves. To differentiate between the two cycles, the read/write signal is used. The correct timing is obtained by logical AND delay gates, as hereinafter described, by incorporating a fixed delay in the chip select with respect to the second phase of the clock 31.

The R/$\overline{W}$ signal is obtained from the microprocessor 30 of FIG. 2, inverted by a conventional inverter 98 and then applied to the memory devices as the signal $\overline{R/W}$. It is also applied to one of the logical AND gates as a high signal to enable the write condition delay gate. Likewise, the R/$\overline{W}$ signal is also supplied to a NAND gate which performs an additional inversion for a high enable read condition and to a delay gate as hereinafter described. Therefore, depending upon the R/$\overline{W}$ condition, either a read gate or a write gate will be enabled. The other inputs to these delay gates include the second clock phase signal and a write enable signal for the write circuit. The write enable is tied high through a pull-up resistor and the second clock phase signal is obtained from the non-inverting section of the buffer 97.

The inputs of the address buffer 97 receive the second clock phase signal $\phi$2, the signal VMA and the address signals on lines A12 through A15, respectively. The second clock phase signal is outputted after it is buffered via lead 101 and supplied to one input of a logical AND gate 102 which is used as a Read delay gate and to one input of a second logical AND gate 103 which is used as Write delay gate. Six logical NAND gates 104 through 109 are used to generate the chip select signals for each of the three rows or memory banks previously described. NAND gates 104 and 105 are associated with the generation of the chip select 1 signal for the second or "B" row of RAMs B1-B7; NAND gates 106 and 107 are associated with the generation of the chip select zero signal for enabling the third or "C" row of RAMs C0-C7; and the NAND gates 108 and 109 are associated with the generation of the chip select two signal for activating the first or "A" row of RAMs A0-A7, respectively.

The non-inverting buffer outputs 02, 03, 04, 05, and 06 of the address buffer 97 are connected to the inputs G1, A, B, C, and G2A, respectively, of the address decoder 96 which generates the chip select signals CSO, CS1 and CS2 on its outputs Y0, Y1 and Y2 respectively. The Y2 output of the decoder 96 applies a signal CS2 to the input of an inverter 110 whose output supplies the first input to NAND gates 108 and 109. The signal CS2 is also supplied directly to one input of a logical NAND gate 111 whose output is connected to both inputs of a two input NAND gate 112 used as a buffered inverter. The output of NAND gate 112 is connected directly to one input of a logical NAND gate 113 whose output is in turn connected to one input of a logical NAND gate 114. The output of NAND gate 114 is connected to a +5 volt source of potential through a pull-up resistor 115 and supplies the READ ENABLE signal to the circuit of FIG. 5 via lead 116.

The inverted read/write signal $\overline{R/W}$ from the output of inverter 98 of FIG. 5 is connected via lead 117 to both inputs of a two input NAND gate 118 which serves as a buffered inverter and the output of NAND gate 118, which is the reinverted read/write signal (R/$\overline{W}$) is connected directly to the second input of NAND gate 114 and to the second input of NAND gate 102. The signal $\overline{R/W}$ on lead 117 is also connected directly to the second input of the write AND delay gate 103 previously described. The write output of AND gate 103 is connected to one input of the NAND gates 104 106 and 109 while the write output of AND gate 102 is connected to one input of AND gates 105, 107 and 108. Since either the delayed read or the delayed write signal is connected to one of the NAND gates of the pairs 104, 105; 106, 107; and 108, 109; the proper bank or row of RAMs "B", "C", or "A" can be selected for either a read or a write operation.

The Y1 output of decoder 96 is connected directly to the second input of NAND gate 111 and through an inverter 119 to an input of NAND gate 104 and 105. Likewise, the Y0 output supplies the CSO signal to the second input of NAND gate 113 and simultaneously to the input of an inverter 120 whose output is connected to one input of NAND gates 106 and 107.

The outputs of NAND gates 104 and 105 supply the Chip Select 1 signal to the RAM units B0-B7 via lead 121 while NAND gates 108 and 109 supply the Chip Select 2 signal to the RAM units A0-A7 via lead 122 and NAND gates 106, 107 supply the Chip Select signal to the RAM units C0-C7.

The outputs of NAND gates 104 and 105 whch supply the Chip Select 1 signal to the "B" row of the circuit of FIG. 5 via lead 121 are also connected to one terminal of resistor 123 whose opposite terminal is connected directly to a node 124. Node 124 is in turn connected directly to one terminal of a second resistor 125 whose opposite terminal is commonly connected to the outputs of NAND gates 108 and 109 which supply the Chip Select 2 signal to the "A" row of the circuitry of FIG. 5 via lead 122 as previously described. The outputs of NAND gates 106 and 107 are commonly connected at a node 126 which supplies the Chip Select 0 signal to the "C" row of RAM units C0 through C7 of the circuit of FIG. 5 via lead 127. Simultaneously, node 126 is connected to one terminal of a thrid resistor 127 whose opposite terminal is connected both to node 124 and to a +12-volt source of potential.

The Chip Select 2 signal is supplied via lead 122 of FIG. 6 to the circuit of FIG. 5 to commonly connect the chip select inputs $\overline{CS}$ of each of the first row or bank of RAM units A0 through A7, respectively, while the Chip Select 1 signal is supplied via lead 121 to all of the chip select inputs $\overline{CS}$ of the RAM units B0 through B7 of the second bank or row of memory units of FIG. 5. Similarly, the Chip Select 0 signal is commonly connected to each of the chip select inputs $\overline{CS}$ of the RAM units C0 though C7 via lead 127 from FIG. 6.

The Read Enable signal generated in the logic circuit of FIG. 6 is supplied via lead 116 to the data bus buffers of dotted blocks 94 and 95 as hereinafter described. The data in and data out terminals of each of the RAM units, designated Di and $\overline{Do}$ are commonly connected together for corresponding columns in the array of FIG. 5. In other words, the Di terminals of the RAM units A0, B0, and C0 are commonly connected together and the $\overline{Do}$ terminals are commonly connected for the RAM units A0, B0 and C0. The same is true for the corresponding Di and $\overline{Do}$ terminals of the RAM units A1, B1, C1; for A2, B2, C2; . . . A6, B6, C6; and A7, B7, and C7.

A triggerable inverter 128 has its input connected to the lead commonly connected the $\overline{Do}$ terminals of RAM units A0, B0, C0 and its inverting output connected to the lead commonly coupling the Di terminals of RAM units A0, B0, C0. Similarly, a triggerable inverter 129 has its input connected to the lead commonly connecting the $\overline{Do}$ terminals of RAM units A1, B1, C1 and its inverting output connecting directly to the lead commonly coupling the Di terminals of RAM units A1, B1 and C1. The Read Enable signal from the circuit of FIG. 6 is connected via lead 116 to the input of an inverter 130 whose output is commonly connected to the triggers of inverters 128 and 129 and the combination of the inverters 128, 129 and 130 within the dotted block 94 form a data bus buffer whose operation will be described hereinbelow. A similar set of triggerable inverters 131 and 132 are coupled between the $\overline{Do}$ and Di terminals of RAM units A6, B6, C6 and A7, B7, C7, respectively and a similar inverter 133 has its input connected to the read enable lead 116 and its output connected to the common triggers of inverters 131 and 132 to form the data bus buffer of dotted block 95. It will be understood that similar data bus buffers can be provided forthe remaining RAM units not expressly shown in FIG. 5. The remaining connections shown in FIG. 5 are self explanatory and require no further comment, it being understood that the +5 volt, −5 volt and +12 volt DC power supplies are conventionally available and that the 8 bit data words read into or out of the RAM units of FIG. 5 are conveyed to or read from the addressed memory location via the data bus 36 represented by the data lines D0 through D7.

During the read cycle, the processor 30 accepts the data on the data bus at the end of the second clock phase which is approximately 450 ns long. The read access time from the memory device is a maximum of 215 ns after the chip selection is made. Therefore, there is about 230 ns to spare, discounting propagation delays along the bus and the like. Therefore, a read cycle has a small delay built into it by the use of the timing capacitor 67 associated with the delay AND gate 102, if for no other reason than to conserve power. The delayed Read output of AND gate 102 is supplied to one input of the NAND gates 105, 107 and 108 to enable one of these gates, and therefore, one in each pair of gates associated with each 4k bank of RAM units A0 through A7, B0 through B7; and C0 through C7, respectively, to perform the desired chip select funcion for the read cycle.

Similarly, during the write cycle, the data at the memory devices input must be that which is to be stored when the chip select occurs. The processor 30 places this data on the data bus up to 200 ns after the second clock phase has begun. Therefore, the delay AND gate 103 must delay the input a minimum of 200 ns. Again, this delay is enabled by the use of the timing capacitor 68 associated with the write AND gate 103 and the delayed Write output is supplied to the other three NAND gates 104, 106 and 109 of the pair of NAND gates associated with each 4k bank of memory to enale one of their outputs for chip select during the write cycle.

The data stored in any given RAM unit is inverted when it is read from the device and therefore, an inversion is required for the processor to read back what has been written. This function is performed by the inverting tri-statable data bus buffers of dotted blocks 94 and 95 of FIG. 5. To prevent contention between these buffer outputs and the data bus 36, which are hard wired together, the Read Enable control input on lead 116 is used to place the buffer outputs in a high impedance state where they will not sink or source signal level currents. During the read cycle their control inputs are brought low enabling their outputs to transfer the complement of their input. This will drive the data bus low or high for the processor read cycle. This is performed by the open collector NAND gate 114 whose output is pulled high to the +5 volt source of potential by a pull-up resistor 115. The output of NAND gate 113 will go high when any of these memory addresses occur and this high is applied to the control gate input of NAND gate 114. The other input to NAND gate 114 is the doubly inverted R/W signal from the output of the inverter-configured NAND gate 118. Therefore, during any chip select and a read condition, the output of NAND gate 114 will go low. The low Read Enable signal on lead 116 will be inveted by the inverters 130, 133 of the inverting tri-statable buffers 94, 95 causing their outputs to go high to trigger their respective inverters 128, 129 and 131, 132. This will allow the buffers 94, 95 which may be, for example, conventional 8T98 devices, to transfer data driving the data bus 36. If these gates are to be used as buffers and inverters elsewhere in the system, they require a constant enable, thus the appropriate pin of the buffers 94 and/or 95 may be grounded, as conventionally known, for standard 8T98 inverting tri-statale buffers.

Figure 7:
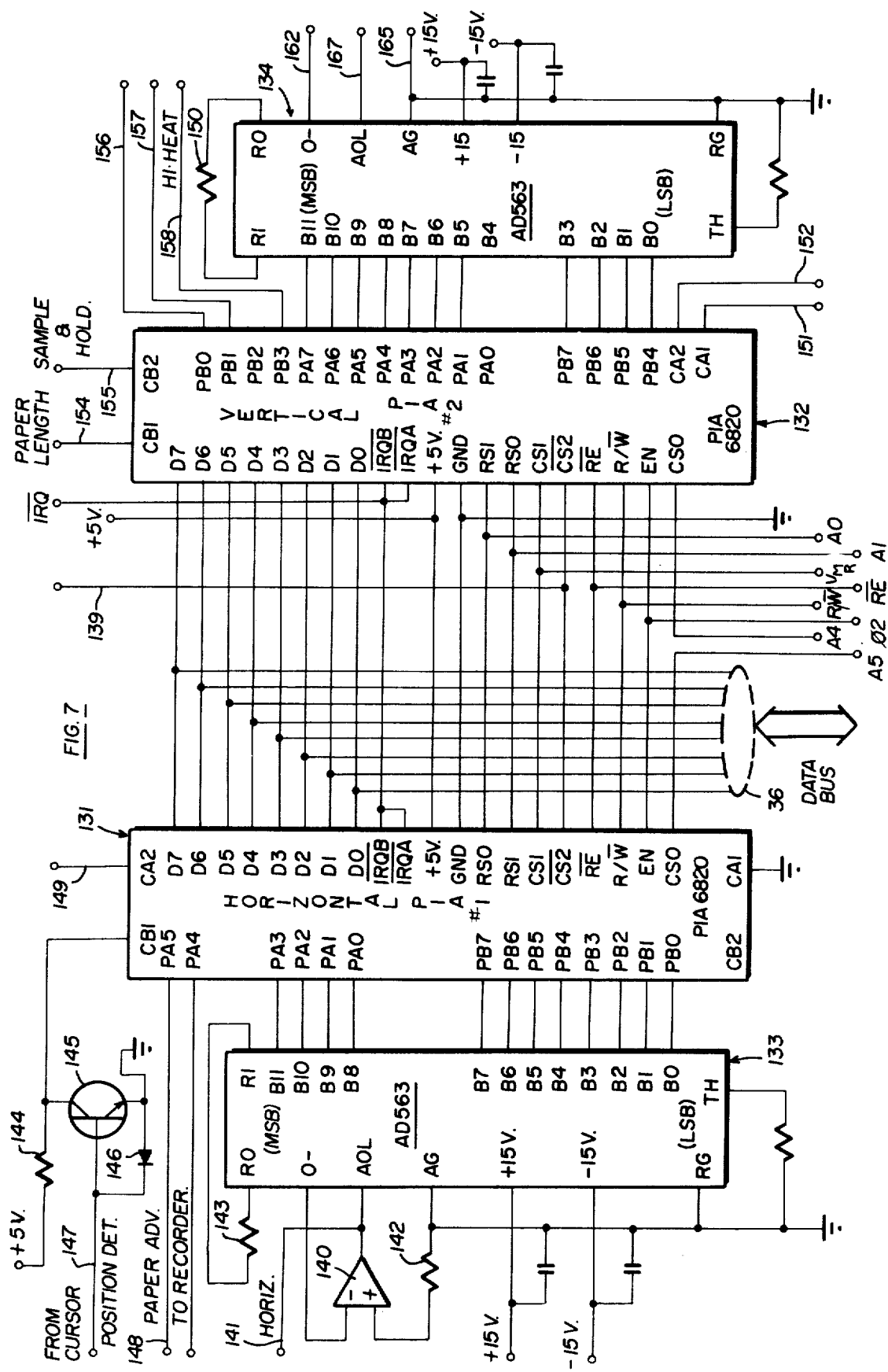
FIG. 7 is a detailed block diagram of a portion of the Peripheral Interface Adaptors of block 34 and the I/O circuitry of block 46 of FIG. 1.

The PIA block 34 and I/O block 46 of FIG. 1 include the various data bus drivers, address bus drivers, decoders, A/D converters, and Peripheral Interface Adapter which function to take information to and from the various peripheral devices through the PIAs and back to the processor 30. FIG. 7 shows a first Peripheral Interface Adapter 131 designated PIA #1 and a second Peripheral Interface Adapter 132 designated PIA #2. Further, the circuit of FIG. 7 includes two Analog-to-Digital converters 133 and 134 which form part of the I/O circuitry of block 46 and which are used to interface the analog perhipherals with the PIAs 131 and 132, respectively.

Figure 16:
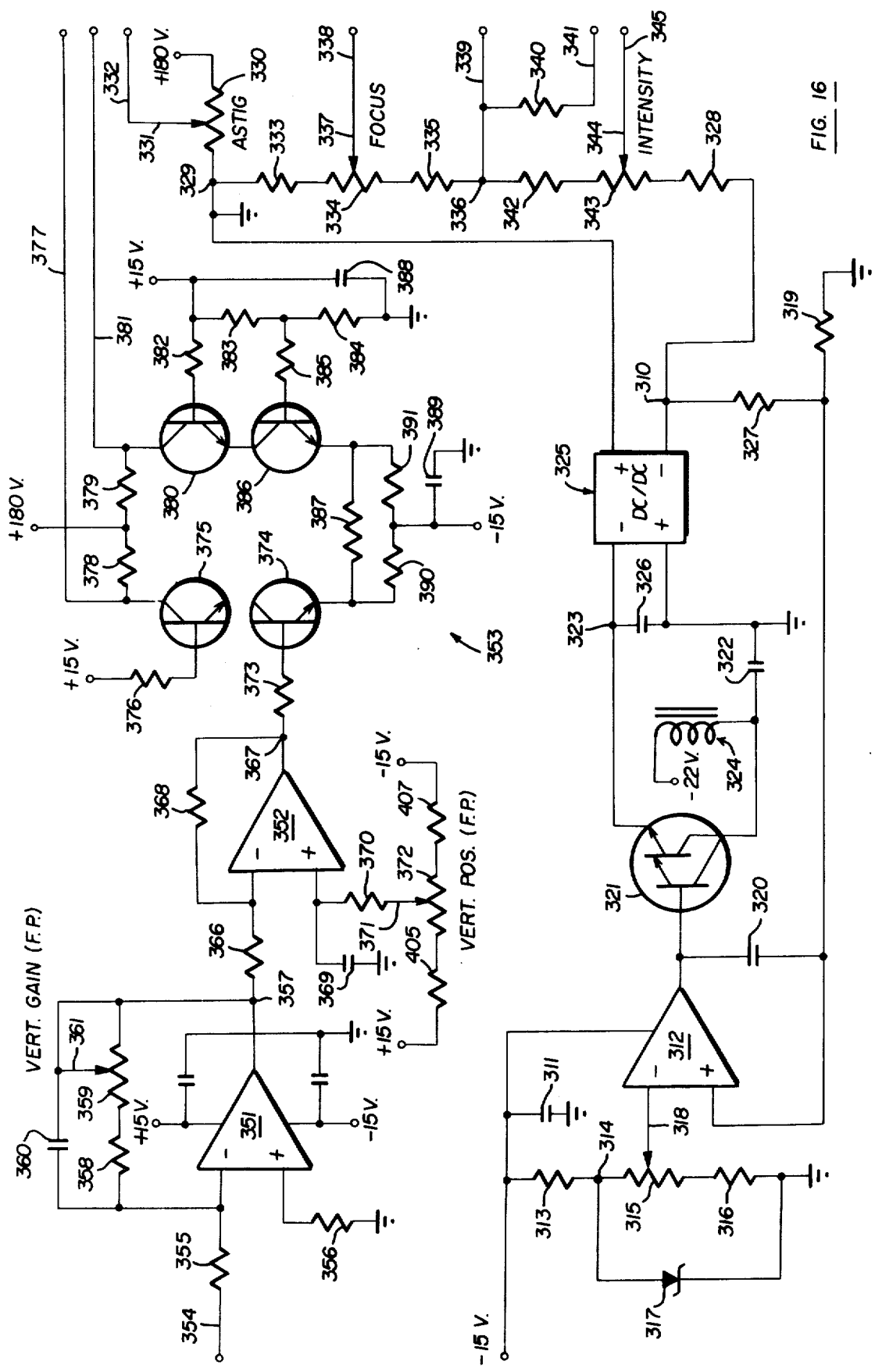
FIG. 16 is an electrical schematic diagram of the vertical deflection circuitry and control circuitry associated with the oscilloscope of block 48 of FIG. 1.

The Peripheral Interface Adapters 131 and 132 of FIG. 7 and 135 and 136 of FIG. 16 provide the digital output for the microprocessor system of the present invention. The PIAs utilized are conventional MC6820 devices as described in *MICROPROCESSOR APPLICATIONS MANUAL*, Motorola Semi-Conductor Products, Inc., McGraw-Hill Book Co., New York, N.Y. 1975, which is incorporated by reference herein for the purpose of describing and understanding the microprocessor, system configuration, PIAs, DACs, etc.

The PIA provides a flexible method of connecting byte-oriented peripherals to the microprocessor 30. The PIA, while relatively complex itself, permits the microprocessor 30 to handle a wide variety of equipment types with minimal additional logic and simple programming. Data flows between the microprocessor 30 and the PIAs 131, 132, 135, and 136 through the eight bi-directional data lines D0 through D7 comprising the data bus 36 of FIG. 1. The direction of data flow is controlled by the microprocessor 30 via the read-write input to the PIAs. The "MPU side" of the PIA also includes three chip select lines, CSO, CS1, and $\overline{CS2}$, for selecting a particular PIA. Two addressing inputs, RS0 and RS1 are used in conjunction with a control bit within the PIA for selecting specific registers within the PIA. There are a total of six 8-bit registers in each PIA and they are separated into an A and B side, each side containing a control register, data direction register, and an output data register. From the microprocessors point of view, each PIA is simply four memory locations that are treated in the same manner as any other Read/Write memory.

The microprocessor or MPU 30 also provides a timing signal to the PIA via the Enable input. The Enable (EN) pulse is used to condition the PIAs internal interrupt control circuitry and for timing the peripheral control signals. Since all data transfers take place during the second clock phase signal, the Enable pulse used in the system of the present invention is the second clock phase signal $\phi 2$.

The "Peripheral side" of the PIA includes two 8-bit bi-directional data buses (PAO through PA7 and PBO through PB7) and four interrupt/control lines CA1, CA2, CB1, and CB2. All of the lines on the "Peripheral side" of the PIA are compatible with standard TTL logic. In addition, all lines serving as outputs on the "B" side of each PIA will supply drive current. Additional detailed information of the internal workings of a PIA should not be required for understanding the operation thereof as used in the present invention and for further detail, reference may be had to the above-identified publication.

The two PIAs 131 and 132 of FIG. 7 are wired direct to the data bus 36 (data lines DO through D7) and to the $\overline{IRQ}$, RE, R/W, and $\phi 2$ terminals of the microprocessor 30 of FIG. 2 with the second clock phase signal $\phi 2$ wired to the enabled inputs. PIA 131 is at address 8010 and PIA 132 is at address 8020. The most significant byte of the address is decoded by the address decoder 138 of FIG. 10 which is a conventional one-of-eight address decoder. The inputs of the decoder 138 are the address signals A12, A13, A14 and A15 from the address bus 35. The 8000 is decoded by the address value A15 being high which brings the G1 input pin of the detector 138 high to enable the decoder. With low signals on the address inputs A12, A13 and A14, the output YO will go low. This low is connected via lead 139 from the decoder 138 of FIG. 10 to the $\overline{CS2}$ chip select inputs of both of the PIAs 131 and 132. The chip select input CS2 is an active low input. Further address decoding is by virtue of the address line A4 performing a chip select CSO of PIA 132 and the signal on address line A5 performing a chip select at the CSO input of PIA 131. This provides the required differentiation between addresses 8010 and 8020.

The third chip select input for PIAs 131 and 132 is the signal VMA which is supplied to the CS1 input of both PIAs 131 and 132 to insure that there are no spurious responses from non-valid memory addresses showing up on the address bus 35. There exists a difference in the register select inputs RS0 and RS1. The vertical PIA 132 or address 8010 has the address line AO connected to the RS1 input and the address line A1 connected to the RSO input which is the reverse of the normal connection. The horizontal PIA 131 or address 8020 has the address line AO connected directly to the RSO input and the address line A1 connected directly to the RS1 input. This is done to enable the processor 30 to read or write the PIA data as one 16 bit word which enables a quicker cycle time for the input conversion routine.

No data bus buffering is required with the data outputs DO through D7 which are connected directly to the data bus 36. The read and/or write cycle is relatively straight forward. The address is put on the address bus 35 by the microprocessor 30 to activate the YO output of decoder 138 of FIG. 10. When the YO output of the decoder goes low, this low is transmitted via lead 139 to enable the PIAs 131 and 132 of FIG. 7. As soon as the VMA signal goes high, another chip select is made. Address A4 or A5 being high will select either one or the other of the PIAs 132, 131 respectively. AO and A1 then select which internal register the particuar PIA responds to and the signal on the read/write line R/W will go high indicating that the microprocessor desires to read data from the PIAs 131 and 132. As soon as the second clock phase signal $\phi 2$ goes high on the PIA enable inputs EN, the selected device will respond. If it is a write cycle, the data will be accepted when the second clock phase signal $\phi 2$ at the EN input goes back low. On the other hand, if it is a read cycle, the data will be transferred to the data bus for the processor to accept at the end of the second clock phase signal $\phi 2$. The non-selected PIA outputs to the data bus 36 remain in a high impedance state preventing bus connection.

With this brief description of the PIAs 131 and 132 and the operation thereof, the horizontal and vertical DACs 133 and 134 will be described and related to the PIAs 131 and 132 respectively.

The digital-to-analog converter or DAC 133 is dedicated solely to producing the horizontal ramp of voltage for the oscilloscope module block 48 of FIG. 1 and the other DAC 134 is used for multiple functions. The primary function of DAC 134 is to allow the microprocessor 30 to read the input signal provided by the amplifier chain and sample and hold circuits which connect the DAC 134 to the photomultiplier tube or detector of block 59 of FIG. 1 as hereinafter described. The secondary function of the DAC 134 is to provide vertical deflections for oscilloscope or to the recorder as hereinafter described.

The horizontal DAC 133 provides the system oscilloscope of block 48 of FIG. 1 with the required horizontal deflection signal. This signal starts at +10 volts and is reduced toward +5 volts to provide the deflection. In other words, a +10 volt output from the DAC 133 is related to the leftmost position on the oscilloscope phase. However, when no oscilloscope display is required, the horizontal output is zero volts to bring the electron beam off screen to the right.

As previously stated, the DACs 133 and 134 are conventional digital-to-analog converters such as the commerically available AD 563 or AD 565 units and each includes a precision resistor network, a voltage reference and a plurality of transistor switches which are driven indirectly by the associated PIA 131 or 132 respectively. An input count on DAC 133 of all zeroes or hex 000 is equal to a zero volt output. Incrementing the count to 001 where the least significant bit at the input B0 is set high, produces an increase in the output level of approximately 2.44 millivolts. There is a maximum number of counts or levels of 4096. Therefore, the full scale output of ten volts is divided up into 4096 discrete levels. The inputs of the DAC 133 are arranged in a binary or hex input sequence as opposed to a BCD (binary coded decimal) count. As the count is increased, weighted resistors are switched into a current bus whose output is taken at the output designated "0−" of the DAC 133. This output is applied to the inverting input of a conventional operational amplifier 140 which acts as a current-to-voltage converter, as known in the art. The output of operational amplifier 140 is the analog conversion of the digital inputs and is connected to the AOL terminal of DAC 133 and is supplied via lead 141 to carry the horizontal deflection signal HORIZ to the corresponding input of the scope control circuit of FIG. 15 as hereinafter described. The operational amplifier feedback path includes a resistor which is inside the DAC 133 while the resistor 142 is coupled between the positive input of the operational amplifier 140 and the analog ground input AG to reduce offset effects by referencing the non-inverting input of the operational amplifier 140 to analog ground.

The resistor 143 coupled between the R0 and R1 terminals enables the DAC 133 to be powered by the ±15 V supplies while still retaining TTL logic level requirements at its inputs. Resistor 143 functions as a gain setting element for an internal constant current circuit which drives the internal weighted resistor network previously discussed, as conventionally known.

Figure 15:
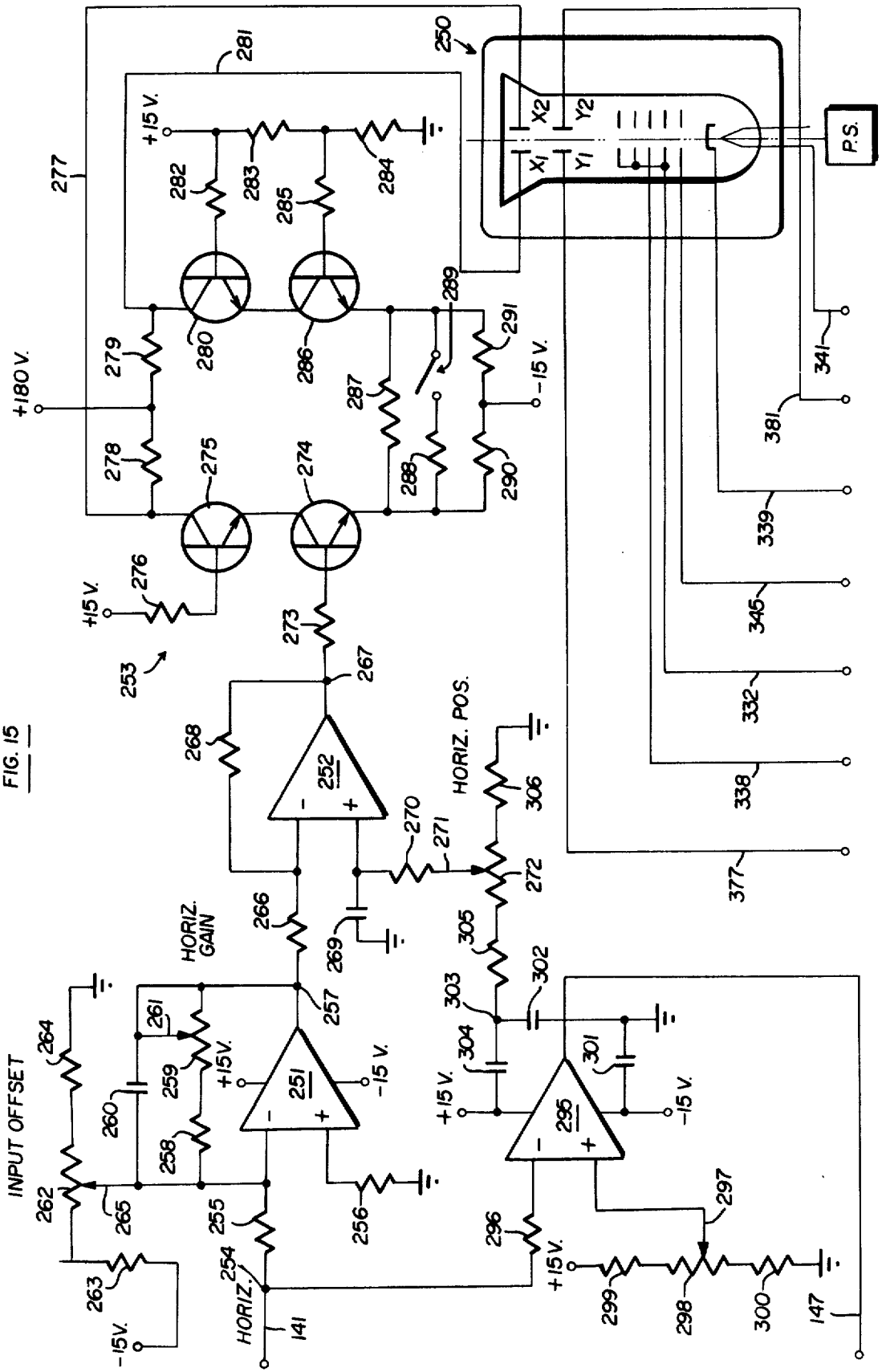
FIG. 15 is an electrical schematic diagram of the horizontal deflection circuitry associated with the oscilloscope of block 48 of the present invention.

As stated, the output of DAC 133 is the analog output of the operational amplifier 140 and supplies the signal HORIZ via lead 141 to the scope control circuit of FIG. 15. The count at the horizontal DAC 133 starts at an all high or full scale +10 volt output and decrements or ramps downward under control of the microprocessor 30 as the vertical or analog information is presented by the vertical DAC 134 as hereinafter described. As the end of the vertical information is reached, the horizontal DAC 133 is reset to the full scale value of +10 volts and the progress starts over again. Thus a continuous dislay of the scanned pattern is achieved on the oscilloscope of block 48 without the need to rescan the original sample a second time, rescan the chart paper, or the like.

For the most part, the vertical DAC 134 is a duplication of the horizontal DAC 133 with the exception of the PIA to DAC interface. The horizontal DAC 133 has its least significant bit input from PB0 of PIA 131 and increases in powers of two until PB7 and then continues from PA0 through PA3 at the most significant bit (MSB) which is supplied to the B11 input of DAC 133. The vertical DAC 134 has its least significant bit supplied from the PB4 output of the PIA 132 and received at the B0 or least significant bit (LSB) input of the DAC 134 and the values increase from PB4 through PB7 and then from PA0 through PA7 where the most significant bit is supplied to the B11 input of DAC 134. Although this appears to be an obvious difference, it is not of great concern since each is driven by the processor 30 by different software routines stored in the ROM memories of FIG. 3. The vertical DACs interaction with external circuitry will be further discussed as required in the circuit descriptions which follow.

The particular inputs and outputs to be referred to hereinafter are briefly discussed below. The CB1 input of PIA 131 is connected to a +5 volt source through a resistor 144 which has one terminal connected to the +5 volt source and its opposite terminal connected directly to the collector of a transistor 145. The emitter of transistor 145 is grounded. The base of transistor 145 is connected to the cathode of a diode 146 whose anode is connected to ground and to a position detection input from the cursor circuitry to be described hereinafter via lead 147.

A paper Advance signal is supplied to the recorder circuitry as hereinafter described via lead 148 from the PA5 output of PIA 131 while the PA4 output is supplied to the recorder as a spare for possible future applications. The CA2 output of DAC 131 is connected via lead 149 to the circuit of FIG. 10 as hereinafter described.

The RO1 and R12 terminals of DAC 134 are similarly connected through a resistor 150 to enable the ±15 volt source to be applied to the device without effecting the required TTL input levels. Furthermore, the CA1 terminal of PIA 132 is connected via lead 151 to the output of the sample clock circuit of FIG. 12 while the CA2 terminal is connected via lead 152 to the control input of a switching network of block 153 of the circuit of FIG. 9 as hereinafter described.

Yet further, the CBI terminal is connected via lead 154 to the Paper Length control output or chart length timer output of the recorder circuitry as hereinafter described. Terminal CB2 is connected via lead 155 to the logic input of the sample and hold circuitry of FIG. 9. The PBO input of PIA 132 is connected via lead 156 to the circuit of FIG. 9 while the PB1 output of the PIA 132 is connected to the event marker circuitry of FIG. 14 via lead 157. The PB3 output of PIA 132 is connected via lead 158 to carry the HI HEAT command signal to the recorder circuitry as hereinafter described.

Referring briefly to the vertical DAC trim circuit of FIG. 11, the remaining terminals of DAC 134 will be discussed. A trim resistor 159 has one terminal connected to a +15 volt source of potential and its opposite terminal connected to a −15 volt source of potential. The trimming arm 160 is positionable along the resistor 159 to control the amount of resistance in series with the trimming arm 160 which is connected to one terminal of a resistor 161 whose opposite terminal is connected both to the O- input of the DAC 134 via lead 162 and to the inverting input of an operational amplifier 163 whose noninverting input is connected through a resistor 164 and lead 165 back to the analog ground input AG of the DAC 134. The output of the analog amplifier 163 is connected via lead 166 to the AOL input of the DAC 134 and simultaneously to the input of the switching module of FIG. 9 via lead 167. The trimmer resistor 159 allows a small amount of current to be summed at the inverting input of the operational amplifier 163 through resistor 161. By selectively positioning the trim arm 160 to control the amount of trim resistance, the output of the operational amplifier 163 can be adjusted to a zero out condition. Many of these inputs and outputs will again be referenced in the description of the circuits which follow.

The detector circuitry represented by block 59 of the optical scanning network 54 of FIG. 1 preferably includes a photo-multiplier tube (PMT) 170 which transforms the light passing through or emitted from the sample to be analyzed into an electrical analog signal which is capable of being amplified. As light (photons) strike the photocathode within the PMT 170, the photocathode gives off electrons by the process known as photoemission. These emitted electrons are electrostatically focused and accelerated toward a positive (less negative) charged dynode. When the electrons strike the dynode more free electrons are given off and this phenomenon is known as secondary emission. These are in turn accelerated toward another dynode, and so on, until all dynode stages of the PMT 170 have been utilized. The final element is the anode which collects the electrons and supplies them to the external circuit connection. A very high sensitivity and gain can thus be achieved by using today's modern photoemissive coatings on the cathode and multiple dynodes. In the preferred embodiment of the present invention, a Hamamatsu R300-7 is used. This is a nine stage PMT with an absolute maximum applied voltage rating of 1000 volts. The PMT 170 will respond to light signals from 185 nanometers at 70° output almost linearly and come to a peak of 100° at 340 nanometers and then almost linearly decreased until zero percent is reached at approximately 650 nanometers. To simplify the discussion of the front end amplifier chain, the linear mode will be discussed first followed by a description of the logarithmic or log mode.

The anode of the photomultiplier tube 170 is connected to the inverting input of an operational amplifier 171 configured to operate as a current-to-voltage converter with one of two possible feedback paths depending upon the positioning of the K1 relay-operated switches W1 and W2. In one mode of operation, determined by the K1 relay closing the W1 and W2 switches on the relay contacts C1 and C2 respectively, a resistive path is established. This is a linear mode of operation with relay K1 de-energized. In this configuration, the inverting input of the operational amplifier 171 is connected through a capacitor 172 to the output of the operational amplifier. Simultaneously, the inverting input is connected through the closed relay contact switch W1 and contact C1 which connects through a series path including a trimming resistor 172 and a resistor 173 which has one terminal connected to the trimming resistor 172 and its opposite terminal connected to the C2 contact. The feedback path is complete since the W2 relay switch is closed on contact C2 to connect resistor 173 to one terminal of a third resistor 174 whose opposite terminals connected directly to the output of the operational amplifier 171 to complete the feedback path. The non-inverting input of operational amplifier 171 is connected to the grounded output of PMT 170 and the dotted loop about the photo-multiplier tube outputs indicates that the shielded cable-type connection is also grounded. Within certain practical limits, the output voltage of the operational amplifier 171 will equal the product of the input current and the feedback resistance and high frequency roll-off is provided by the capacitor 172.

The output of the operational amplifier 171 is connected through series resistors 174 and 175 to the inverting input of operational amplifier 176. A feedback path is established between the inverting input of the amplifier 176 and its output and the feedback path comprises the parallel combination of a resistor 177 and a capacitor 178. The amplifier 176 has its input impedence determined by the value of resistor 175 and a fixed DC gain. Although the amplifier is internally compensated, the capacitor 178 provides additional high frequency roll-off by providing a low resistance negative feedback path starting at a pre-determined frequency depending upon the value of resistors 175 and 177 as known in the art. The non-inverting input of amplifier 176 is referenced to ground through a resistor 179 and the K1 relay switch W4 which is closed upon the contact C4 which is grounded whenever the K1 relay is de-energized indicating that the linear mode of operation has been requested. The output of amplifier 176 is supplied to a front panel-controlled amplifier 180 via the closed relay contacts W3,C3 as hereinafter described.

The input amplifier 171 is a chopper stablized amplifier while the amplifier 176 is primarily a gain amplifier. When a flourescent scan is made or flourescent technique is employed, there is a linear conversion. Therefore, the K1 relay is de-energized causing its controlled switches W to close upon the C relay contacts. There is an option to use the linear feedback mode of operation even when a visible light-type scan is made. This could be used, for example, when the light being measured is relfectance rather than light transmission or light emission or the like.

In the logarithmic or log mode of operation, the relay K1 is energized by a high level signal from the CA2 output of the horizontal DAC 131 via lead 149, as hereinafter described, causing the relay-operated contacts W1, W2, W3 and W4 to close upon the normally opened contacts 01, 02, 03, and 04, respectively. This establishes the logarithmic mode as follows. When the W1 switch closes upon contact 01, the feedback path between the inverting input of amplifier 171 and the output of the amplifier includes the parallel combination of a transistor 181 used as a logging element. The transistor 181 may be a conventional TD 401 having its base connected directly to ground, its collector connected directly to the 01 contact and its emitter connected directly to the 02 contact. A N-channel JFET transistor 182 is connected across transistor 181 with the gate electrode being connected to the contact 01 and the source-drain electrodes being commonly coupled to the emitter of transistor 181 and the contact 02. Therefore, a closed loop negative feedback path is established between the inverting input of amplifier 171 and its output via the combination of transistors 181 and 182 and resistor 174.

High frequency compensation for the operational amplifier 171 is provided by the combination of resistor 174 and capacitor 172 as known in the art regardless of whether the amplifier is operating in the linear or the log mode. In the log mode of operation, the amplifier 171 will try to maintain the collector current in transistor 181 equal to the input current by adjusting its output voltage. The output of the operational amplifier 171 is applied to the emitter of transistor 181 through resistor 174 and the closure of the W2 switch on contact 02. The current transfer function for the logging element 181 varies exponentially with the emitter voltage. Therefore, as the input currents (the signal from the PMT 170) are increased (indicating that more light has been detected), the output of the amplifier 171 is increased to go more positive. This increase in the output of the amplifier 171 is sensed by the feedback transistor 181 as an increase in its emitter voltage. The increase in the emitter voltage increases the transfer characteristic of the transistor 181 implying that the output does not need to be as high in order to maintain the collector current equal to the input current. However, the loop time is fast so that there is no problem with servoing.

One problem that does exist occurs when the output of the amplifier 171 drops below the base-to-emitter voltage of the transistor 181 which is required to maintain its conduction. At this point, the stage gain goes open loop and the output may go negative. The circuit is protected from this by transistor 182 which is an N-channel JFET transistor utilized as a low forward bias diode to clamp the circuit when the output goes negative. Additionally, a Log Trim Resistor 183 which is tapped through a resistor 184 acts as an input to the circuit to provide proper bias conditions for the logging element 181. This input is adjusted when scanning a step to insure proper size steps at the high optical density (dark) end. In effect what is being done is injecting the proper amount of offset to bias the logging element 181 for logarithmic performance at very low signal levels where the gain, by definition, is very high. The high gain associated with small outputs in the amplifier 171 and the "dark" current from the PMT 170 may be enough to shift the output from its proper position along the exponential response curve of the logging element 181.

The output of the first amplifier stage is supplied through resistor 174 to the inverting input of the inverting amplifier 176. The non-inverting input of amplifier 176 is now reference to the emitter of a transistor 185 whose base and collector are commonly connected to ground and whose emitter is connected to a +15 volt source of potential through a resistor 186. The emitter of the PNP transistor 185 is also connected directly to the contact 04 so that in the log mode of operation, the non-inverting input of amplifier 176 is connected to the emitter of transistor 185 via resistor 179, switch W4 and contact 04. This has the effect of converting the amplifier 176 into a difference amplifier. If the logging element 181 is a conventional TD401 which is a dual transistor package, then transistor 185 which is the other half of the package has been biased into conduction at its emitter junction. This produces a base to emitter reference which is used to provide a temperature offset correction due to shifts in the logging element transistor's base-to-emitter voltage. This reduces the offset effects of temperature-related drift of the transistors 181 and 185 thus reducing the need for zero adjustment.

In the log mode of operation, the output of the amplifier 176 is connected through a resistor 187 to the inverting input of a unity gain inverting buffer including operational amplifier 188. The non-inverting input of amplifier 188 is connected to ground through a resistor 189 and a negative feedback path is established between the inverting input of amplifier 188 and its output thorugh a feedback resistor 190. The output of the unity gain inverting buffer amplifier 188 is then connected directly to the contact 03 and then via switch W3 to the input node 191 of a control amplifier 180. Resistor 189 reduces the effects of input bias currents thus reducing some output offset and the gain of this stage is set by the ratio of the resistors 190, 187 and is preferably unity or one.

The control amplifier stage includes an operational amplifier 180 which is used to control the gain as well as the zero or offset adjustment of the amplifier chain between the PMT 170 and the sample and hold circuitry to be described hereinafter. The input node 191 is connected to ground through a resistor 192 and is also connected through a resistor 193 to the inverting input of the amplifier 180. The non-inverting input of the amplifier 180 is connected directly to ground and its output is taken from node 194 which is connected through resistor 195 and lead 196 to the low pass filter stage of FIG. 9 as hereinafter described.

The inverting input of amplifier 180 is connected to the output node 194 through a capacitor 197. In parallel with the capacitor 197 is a resistor network representing front panel gain control and front panel zero adjustment. A front panel zero adjustment trim resistor 198 has one terminal connected directly to a +15 volt source of potential and its opposite terminal connected through a resistor 199 to a −15 volt source of potential. The adjustable tap or arm 200 which selects the value of the trim resistance in the circuit is connected through a resistor 201 to the inverting input of the amplifier 180. Simultaneously, the inverting input of the amplifier 180 is connected through a resistor 202 to a front panel manually adjustable gain control arm 203 which is used to select the value of resistance in the circuit by adjustment along a front panel manual gain trim resistor 204. The trim resistor 204 has one terminal connected directly to ground and its opposite terminal connected to the node 194 at the output of amplifier 180.

Resistor 192 prevents the inverting input of the amplifier 180 from floating during switching of the K1 relay. The input resistance of amplifier 180 is determined by the value of the resistor 193. Minimum operational gain is established by the resistor 202 to unity with the front panel gain control at maximum counter-clockwise position. Maximum gain is set by the front panel gain control to about 20 at maximum clockwise adjustment. The inverting input acts as a summing junction for the analog signal and an offset current. The offset current is provided by the front panel zero control adjustment through resistor 201 and is limited on the negative excursion by the value of resistor 199. High frequency roll-off is provided by capacitor 197, as conventionally known, and the control amplifier 180 operates as an inverting amplifier with external controls. The front panel zero control effects the negative bias and the manual gain control effects the feedback, as known in the art.

A brief example of the usefulness of the adjustments is as follows. In some testing, such as in the testing of HDL cholesterol, the background on the slide may be relatively opaque and will block out some of the light as will sample itself. The zero adjustment on the front panel will change the baseline or operating characteristic to remove the opaque background light from being a factor in constructing the ultimate trace. The manual gain may be utilized to increase the amplitude of the incoming signal. For example, this can be used to go off scale with the highest peak to provide greater deflection of subsequent peaks. This is especially important for fluorescent signals which are lower level peaks than the visible light signals. In cholesterol testing, the total amplitude signal from base line to peak is about 0.3 OD and it is riding up around 2 OD so it is essential to remove the 2 OD background with the zero adjustment and then increase the high level gain so that the 0.3 OD signal is amplified to give a full scale reading of the larger signals. In comparison, in serum protein testing, the signal is approximately 1½ OD change from base line to the top of the peak. This provides some idea of the relationship involving approximately a 0.3 OD signal for cholesterol versus approximately a 1 OD signal for serum protein and illustrates the need for front panel zero and gain adjustments.

Figure 8:
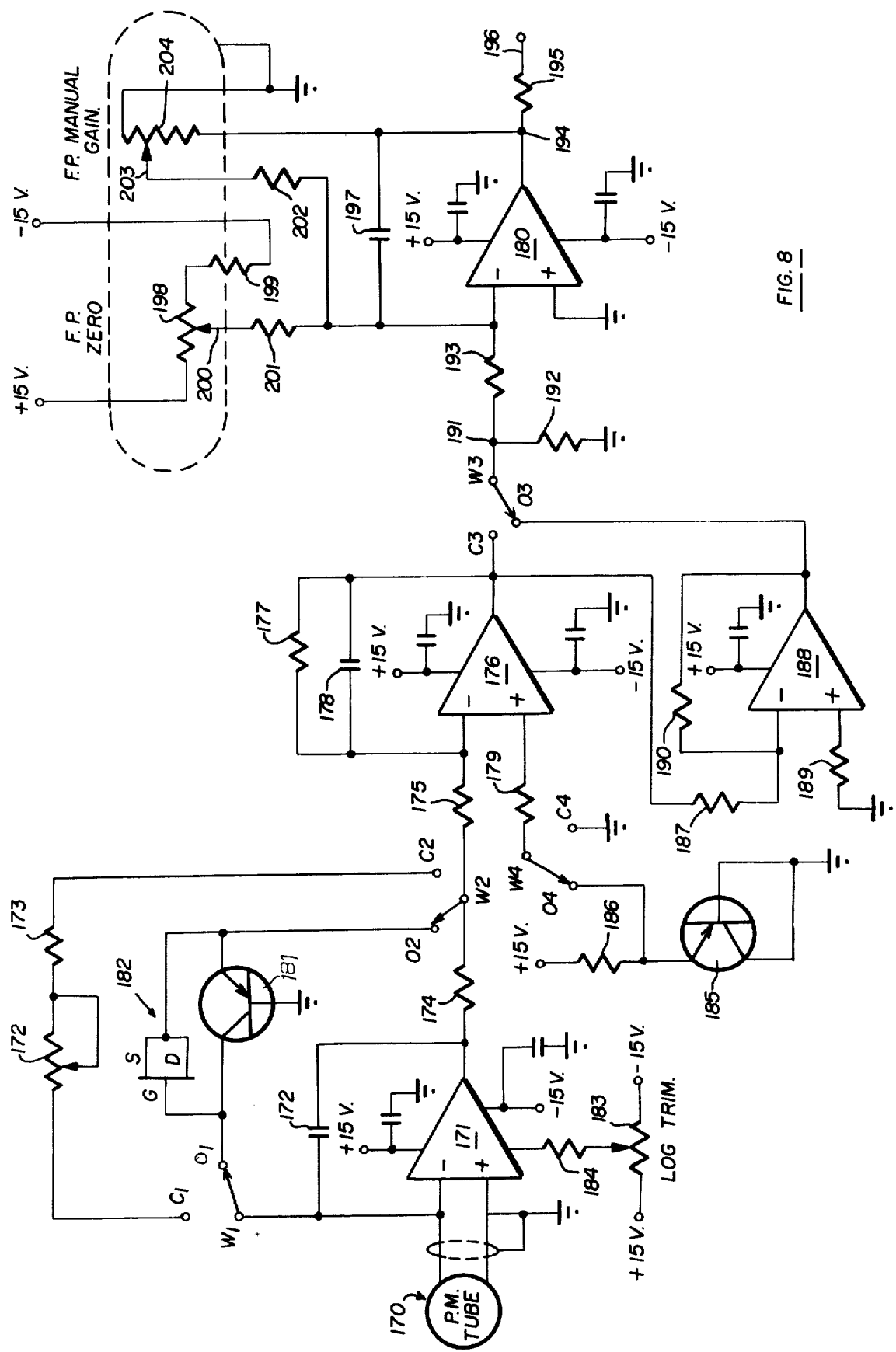
FIG. 8 is a schematic diagram of the initial amplifier stages in the amplifier chain from the photomultiplier tube of block 59 of FIG. 1.

The output of the control amplifier circuit of FIG. 8 is supplied via lead 196 to an input node 205 of the circuit of FIG. 9. Node 209 is connected through a resistor 206 to the non-inverting input of an operational amplifier 207 and the non-inverting input is also coupled to ground through a capacitor 208. The input node 205 is also connected through a capacitor 209 to a node 210 and node 210 is connected directly to the inverting input of the amplifier 207 and through a negative feedback path is connected directly to the output of the amplifier 207.

The stage of the amplifier chain including amplifier 207 functions as a low pass active filter. The cutoff frequency is set at approximately 20 Hertz by the values of resistors 195, 206 and capacitors 208 and 209. This filter provides approximately 12 db of attenuation at the number 2 $F_c$ and a roll-off of 40 db per decade. The amplified and filtered signal present at the output of amplifier 207 is then applied to the Input IN of the Sample and Hold circuitry of the dotted block 211.

The function of the sample and hold circuit of block 211 is to sample the input signal at the IN input under microprocessor control dictated by the LOGIC signal on lead 155 from the CB2 output of PIA 132 of FIG. 7 as previously described. The sample and hold circuitry may be, for example, a conventional LF398 unit which is commercially available. The signal from the output of the low pass filter amplifier 207 is supplied to the IN input and then applied to the non-inverting input of an operational amplifier 212 whose inverting input is connected directly to the output of a buffer amplifier 213. The output of the amplifier 212 is connected to a normally open switch arm 214 which may be controlled to close the switch arm 214 on a switch contact 215 to establish a circuit path between the output of the input amplifier 212 and both the input of the buffer amplifier 213 and one plate of a polycarbonate charging capacitor 216. The closure of the switch arm 214 is controlled by the signal output represented by the dotted line 217 from the amplifier 218 whose input is the signal LOGIC from lead 155 as previously described. The output terminal of the sample and hold circuit of block 211 is taken from the output of buffer amplifier 213 and the signal OUT is supplied to the non-inverting input of an operational amplifier 219 which is configured as a comparator.

The function of the sample and hold circuit of block 211 is to sample the signal present at the IN input from the output of the previous low pass filter stage. This is done under microprocessor control via the CB2 output from the PIA 132 of FIG. 7. The arrival of a CB2 signal at the LOGIC input closes the switching element 214 on switch contact 215 and allows buffer amplifier 212 to charge the capacitor 216 to the input signal level. When the signal from the CB2 output on lead 155 goes low, the circuit of block 211 will go into a hold state. The hold state disconnects the input and allows the output to be maintained at its present level which is the level to which the charge holding capacitor 216 was charged prior to the opening of the switch 214. Since the analog signal arriving from the low pass filter stage including amplifier 207 is constantly changing at a rate faster than the digitizing rate of 750 samples per second, it is desired to hold the analog signal until it is digitized. The input signal is stored on the capacitor 216 which is a polycarbonate low leakage capacitor and the stored signal is then provided as the positive input to a comparator 219.

The comparator 219 is in a feedback path from the analog-to-digital converter or DAC 134. The non-inverting input of the comparator 219 receives the "held" signal from the output of buffer amplifier 213 which is that signal held or preserved on the capacitor 216 while the switch 214 is opened to prevent receipt of the analog signal at the IN input. The inverting input of comparator 219 is supplied via lead 167 from the AOL output of the DAC 134 of FIG. 7. The output of the comparator 219 is translated to TTL logic levels for the PIA input at PBO by a transistor 220 and the microprocessor 30 uses the signal at the PBO input of PIA 132 to find out if its last output at the DAC 134 was above or below the input signal level presented to the comparator 219 by the sample and hold circuit 211.

The output of the comparator 219 is connected to the base electrode of transistor 220 through a resistor 221. The emitter electrode of transistor 220 is connected to ground and a diode 222 is connected such its anode is connected to ground and its cathode connected to the base of transistor 220. The collector of transistor 220 is connected via a pull-up resistor 223 to a +5 volt source of potential and via lead 156 is supplied to the PBO input of the PIA 132 as previously described.

When the comparison-conversion operation begins, the most significant bit of the DAC 134 is set for a one-half scale output. The output of the comparator 219 is then checked and if the DAC output on lead 167 is higher than the sampled signal from the output of buffer amplifier 213, the output of the comparator 219 will be low. With the low at the output of comparator 219, transistor 220 will remain in a non-conducting state and the +5 volt high signal will be applied to the PBO output of PIA 132 via resistor 222 and lead 156. The processor 30 will respond to this high signal and set the most significant bit low and the next most significant bit at input B10 high for another cycle.

If, on the other hand, the output of the level translator comprising transistor 220, pull-up resistor 223, and the +5 volt source of potential was low, indicating that the AOL output of the DAC 134 was below the value of the sampled signal, then the processor 30 will leave the most significant bit B11 set high and set the next most significant bit B10 high for the next cycle. This process continues until all bits or inputs of the DAC 134 have been utilized. At this point in time, the processor 30 will have a 12 bit word representative of the input signal level at the sample and hold output to an accuracy of ±½ LSB. The microprocessor 30 then transfers this information via the data bus 36 to the RAM memory of FIG. 4 and another sampling cycle is started as the CB2 output of the PIA 132 will again go high and this high will be supplied via lead 155 to the LOGIC input of amplifier 218 to close the switch 214 and begin the sampling cycle again.

During the scan sequence, the input routine is performed at a rate determined by the timer of block 65 of FIG. 10 which serves as a sample clock. The sample clock 65 is a conventional IC timer, such as the standard 1455 used in a free-running or astable mode of operation. The frequency of this sample clock may be controlled by varying the trimpot resistor 224 and the ouput of the clock 65 is applied to the input CA1 of the PIA 132 via lead 151. In the preferred embodiment of the presnet invention, the clock output is set for 700 HZ.

The K1 relay operation will now be described with reference to the circuit of FIG. 13. Lead 149 supplies a signal from CA2 output of PIA 131 of FIG. 7 to the base of a transistor 225. The base of transistor 225 is also connected to a +5 volt source of potential through a resistor 226. The emitter of transistor 225 is grounded and the collector is connected to one end of a relay coil K1 whose opposite terminal is connected to a +12 volt source of potential. A diode 227 is connected in parallel across the relay coil K1 and has its anode connected to the collector of transistor 225 and its cathode connected to the +12 volt source. In the log mode of operation, the relay K1 is energized by a high CA2 signal from the PIA 131. A high signal turns on the transistor 225 and energizes the relay coil K1 since current is allowed to flow through the coil when a conductive path is established from the +12 volt source through the coil and the conducting transistor 225 to ground. The diode 226 clamps the inductive kick of the coil to about +12 volts when the coil K1 is de-energized thereby protecting the transistor 225 from damage due to an abnormally high collector-to-emitter voltage.

The level translator transistor 220 of FIG. 9 has its base current limited by the resistor 221 and a reverse bias clamp effected by diode 222 prevents damage to the transistor 220 during negative excursions of the output of the comparator 219. The collector transistor 220 is pulled up to 5 volts by resistor 223 so that the device 220 is used as a current switch.

As stated previously, the vertical DAC 134 of FIG. 7 is used for vertical deflection of the recorder of block 50 and the oscilloscope of block 48. The solid state switch represented by block 153 of FIG. 9 is used to provide the required switching between the recorder and oscilloscope routings. The solid state switch 153 may be a conventional switching device such as a standard AD 7512 and the switch is controlled by the CA2 output of PIA 132 which is supplied via lead 152 to the control input CONT of the switch 153. A high signal at the CONT input of the solid state switch 153 will switch the vertical signal from the AOL output of the DAC 134 which is supplied via lead 167 to the IN input from the normally closed contact which supplies the input signal to the recorder circuitry to the normally open contact which supplies the signal to the oscilloscope circuitry.

The normally open contact of the solid state switch 153 is connected to one terminal of a resistor 231 whose opposite terminal is connected directly to the non-inverting input of an operational amplifier 232. The non-inverting input of amplifier 232 is also connected to ground through a resistor 233. The inverting input of amplifier 232 is connected directly to the output via a negative feedpath and the output is supplied via lead 234 which transmits the vertical deflection signal VERT to the oscilloscope circuitry of block 48 to be hereinafter described.

Similarly, the normally closed contact of the solid state switch 153 is connected to one terminal of a resistor 235 whose opposite terminal is connected directly to the non-inverting input of an operational amplifier 236. The non-inverting input of amplifier 236 is also connected to ground through a resistor 237. The inverting input of amplifier 236 is connected directly to its output via a negative feedback path and the output is supplied via lead 238 to the recorder circuitry of block 50 for use as hereinafter described.

Therefore, whenever a high signal appears at the control input of the solid state switch 153, the AOL signal from the DAC 134 will be supplied to the oscilloscope buffer 232 and whenever a low signal is supplied to the control input of the solid state switch 153, the input signal will be supplied to the recorder buffer 236. The recorder buffer 236 is a unity gain non-inverting amplifier. The input signals reduce to about one-third its normal level by the resistors 235, 237 and the signal is delivered to the recorder via lead 238. The scope buffer 232 is the same configuration but has a higher input attenuation as determined by the value of the resistors 231 and 233, as conventionally known.

The PB1 output of the PIA 132 of FIG. 7 is supplied via lead 157 to the Event Marker circuit of FIG. 14. Lead 157 supplies the PB1 signal to the base electrode of a transistor 239 through a resistor 240. The transistor 239 has its emitter connected directly to ground its cathode connected through a pull-up resistor 242 to a +12 volt source of potential. The collector of transistor 239 is also supplied through a capacitor 242 to a node 234. Node 234 is connected to ground through a resistor 244 and is also connected to the anode of a diode 245 whose cathode supplies the EVENT MARKER or fraction boundary signal to the recorder circuitry of block 50 via lead 246.

As previously described, the output of the PIA 132 of FIG. 7 labeled PB3 is used by the recorder circuitry as a High Heat enable signal and this signal is delivered to the recorder of block 50 via lead 158. The normal level at PB3 is low and it is brought high at those times at which the processor 30 commands high heat. The CB1 input is the graph length control input. This input clock sets the data presentation rate during a graphical reproduction sequence on the recorder such that the more rapid the input pulses, the shorter the graph. The rate is controlled by a front panel control on the recorder, as conventionally known, and is delivered to the recorder via lead 154.

The input CB1 of the PIA 131 of FIG. 7 is for the oscilloscope curser. The input on lead 147 is the output of an operational amplifier comparator and requires level translation to +5 volts by transistor 145. Transistor 145 has its base current limited by a resistor at the output of the operational comparator and negative signals are clamped by the diode 146. The output from the switch circuit of transistor 135 is at the collector which is pulled up to +5 volts by the resistor 144 to supply the signal to the CB1 input.

The CRT or oscilloscope and associated circuitry represented by block 48 of FIG. 1 will now be described in detail with reference to FIGS. 15 and 16. The oscilloscope or "scope" enables the user of the microprocessor-controlled densitometer of the present invention to view the scan or trace prior to committing it to a graphical output. The vertical deflection information is developed on the PIA 132 and the DAC 134 of FIG. 7 while the horizontal signal is developed by the PIA 131 and its dedicated DAC 133 under control of the microprocessor 30, as previously described. The circuits of FIGS. 15 and 16 require a ±15 volt DC supply and a +180 volt DC supply which are conventionally known and not described herein. The scope control circuitry of FIGS. 15 and 16 include a horizontal deflection circuit, a cursor position circuit, a vertical deflection circuit, CRT control circuitry and the cathode ray tube or CRT itself. An additional power supply of −3 kv is also conventional and not shown but is used to supply the necessary high voltage signal to the CRT.

The cathode ray tube or CRT 250, as its name implies, functions by the cathode emitting a ray or beam of electrons directed toward the front surface or face (anode) of the CRT. This electron beam is subjected to the effects of various focusing electrodes after leaving the cathode to enable the user to control the focus of the beam on the face of the tube. Before the beam leaves the neck of the tube it also passes between the horizontal and the vertical deflection plate pairs X1, X2 and Y1 and Y2, respectively, allowing two axis control over the beam's position on the face of the tube. The electron beam accelerates toward the face of the CRT since it is more positively charged than the cathode and due to the effect of the accelerating element. When the electron beam strikes the face of the CRT, the phosphor coating at the point of impact becomes excited and emits photons or light. The beam current is then returned back through the phosphor coating and along the inside of the tube envelope by a conductive coating or aquadag to the anode connection. In the preferred embodiment of the present invention, the CRT 250 is a conventional, commercially available unit such as an Amperex D14-251 GM.

The horizontal deflection circuit of FIG. 11 includes, in the preferred embodiment of the present invention, two conventional 741 operational amplifiers 251 and 252 in a dual package and a cascode circuit referred to generally by the reference numeral 253. The horizontal signal HORIZ is supplied to an input node 254 via lead 141 from the AOL output of the DAC 133 of FIG. 7 as previously described. Node 254 is connected through a resistor 255 to the inverting input of the operational amplifier 251 while the non-inverting input is connected to ground through a resistor 256. Negative feedback is provided between the output of the amplifier 251 taken from the node 257 and the inverting input via a negative feedback path allowing horizontal gain control and input offset control. The feedback path includes a first series resistor 258 having one terminal connected directly to the inverting input of the amplifier 251 and its opposite terminal connected to a horizontal gain control trim resistor 259. The opposite terminal of the gain control trim resistor 259 is connected directly to the output node 257. A second feedback path is connected in parallel with resistors 258 and 259 and includes a capacitor 260 having a first plate connected to the inverting input terminal and its opposite plate connected to a variable arm or tap 261 whose position can be controlled by a front panel horizontal gain control knob or the like. The opposite plate of capacitor 260 is also connected directly to the second terminal of the trim resistor 259 and the output node 257.

Another portion of the negative feedback circuit associated with amplifier 251 includes an input offset trim resistor 262 having one terminal connected to a −15 volt source of potential through a resistor 263 and its opposite terminal connected to ground through a resistor 264. A positionable potentiometer or trim arm member 265 can be positioned along the trim resistor 262 by a front panel adjustment member to control horizontal input offset and the arm 265 is positioned to control the amount of resistance in the circuit between the −15 volt supply and the inverting input of amplifier 251 and varies the feedback signal supplied by the series feedback resistors 258, 259 and the capacitor 260 as conventionally known.

The operational amplifier 251 and its associated feedback network functions as a variable gain stage controlled by the front panel horizontal gain control element with the minimum gain being set by the series resistor 258 in the feedback loop. High frequency attenuation is provided in this stage by the feedback capacitor 260 and the input signal as applied to the inverting terminal through an input resistor 255 which establishes the input impedance of the stage. The resistor 256 connecting the non-inverting terminal to ground serves to minimize the offset voltage effect. Input offset associated with the horizontal circuit is required due to the polarity of the horizontal ramp voltage represented by the signal HORIZ. This signal starts at about +10 volts and ramps down toward +5 volts as previously described. If the offset is not trimmed out, the DC level will cause the gain control to act as a position control as well. Therefore, adjustment of the offset control trim resistor 262 can be made such that the left hand side of the displayed oscilloscope scan remains stationary as the gain control knob is rotated.

The next stage which includes operational amplifier 252 acts as a position control circuit. It is basicly a differencing amplifier with a fixed gain as described below. The output from the first stage is supplied via output node 257 to the inverting input terminal of the amplifier 252 through a resistor 266. A negative feedback loop is established between the output node 267 of the amplifier 252 and the inverting input through a resistor 268. The non-inverting input to the amplifier 252 is connected to ground through a capacitor 269 and through a resistor 270 to an adjustable trim arm 271 which cooperates with a horizontal position adjustment trim resistor 272 as hereinafter described.

The amplifier 252 functions as a differencing amplifier with fixed gain and the voltage gain is controlled by the ratio of the input resistor 266 to the feedback resistor 268. By controlling the applied DC level on the non-inverting input terminal, the DC output level may be shifted up or down as desired. This is done by the resistive divider network including position arm 271 and the trim resistor 272 via a front panel control adjustment and the RC low pass filter which includes resistor 270 and capacitor 269. The output of the differencing amplifier 52 and hence the output of the position control stage represented thereby is supplied from output node 267 to the cascode amplifier circuit represented by reference numeral 253.

The cascode amplifier circuit 253 produces the horizontal deflection voltage potentials required by the CRT 250 and the circuit is configured as follows. The output node 267 of the position control stage is connected through an input resistor 273 to the base electrode of a transistor 274 whose collector is connected directly to the emitter electrode of a second transistor 275. The base of transistor 275 is connected to a +15 volt source of potential through a resistor 276 and the collector is connected directly to the X2 deflection plate of the CRT 250 via lead 277. Simultaneously, the collector of transistor 275 is connected to one terminal of a resistor 278 whose opposite terminal is connected to one terminal of a second resistor 279 whose opposite terminal is connected to the collector of an output transistor 280. The junction of resistors 278 and 279 is connected directly to a +180 volt source of potential.

The collector of transistor 280 is also connected via lead 281 to the X1 deflection plate of the CRT 250. The base of transmitter 280 is connected to a +15 volt source of potential through a resistor 282. The +15 volt source of potential is connected through a second resistor 283 and a third resistor 284 to ground. The junction of resistors 283 and 284 is connected through a resistor 285 to the base of a fourth transistor 286. The collector of transistor 286 is connected directly to the emitter of transistor 280 and the emitter of transistor 286 is connected to the emitter of transistor 274 to a resistor 287. Another path in parallel with the resistor 287 includes a resistor 288 and a normally opened switch assembly 289 which can be closed to complete the parallel path between the emitters of transistors 274 and 286 through resistor 288. A series combination of resistors 290 and 291 is also connected between the emitters of transistor 274 and 286 and the junction of resistors 290 and 291 is connected to a −15 volt source of potential.

The cascode amplifier 253 produces the horizontal deflection potentials X1, X2 required by the CRT 250. The driver transistor 274 effectively amplifies the emitter bias to the higher voltage output transistor 275 which is connected to its collector. The output transistor 275 has a fixed base bias such that as its emitter bias is varied by the lower transistor 274, a change in output voltage is seen on lead 277. The differential output between leads 277 and 281 is obtained by having a common emitter resistor network comprising resistors 287, 288 and 290, 291, as known in the art. This resistor network couples the input signals by the voltage across the common emitter resistor network which is developed by the collector currents of the drive side transistors 274, 275 through the resistor network. This applies emitter bias to the lower transistor 286 which has a fixed base bias. Once again, this will vary its conduction and the effective emitter bias applied to the upper output transistor 280 thereby changing the output voltage on lead 281. It should be noted that the emitter bias developed by the driver side comprising transistors 274 and 275 is the opposite phase with the output voltage of that side. Therefore, the non-driver side comprising transistors 286 and 280 receives an opposite polarity bias enabling the push-pull output voltage relationship characteristic of such cascode amplifier configurations.

It can be shown that the gain of this push-pull cascode amplifier is determined by the ratio between the output collector resistors 278 and 279 and the common emitter resistors 287, 288. Therefore, in the horizontal deflection circuit shown, the non-expanded gain is set to approximately 40 while the expanded mode voltage gain is set equal to approximately 99 by varying the effective common emitter resistor through the closure of switch 289.

FIG. 15 also shows a cursor position circuit which includes an operational amplifier 295 which acts as a comparator. The inverting input of the comparator 295 is connected through a resistor 296 to the horizontal input node 254 as previously described. The non-inverting input is connected through a positionable potentiometer arm or trim member 297 to control the amount of voltage supplied to the non-inverting input by selectively adjusting its position with respect to a cursor positioning trimming resistor 298. The trim resistor 298 has one terminal connected to a +15 volt source of potential through a resistor 299 and its opposite terminal connected to ground through a resistor 300. The negative supply input of the amplifier 295 is connected to a −15 volt source and through a capacitor 301 is connected to ground. A capacitor 302 is connected between ground and a positive supply node 303. Node 303 is connected to the +15 volt source of potential through a capacitor 304 which is connected directly to the positive supply input of the comparator 295. The positive supply node 303 is also connected to one terminal of the resistor 305 whose opposite terminal is connected to one terminal of the horizontal position trim resistor 272 and the opposite terminal of trim resistor 272 is connected through a resistor 306 to ground.

As previously stated, the positioning of the arm 271 with respect to the horizontal position trim resistor 272 controls the signal applied to the non-inverting input of amplifier 252. The output of the comparator or amplifier 295 is supplied from the cursor position control stage from the output of comparator 295 to supply the cursor position detection signal to switching transistor 145 of FIG. 7 via lead 147. As previously described, current switching transistor 145 controls the signal applied to the CB1 input of PIA 131 to supply cursor positional information to the microprocessor 30.

The opened loop gain configuration of the comparator circuit of amplifier 295 allows detection of very small input potentials. The inverting input of amplifier 295 has applied to it the horizontal ramp voltage by way of input node 254 through a current limiting resistor 296. The ramp voltage starts at +10 volts and ramps down to a +5 volts. The non-inverting terminal of the operational amplifier 295 has a variable voltage divider as a signal source which is variable from about 10.5 volts to 4.5 volts allowing for a variation range beyone that of the input ramp. If the cursor is in a normal operating position, the output of the comparator on lead 147 will be at the negative rail during the start of the horizontal sweep. As the horizontal ramp passes the applied voltage of the cursor position divider, the output of comparator 295 will switch to the positive rail signaling the processor system of the cursor position.

The vertical deflection control circuitry of FIG. 16 is virtually identical to the circuitry of FIG. 15 and operates in an identical manner except for the absence of a cursor position stage. Due to the similar nature of the two circuits, neither the structure nor the operation will be discussed in detail and corresponding components of the two circuits bear corresponding reference numerals with the reference numerals of the vertical deflection circuitry being one number higher in the hundredths position. For example, the amplifiers 251 and 252 of the horizontal deflection circuit of FIG. 15 are comparable to the amplifiers 351 and 352 of the vertical deflection circuitry of FIG. 16. There is, of course, no input offset circuitry and no expanded mode switch associated with the circuitry of FIG. 16.

The high voltage supply control circuitry for the CRT 250 will now be described with reference to FIG. 16. The −15 volt source of potential is connected to ground through a capacitor 311; is connected directly to the negative power supply input of operational amplifier 312; and is connected through a resistor 313 to a node 314. Node 314 is connected to one terminal of a high voltage adjustment trim resistor 315 whose opposite terminal is connected through a resistor 316 to ground. A zener diode 317 is connected between node 314 and ground and in parallel with the series combination of trim resistor 315 and resistor 316. The anode of the zener diode 317 is connected directly to node 314 while the cathode is connected to ground.

The inverting input of amplifier 312 receives a variable input signal from the positionable arm member 318 which can be selectively adjusted along trim resistor 315 to vary the signal applied to the inverting input of amplifier 312. The non-inverting input of amplifier 312 is connected to ground through a resistor 319 and the ungrounded terminal of resistor 319 is connected to the output of amplifier 312 through a capacitor 320. The output of amplifier 312 is also connected directly to the base electrode of a series pass transistor (Darlington pair) 321. The collector of transistor 321 is connected to ground through a capacitor 322 and the emitter is connected to a node 323. A −22 volt source of potential is connected to the collector of transistor 321 through an inductance coil 324. Node 323 is connected directly to the negative input of a conventional DC-to-DC converter 325 while its positive input is connected to ground. A capacitor 326 is connected between the negative and positive inputs of the DC-to-DC converter 325. The negative output of the DC-to-DC converter 325 is taken from output node 310 and node 310 is connected to a resistor 327 and a second resistor 319 to ground. The junction of resistors 319 and 327 is connected back to the non-inverting input of the amplifier 312.

The high voltage power supply described above produces a negative 2.5 kilovolt signal at its output. The supply includes a zenered reference including resistors 313,315 and 316 and the zener diode 317, an error or differencing amplifier 312, a compensation capacitor 320, series pass transistor 321, an input filter comprising capacitors 322 and 326, an intermediate filter capacitor 320 a DC-to-DC converter 325 and an output divider network comprising resistors 327,328. The output voltage of the DC-to-DC converter 325 is divided down by the voltage divider resistor combination 327,328 to a level compatible with the inverting input of the comparator 312. This signal is applied to the inverting input and a reference voltage is derived from a zener voltage divider network comprising resistors 313,315 and 316 and zener diode 317. This adjustable voltage level supplied to the non-inverting input of amplifier 312 so that if a difference exists between the two input levels of the comparator 312, the comparator will compensate by either increasing or decreasing the base drive to the series pass transistor 321 for a corresponding change in the output voltage of the DC-to-DC converter 325. The filter comprising capacitors 322 and 326 serves to decouple the switching transients associated with the DC-to-DC converter 325 and the filter capacitor 326 aids in stabilizing the input voltage of the converter 325. A feedback capacitor 320 aids in slowing the regulator down by developing a negative feedback in the loop for transients and high frequency noise. The output of this voltage power supply is supplied to a resistive divider network for providing the conventional CRT controls as hereinafter described.

As previously described, the high voltage power supply develops a 2.5 KV signal at its output and therefore a 2.5 KV signal between the positive and negative outputs of the DC-to-DC converter 325. The positive output of the converter 325 is connected directly to a voltage divider node 329. Node 329 is connected to one terminal of a trim resistor 330 whose opposite terminal is connected to a +180 volt source of potential. The trim resistor 330 is used as the astigmatism control for the CRT 250 and the controlled voltage is supplied via positionable arm or voltage tap member 331 and lead 332 to the designated electrodes of the CRT 250 shown in FIG. 15.

Node 329 is also connected through a resistor 333 to one terminal of a focus trim resistor 334 whose opposite terminal is connected through a resistor 335 to a node 336. The focus control signal is supplied via adjustable potentiometer arm or trim member 337 and lead 338 to the appropriately labeled electrode of the CRT 250.

Node 336 is connected directly to an output lead 339 which is connected to the appropriately designated electrode of the CRT 250 of FIG. 15 and node 336 is also connected through a resistor 340 and a lead 341 to the CRT 250. Node 336 is further connected through a resistor 342 to one terminal of an intensity trim resistor 343 whose opposite terminal is connected through the resistor 328 to the negative converter output node 326 previously described. The intensity control is provided by selectively positioning the arm member 344 along the trim resistor 343 to vary the voltage supplied via lead 345 to the intensity control electrode of the CRT 250 of FIG. 15.

The CRT controls are conventional but will be briefly described as follows. The intensity and focus electrodes as well as the cathode witin the CRT derive their control voltage from the resistive divider across the outputs of the high voltage supply. The astigmatism control derives its voltage from the +180 volt supply by means of a potentiometer 330. The 6.3 VAC filament winding of the CRT 250 is floated to the high voltage supply through the resistor 340 via lead 341 to decrease the internal arcing possibility between the interfilament and the cathoe. The intensity control provided by resistor 343 is the most negative of the applied voltages and this potential is applied to the grid electrode to repel some of the electrons formed in the space charge surrounding the cathode of the tube 250 thus preventing them from becoming part of the electron beam.

The cathode of the CRT is the next most negative and acts as a source of free electrons for beam formation by way of thermionic emission when heated by the filament. The focus control provided by resistor 334 is the next most negative and is applied to elements within the tube which enable the beam to be focused or brought to a point on the face of the CRT. The astigmatism control potentiometer 330 varies a positive voltage applied to elements in the tube which also act as focusing elements as well as accelerators for the electron beam and provide a return path to ground for the electron beam. The vertical deflection signals are provided to the Y1 plate and the Y2 plate from the outputs of the cascode amplifier circuit of FIG. 16 via lead 377 and 381, respectively.

The CRT or oscilloscope 250 of FIG. 15 is a conventional, commercially available unit and the controls are conventional as well. The most important feature of the oscilloscope 250 for the purposes of the present invention is its capacity to display a continually refreshed curve or waveform trace representing the scanned optical density pattern and as the cursor is moved manually from either left or right, its position is detected and the system software will cause the cursor to move up and down along the trace printed on the scope for addressing particular points along the trace for inspection and operator-editing purposes as hereinafter described.

The recorder and associated pen driver circuitry of block 50 will now be described with reference to FIG. 17, 18 and 19. The recorder system enables the user of the densitometer of the present invention to produce a permanent record of the approved or edited scanned pattern. The reproduction of the pattern is made up of two section, (1) the analog trace of the pattern which is drawn on the grid pattern of the chart paper itself, and (2) a second section which includes the printed information along the clear track at the bottom of the chart paper. An attempt has been made in the design of the present recorder to isolate the two sections or functions such that the printer section will be described hereinafter while the analog or pen deflection-heat control section is described below. The recorder circuitry of FIGS. 17, 18 and 19 includes a pen servo motor deflection circuit, a chart length clock, a chart length motor control circuit, and a pen heat control circuit. Two voltage regulator circuits are also discussed with a +15 volt DC supply for these analog circuits. The microprocessor 30 upon receiving a command to "Draw" will first go through an output routine which sets the sample and hold circuit via the signal SAMPLE from the PB1 output of PIA 136 of FIG. 16 via lead 351. PIA 136 also supplies the signal $\overline{\text{CHART ON}}$ from the CA2 output on lead 252 as hereinafter described.

Figure 17:
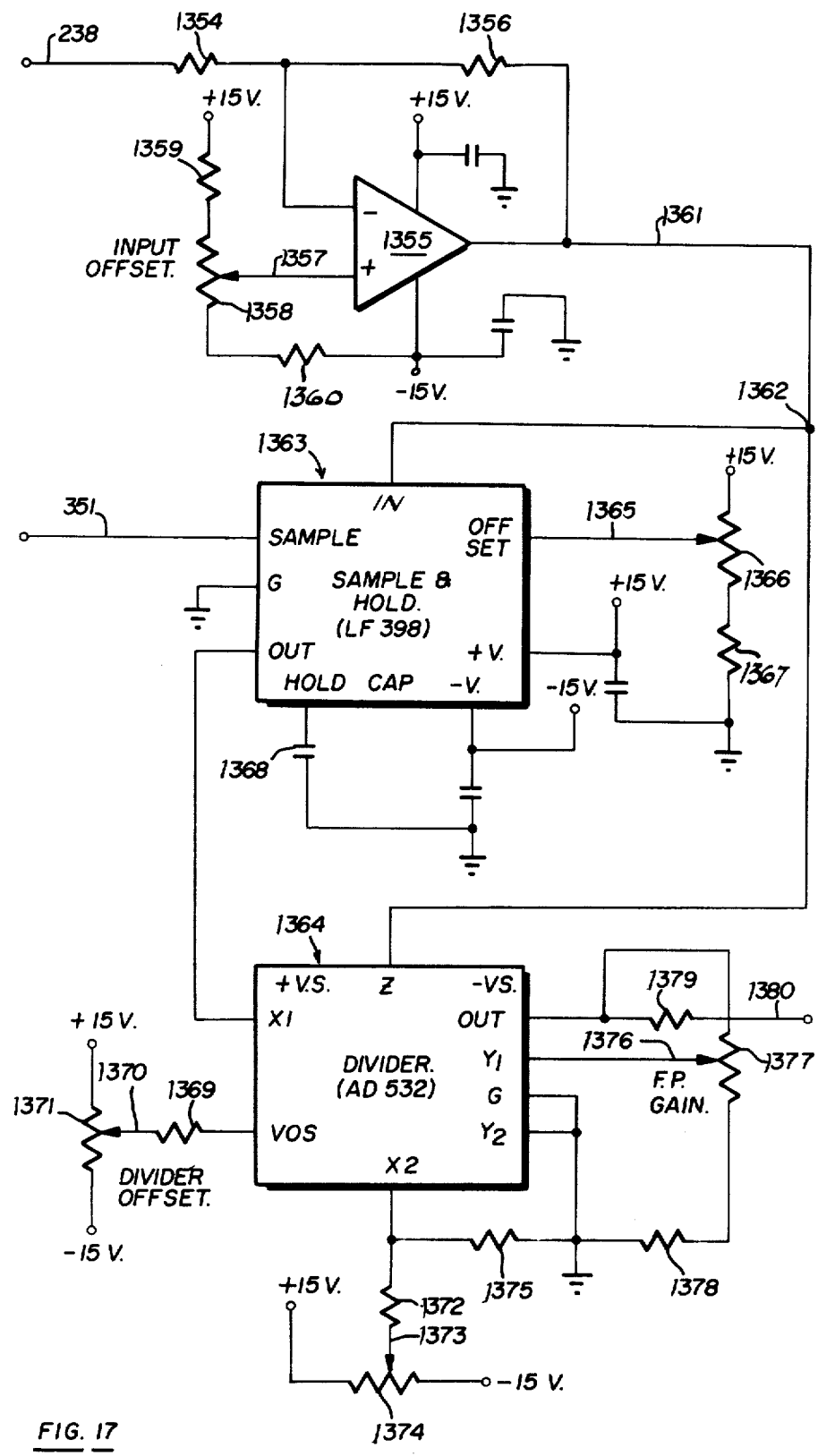
FIG. 17 is a schematic diagram of a portion of the pen control circuitry associated with the recorder of block 50 of FIG. 1.

The vertical deflection signal VERT from the output of amplifer 236 of FIG. 9 is supplied via lead 238 to the circuit of FIG. 17 and supplied through a resistor 1354 to the inverting input of an operational amplifier 1355. The inverting input of amplifier 1355 is also provided with a negative feedback path via a resistor 1356 which connects the output of the amplifier 1355 back to the inverting input. The non-inverting input of amplifier 1355 is used for selectively controlling input offset and is connected through a positionable potentiometer arm member or trim tap 1357 which adjustably controls the voltage applied to the non-inverting input by its position with respect to the trim resistor or potentiometer 1358. Resistor 1358 has one terminal connected to a +15 volt source of potential to a resistor 1356 and its opposite terminal connected to a −15 volts source of potential through a resistor 1360.

The output of amplifier 1355 is supplied via lead 1361 to an output node 1362. The node 1362 is connected directly to the IN input of a Sample and Hold circuit 1363 and directly to the Z input to an analog divider circuit 1364. The sample and hold circuit 1363 is, in the preferred embodiment of the present invention, a conventional unit such as a standard LF398 sample and hold module. The SAMPLE input of the circuit 1363 is connected via lead 351 to the PB1 output of PIA 136 of FIG. 20 as hereinafter described. The offset input of the sample and hold circuit 1363 is connected through a positionable arm element 1365 to selectively tap a variable amount of resistance and hence a selectible offset voltage via the sample and hold offset trim resistor or potentiometer 1366. Resistor 1366 has one terminal connected directly to a +15 volt source of potential and its opposite terminal connected to ground through a resistor 1367. The charge-holding capacitor 1368 is connected between the HOLD input and ground while the OUT output of the sample and hold circuit 1363 is connected to the X1 input of the analog divider circuit 1364.

In the preferred embodiment of the present invention, the analog divider circuit 1364 is a conventional divider such as a standard AD 532 divider module which is commercially available. The divider 1364 has its VOS input connected through a resistor 1369 to a positionable voltage tap arm 370 which can be adjustably positioned to control the voltage supplied to the VOS input by selectively positioning the arm 1370 along the potentiometer 371. Potentiometer 1371 is connected between a +15 volt source of potential and a −15 volt source of potential and is used to provide the offset voltage for the divider. The X2 input is connected through a resistor 1372 and a potentiometer arm 1373 to selectively adjust the voltage applied to the X2 input by adjusting the value of the voltage applied via a trim resistor or potentiometer 1374. Resistor 1374 is connected between the +15 volt and −15 volt sources of potential. The X2 output is also connected to ground through a resistor 1375. The Y1 output is supplied with a front panel gain adjustment through a potentiometer arm 1376 which can be adjusted along a potentiometer or variable resistor 1377. Resistor 1377 has one terminal connected directly to the OUT output of the divider 1364 and its opposite terminal connected to ground through a resistor 1378. The OUT output of the divider 1364 is connected through a resistor 1379 to supply the output signal to the circuit of FIG. 18 via electrical lead 1380.

Figure 18:
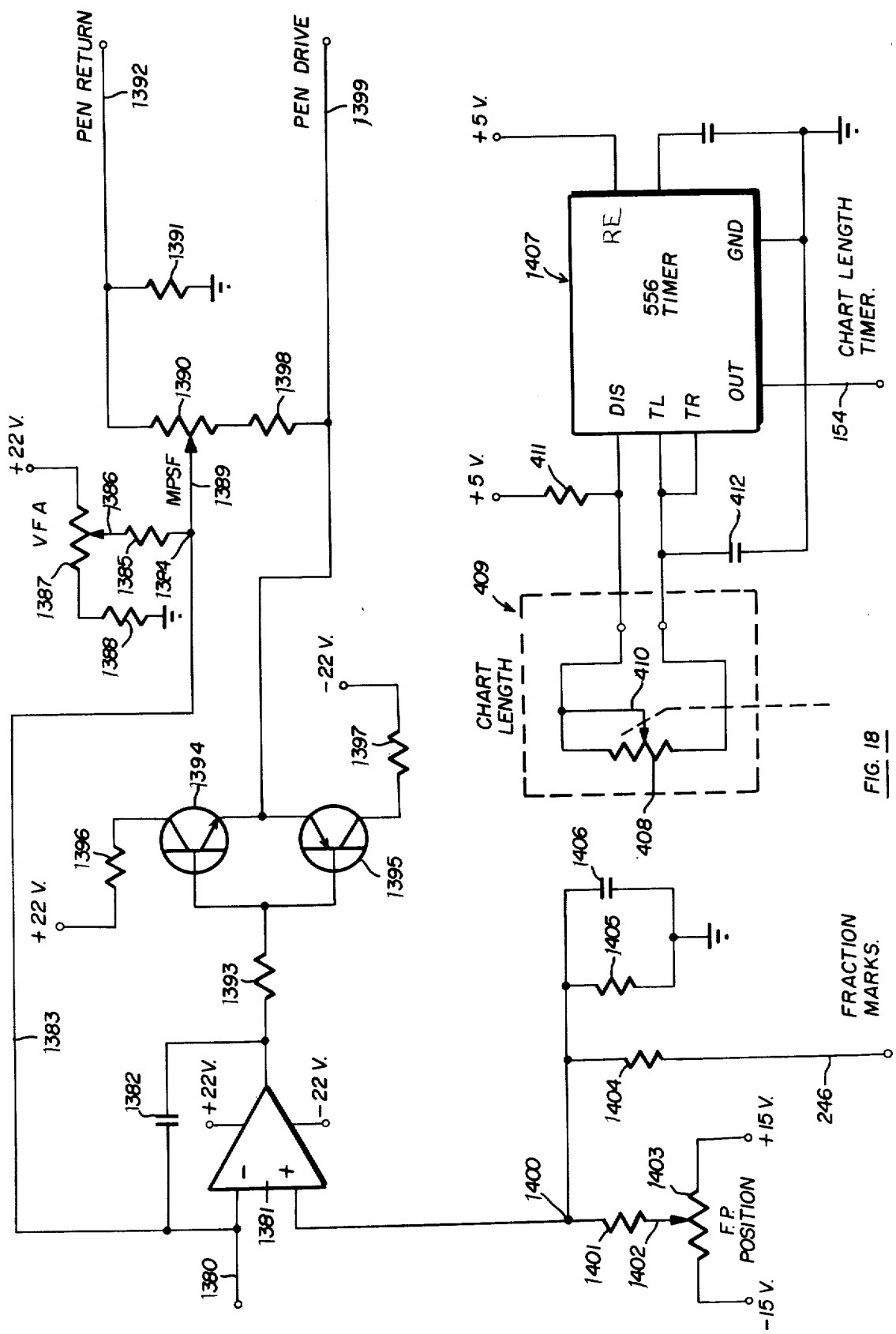
FIG. 18 is an electrical schematic diagram of another portion of the pen driver circuitry and chart length control circuitry of the recorder of block 50 of FIG. 1.

The output of the divider module 1364 is supplied via resistor 1379 and lead 1380 to the negative input of an operational amplifier 1381 of FIG. 18. A capacitor 1382 is connected in a feedback loop across the amplifier 1381 from the amplifier output back to the inverting input. The inverting input of amplifier 1381 is also connected via lead 1383 to a node 1384. Node 1384 is connected through a resistor 1385 and an adjustable potentiometer arm 1386 to select an adjustable voltage VFA via a variable resistor or potentiometer element 1387. The resistor 1387 has one terminal connected directly to a +22 volt source of potential and its opposite terminal connected to ground through a resistor 1388. Node 1384 is also connected via an adjustable potentiometer tap 1389 to vary the signal MPFS supplied from a potentiometer or variable resistor element 1390. The potentiometer 1390 has its first terminal connected to ground through a resistor 1391 and is used to supply the "Pen Return" signal to a conventional pen driver via lead 1392.

The output of the operational amplifier 1381 is also connected through a resistor 1393 to the base electrode of a first NPN transistor 1394 and a second PNP transistor 1395. The first transistor 1394 has its collector connected to a +22 volt source of potential through a resistor 1396 and the second transistor 1395 has its collector connected to a −22 volt source of potential through a resistor 1397. The emitters of the resistors 1394 and 1395 are commonly connected together and their junction is connected to the second terminal of resistor 1390 through a resistor 1398 and used to supply the PEN drive signal to conventional pen drive circuitry via lead 1399.

The non-inverting input of operational amplifier 1381 is connected to an input node 1400. Node 1400 is connected through a resistor 1401 to a potentiometer arm 1402 which controls the value of the voltage signal applied to node 1400 through a front panel position adjustment potentiometer or variable resistor 1403. Resistor 1403 has one terminal connected to the −15 volt source of potential and its oposite terminal connected directly to the +15 volt source of potential. Node 1400 is also connected through a resistor 1404 to receive the Fraction Boundary or Event Markers generated by the circuit of FIG. 14 via lead 246 as previously described. Lastly, node 1400 is connected to ground through the parallel combination of a resistor 1405 and a capacitor 1406.

Figure 20:
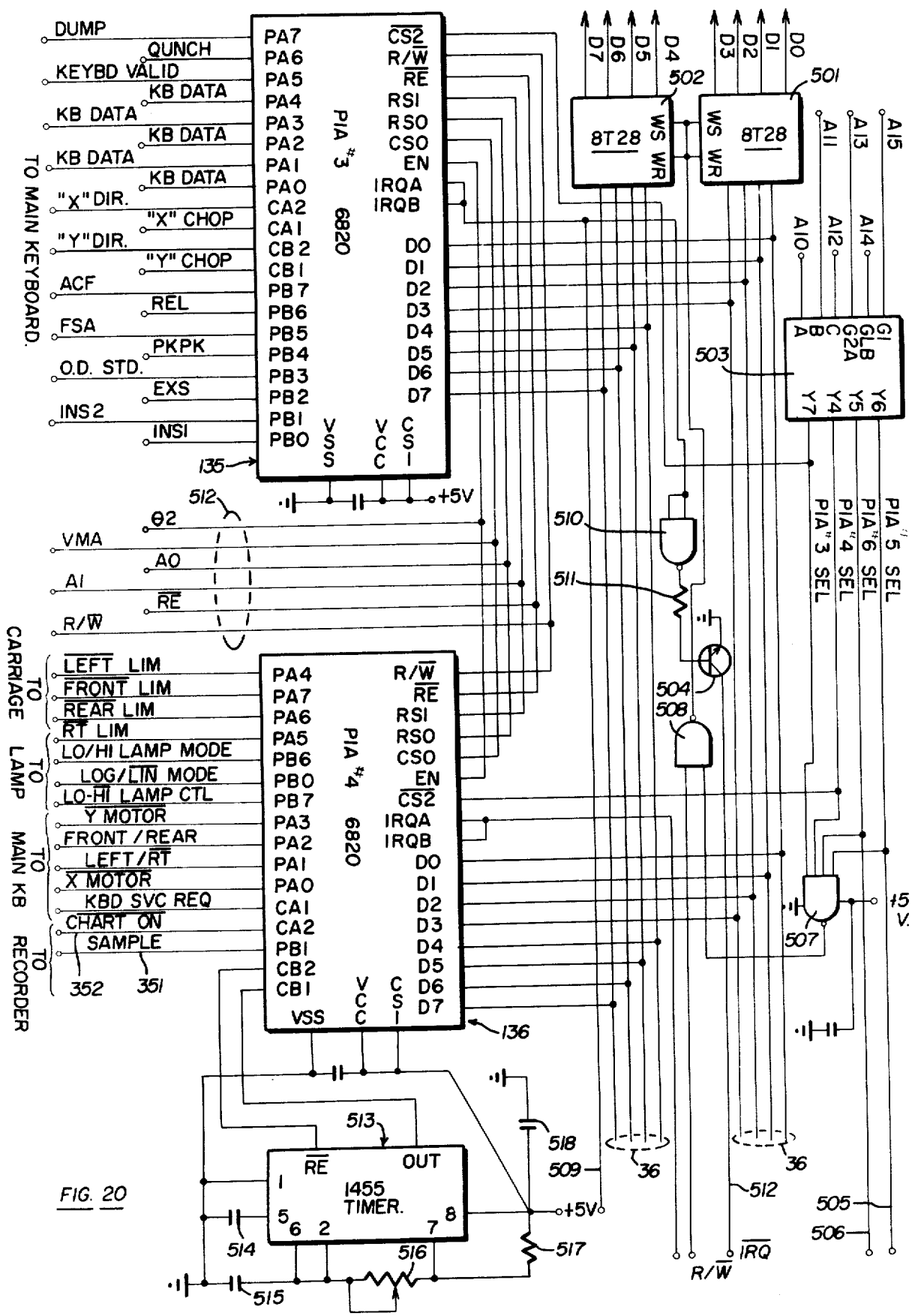
FIG. 20 is a detailed block diagram of still another portion of the PIA circuitry of block 34 and the I/O circuitry of block 46 of FIG. 1.

As previously stated, the microprocessor 30, upon receiving a command to "DRAW", will first go through an output routine which sets the sample and hold circuit 1363 via the signal SAMPLE which is outputted via lead 351 from the PB1 output of PIA of FIG. 20. The presence of this signal will cause the sample and hold circuit 1363 to hold the full scale value to which the analog trace is to be scaled. The microprocessor 30 will then start the chart motor and enable the high heat boost circuit for a short period of time. Then the data points are output from the vertical DAC 134 of FIG. 7 at the rate determined by the chart length timer 1407, as hereinafter described, and the required information is printed at the bottom of the chart proximate the appropriate graphical trace to which it pertains.

The analog input to the circuit of FIG. 17 is supplied via lead 238 from the output of amplifier 236 of FIG. 9 and represents the vertical deflection information diverted to the recorder as opposed; to the oscilloscope. The operational amplifier 1355 is an inverting buffer which amplifies the analog input signal with a voltage pin of approximately 3 set by the ratio of resistor 1356 to resistor 1354. The non-inverting terminal of amplifier 1355 is used as an offset adjustment by having a constant adjustable DC level applied thereto. This level is obtained from an adjustable voltage divider made up of resistors 1358, 1359 and 1360 between the positive and negative 15 volt supplies. The output of the amplifier 1355 is applied to two devices,(1)the sample and hold circuit 1363 and(2)the analog divider module 1634.

As stated, the microprocessor 30 puts out the full scale chart value and holds that value in the sample and hold circuit 1363. This allows the chart or graph plot to be scaled in amplitude to specific standards. The sample command applied to the SAMPLE input of the circuit of block 1363 via lead 1351 is referenced to digital ground. A polycarbonate charge holding capacitor 1368 is coupled to the HOLD input of the sample and hold circuit of block 1363 and offset adjustment is provided by the potentiometer 1366 which can be used to adjust the output swing to full scale value under test conditions.

The actual scaling of the analog trace is done by the divider module 1364. The full scale value is applied to the X1 input and from the output of the sample and hold circuit 1363 and the amplified analog signal is supplied from the output of amplifier 1355 to the Z input of the divider 1364 via lead 1361 and node 1362. The mathematical function of the divider module 1364 is Z out $= -10Z/X$. The gain of the stage has been made variable about the preset or normal value by a feedback connection from the OUT output to the Y1 input via potentiometer 1377 and the front panel gain adjustment potentiometer element 1376. There are two offset adjustments associated with the divider module 1364. The first is connected to the VOS input and is associated with the offset produced when a low scale factor is presented to the X1 input and a zero signal is present at the Z input. When these conditions are present, this adjustment should make for a zero output. The other offset adjustments referred to as the "one volt adjust". This adjustment is to be made when the scale factor and input are low values but equal to a full scale output of ten volts. These adjustments are to be made with the front panel gain set to a minimum. The adjustment of one offset will effect the other setting thus requiring rechecking. The output of the divider module is taken from the output OUT and applied to the input of a power operational amplifier 1381 of FIG. 18 via lead 1380. The power operational amplifier 1381 is, in the preferred embodiment of the present invention, a conventional device such as a standard MC1436.

The inverting input of the power amplifier 1381 acts as a running junction and has the analog input signal applied thereto via resistor 1379 and lead 1380. Also applied to the summing junction at the iverting input of amplifier 1381 is a main pen full scale MPFS value which establishes a gain of the output stage. This signal is supplied via the trim resistor combination of arm 1389 and resistor 1390. Another input to the summing junction at the input of amplifier 1381 is the velocity feedback adjustment VFA which is used to compensate the pen motor drive for fast signals and is taken from the trim resistor 1387 via element 1386, resistor 1385 and lead 1383. The non-inverting input of the power amplifier 1381 has as its inputs a front panel pen position adjustment signal from the adjustable resistor 1403 and the event or fraction mark signals outputted from the circuit of FIG. 9 via lead 246 through resistor 1404. The pen position control places a DC bias on the non-inverting input from a conventional voltage divider, not shown, but known in the art, on the actual recorder itself. Resistor 1401 affords a degree of isolation from the fractions marks network. Thus, with a DC offset introduced, the output will shift its DC level giving pen position control. The fraction marks are applied through the resistor 1404 from the Event Marker circuit of FIG. 14 as previously described with resistor 1404 and capacitor 1406 acting as a forming network for shaping the input pulse. The output of the power amplifier 1381 is applied to the output drives including transistor 1394 and 1395 to current limiting resistor 1393.

The Class B output stage formed by transistors 1394 and 1395 provide pen motor drive currents. Resistors 1396 and 1397 primarily reduce the power dissipation requirements of the transistors 1394 and 1395 at the zero pen position and full scale adjustment. The resistor 1398 aids in establishing a feedback poential to the gain control trimmer 1390 which provides the signal MPFS. Resistor 1391 also aids in establishing a feedback potential from the pen motor return currents forming a closed loop system.

To briefly summarize, the input analog signals are amplified approximately three times by the amplifier 1355 and the sample and hold circuitry of module 1363 holds the full scale value to which the graph is to be scaled while the divider circuit of module 1364 provides the necessary scaling capability by providing an output voltage equal to ten times the input voltage divided by the full scale factor. The operational amplifier 1381 and output transistors 1394 and 1395 form the output stage of the circuit and supply the required PEN RETURN and PEN DRIVE signals which control the actual pen movement, as known in the art.

The chart length timer or clock 1407 of FIG. 18 is, in the preferred embodiment of the present invention, one-half of a standard LM556 timer and is used to provide a variable period timing pulse from the microprocessor 30. This timing pulse is used to clock the rate at which the processor 30 outputs the graphical data. Therefore, a very wide range of control over the length of the graphic presentation is afforded to the user. The potentiometer-type resistor 408 which is shown within the dotted block 409 is used to represent a front panel chart length adjustment. The control arm 410 of the potentiometer 408 supplies the input signal to the DIS input of the timer 1407 and the DIS input is connected to a +5 volt source of potential through a resistor 411. The opposite end of resistor 408 is connected to the TL and TR inputs and through a timing capacitor 412 is coupled to ground. The output OUT of the timer 1407 provides the chart length clock period timing pulses to the CB1 input of PIA 132 of FIG. 14 via lead 154 as previously described. The chart length control resistor 408 and the timing capacitor 412 may be used to variably adjust the control resistor 408 and the timing capacitor 412 may be used to variably adjust the frequency of the timer. It should be noted that the chart length timer control of FIG. 18 is used with a conventional chart recorder having a gain potentiometer and a high pen heat control and a basic pen heat control is used to provide a degree of control over the pen heat levels as the chart length is varied. This feature is standard with most modern commercially available pen recorders and will not be described in detail herein.

The basic chart motor control circuitry and pen heat control circuitry will now be described with reference to the circuitry of FIG. 19. The Paper Advance Signal from the PA5 output of the horizontal PIA 131 is supplied via lead 148 to a node 420. Node 420 is connected to a +5 volt source of potential through a resistor 421; is connected to a node 422 through a diode poled such that its anode is connected to node 422 and its cathode is connected to node 420; and is connected directly to the non-inverting input of an operational amplifier 423. The operational amplifier 423 has its inverting input connected to a voltage divider node 424 which forms the junction of a first resistor 425 connected to ground and a second resistor 426 which is connected to a +5 volt source of potential. The operational amplifier 423 is configured to function as a conventional comparator and the comparator output is supplied through a resistor 427 to the cathode of a diode 428 whose anode is connected to a node 430.

The voltage divider node 424 also supplies a reference signal to the non-inverting input of the second operational amplifier 431 whose inverting input is connected directly to the node 422. The amplifier 431 is also configured as a conventional comparator and its output is connected directly to the anode of a diode 432 whose cathode supplies an output signal via lead 433 to gate the chart control triac as hereinafter described with respect to FIG. 29.

Lastly, reference node 424 is connected to the non-inverting input of a third operational amplifier 434 to supply the voltage divider reference thereto. The inverting input of amplifier 434 is connected through a resistor 435 to the reference node 424 and to the inverting input of comparator 423. The operational amplifier 434 has a negative feedback path from its output through a resistor 436 to node 430 and from there a loop is closed through a resistor 437 connected between the node 430 and the inverting input of the operational amplifier 434 such that the output node 430 serves as the output of buffer amplifier 434.

The signal $\overline{\text{CHART ON}}$ is supplied via lead 352 from the CA2 output of PIA 136 of FIG. 20 as hereinafter described and lead 352 supplies the signal to node 422 through a diode 418 poled with its anode connected to node 422. Node 422 is also connected to both inputs of a logical NAND gate 440 whose output is connected as one input of a second logical NAND gate 441. The second input of NAND gate 441 is taken from the OUT output of a timer module 442 which may be, for example, a conventional 556 timer. The timer 442 has its DIS input connected to one terminal of a resistor 443 whose opposite terminal is connected to a +5 volt source of potential. The DIS input is also connected to one terminal of a trim resistor 444 whose opposite terminal is connected directly to the TL and TR inputs of the timer 442 and to the trim adjustment arm 445 associated with resistor 444. The opposite terminal of the trim resistor 444 is also connected to ground through a capacitor 446 and the VC terminal also connects to ground through a capacitor 447. The RE input is taken from input node 448 and node 448 is connected to the inverting output $\overline{Q}$ of the one shot multivibrator 449 which may be, for example, a conventional 74123 device. Simultaneously, the input node 448 is connected to the LOAD input of a ramp counter 450 which, in the preferred embodiment of the present invention, is a conventional 74193 device.

The one shot 449 has its CX terminal connected to the RX terminal through a capacitor 451 and the RX terminal is connected to a +5 volt source of potential through a resistor 452. The clear input CLR is connected through a capacitor 453 to a grounding node which grounds the A and the GND terminals of the one shot 449. The B input is connected directly to the collector of a transistor 454 and the collector is also connected to a +5 volt source of potential through a resistor 455. The emitter of transistor 454 is connected to ground and the base is also connected to ground through a diode 456 which is poled with its anode grounded and its cathode connected to the base. The base of transistor 454 is also connected through a resistor 457 to an input lead 458 as hereinafter described.

The ramp counter 450 has its CD input connected to the output of NAND gate 441 and its LOAD input connected to node 448. The outputs of the counter 452 are designated QA, QB, QC, and QD and are connected to an output node 460 through resistors 461, 462, 463 and 464 respectively. The output node 460 is connected to a +5 volt source of potential through resistor 465 and to the inverting input of an operational amplifier 466. The non-inverting input of amplifier 466 is connected though a resistor 467 to a pair of potentiometer arm members 468 and 469. Potentiometer arm 468 is associated with a potentiometer of trim resistor 470 which has one terminal conneced to a +5 volt source of potential to a resistor 471 and its opposite terminal connected to ground through a resistor 472. Similarly, the potentiometer arm 469 is associated with a potentiometer or trim resistor 473 which has one terminal connected to a +5 volt source of potential through a resistor 474 and its opposite terminal connected to ground through a resistor 475. The output of operational amplifier 466, which is configured as a conventional comparator, is supplied through a resistor 476 to the base electrode of an output transistor 477. The collector of transistor 477 is connected to a +5 volt source of potential through a resistor 478 while the emitter is connected to lead 479 for supplying the output signal to the pen heat triac gate of FIG. 28 as hereinafter described.

The HI RATE or HI HEAT signal which is used to command a normal or high heat to the pen is supplied via lead 158 from the PB3 output of PIA 132 of FIG. 7 as previously described. Lead 158 supplies the HI RATE signal to one terminal of a trim resistor 480 whose opposite terminal is connected back to provide the adjustable potentiometer-like arm or trip tap element 481 for selectively adjusting the resistance in the circuit and therefore serving as a high heat trim adjustment for selectively adjusting the value of the high heat signal. The second terminal of the high heat trim resistor 480 is connected to the first terminal of a potentiometer or variable resistor 482 whose opposite terminal is grounded. A wiper arm or potentiometer element 483 may be adjustably positioned along the resistor 482 as known in the art to control the value of the signal picked up by the element 483. The arm 483 is connected through a resistor 484 to an input node 485 which is concerned to the non-inverting input of amplifiers 431 and 434 and which, in fact, corresponds to the voltage divider input node 424 previously described.

The input from the microprocessor 30 which arrives on lead 352 as the signal CHART ON serves two functions. It not only serves to start the chart motor but also to enable the pen heat control circuitry. This input is used when a graph is being drawn to enable full heat control. The lead 148 which supplies the PAPER ADVANCE signal starts the chart motor as well. However, it reduces the heat level of the pen during a Paper Advance command. This is done to prevent burning of the paper upon a paper advance command while the chart length control is at minimum position and a higher heat setting on the heat control. Under this condition with no vertical movement of the pen there is less heat dissipation from the pen by the paper which results in an above normal pen temperature.

The CHART ON signal from lead 352 is supplied to the inverting input of comparator 431 through a blocking diode 418. This comparator input is normally pulled high by the +5 volt source of potential through resistor 417. The non-inverting input of comparator 431 is held at about 2.5 volts by the voltage divider formed across the +5 volt supply by resistors 425 and 426. Therefore, when the inverting input of comparator 431 is pulled lower than 2.5 volts, the output of the comparator will go high to provide gate drive to the chart motor triac through diode 432 and lead 433. This as well applies a high level to the input of NAND gate 441 due to the inversion of the low CHART ON signal at the input of the inverting buffer NAND gate 440 thereby enabling NAND gate 441 to supply the timing signals from the timer 442 to the CD input of the ramp counter 450 as hereinafter described.

The PAPER ADVANCE signal on lead 148 does the above through blocking diode 419. In addition, it pulls the non-inverting input of comparator 423 low since this input is otherwise pulled high by the +5 volt source of potential and the pull-up resistor 421 and the inverting input is at 2.5 volts via the voltage divider resistors 425,426. This brings the output of comparator 423 low which pulls the heat level reference at the non-inverting input of comparator 466 low through the resistor 427 and the blocking diode 428. With a low signal at the non-inverting input of the comparator 466, only a portion of the pen heat reference setting will be developed resulting in a significantly reduced pen heat during start up.

The basic pen heat control is provided by the comparator 466 which drives a triac through transistor 477 to apply AC voltage to the pen. The comparator has a DC reference applied to its non-inverting input and the ramp signal generated by the ramp counter 450 applied to its inverting input. The ramp counter 450 is a conventional counter which generates a ramp with a weighted resistor network on its outputs. The counter is driven by the timer 442 which, in the preferred embodiment of the present invention, is adjusted to run at about 960 HZ and is synchronized with the AC input power by a zero-crossing detector comprising transistor 454 and the one shot multivibrator 449.

As stated, the AC power synchronization is achieved by transistor 454 and the one shot 449. Transistor 454 has an AC input from the secondary of the power transformer, not shown, but conventionally known and the input current is limited by resistor 457 and bias protection for the base-emitter junction is provided by the diode 456. The resistor 455 acts as a pull-up resistor to pull the collector up to +5 volts in the cut-off region of operation since transistor 454 is operated as a saturated switch. The square wave output at the collector of transistor 454 is applied to the B input of the one shot 449 which gives an output pulse on the rising edge of the input. The pulse-width is determined by the RC network comprising resistor 452 and capacitor 451, as known in the art. The duration of the pulse is 26 microseconds long and is applied to the reset RE input of the timer 442 and to the LOAD input of the ramp counter 450.

Resetting the timer 442 insures equal width pulses being applied to the ramp counter 450 to give a steadier firing point with respect to the AC input. Presuming the chart or graph on the output of the timer is gated to the count down input through the NAND gate 441, the counter 442 will count down from an all output high condition which was attained when the load pulse from the one shot 449 went low since thelow signal at the LOAD input of the counter 450 initially clocks in the count at QA, QB, QC, and QD to high values. A step function which ramps down from +5 volts to a low value is generated by the resistive network as each cycle of sixteen steps is produced to effectively divide the AC power input up into sixteen possible firing points for the pen heat triac. This ramp is applied to the inverting input of the comparator 466 with pull-up resistor 465 insuring a VOH of +5 volts from the network.

The non-inverting input of the comparator 466 receives a DC level signal from the resistive voltage divider made up of resistors 471, 472, 474 and 475 together with potentiometers 470 and 473. As this level is raised using one of the control potentiometers 473 or 470, the time elapsed from reset to gate trigger will become less as the step function ramp goes below the DC reference level causing the comparator 466 to toggle driving its output high. With a high signal at the output of comparator 466, the base of transistor 477 will be driven through the current limiting resistor 476 and will be turned on to supply gate drive current to the pen heat triac via its emitter circuit lead 479. Resistor 478 limits the gate drive, as known in the art.

The DC reference level from the external controls represented by potentiometers 470 and 473 is shunted under a Paper Advance condition since the paper advance comparator 423 will supply a low signal through a resistor 427 blocking diode 428 to hold the non-inverting input of comparator 466 relatively low bringing about a reduction in pen heat. Under high heat conditions, the microprocessor 30 has seen a pen deflection requirement of the given magnitude in advance of its actual movement and when this occurs a HIGH HEAT signal is applied to lead 158. This signal is sensed by the high heat buffer 434 through the high rate trim resistor 480 and the isolation resistor 484. This high rate or high heat signal produces an increased voltage at the non-inverting input of buffer amplifier 434 and therefore a corresponding increase in the output of the voltage follower buffer 434 will be applid through resistor 436 to the DC reference node at the non-inverting input of the comparator 466. This action increases the trip point on the ramp from the counter 450 at which the comparator toggle occurs and therefore the triac will be triggered sooner in the cycle of the AC input power waveform to increase the power supplied to the pen and thus increase the pen heat. The operation of the triac and the concept of triggering it at the various points in the AC cycle for pen heat purposes is old in the art and will not be discussed in detail herein.

Before discussing the recorder printer of block 52, the display of block 40, and the keyboard of blocks 42 and 44 of FIG. 1, additional portions of the PIA circuitry of block 34 will be described.

Figure 21:
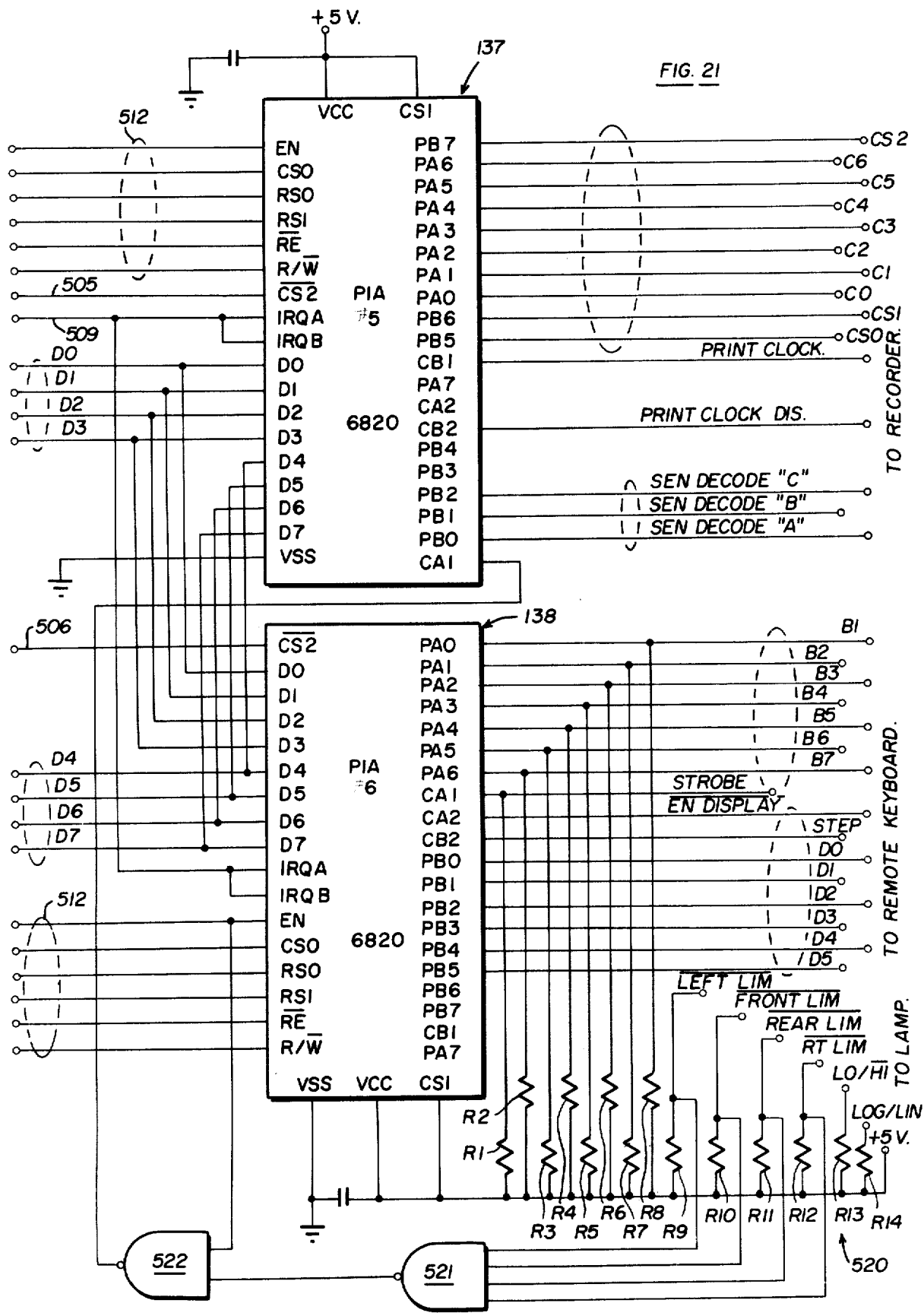
FIG. 21 is a detailed block diagram of yet another portion of the PIA circuitry of block 34.

FIGS. 20 and 21 describe the Peripheral Interface Adapters 135, 136, 137 and 138 of PIA block 34 of FIG. 1.

In addition to the Peripheral Interface Adapters 131 and 132 of FIG. 7, four more peripheral interface adapters 135, 136, 137 and 138 will now be described with reference to FIGS. 20 and 21. In the preferred embodiment of the present invention, the PIAs are conventional MC6820 devices used to interface the microprocessor system with the external peripherals. The data bus 36 to and from the PIAs 135, 136, 137 and 138 are buffered by conventional data bus buffers 501 and 502 which are, in the preferred embodiment of the present invention, conventional 8T28 devices such as previously described with respect to FIG. 4. Address decoding is performed by the address decoder 503 which is similar to the decoder 96 of FIG. 6 previously described and is, in the preferred embodiment, a conventional 74S138 device. The PIAs 135, 136, 137, and 138 are capable of generating interrupts by pulling the $\overline{IRQ}$ line low through a current sink transistor 504. The processor 30, when writing to or reading from the PIAs 135-138 goes through the same basic sequence. The primary difference is in the direction control of the data bus buffers 501 and 502. Therefore, a discussion will be given of a read sequence with the differences for the write sequence being pointed out. But first, the apparatus of FIGS. 20 and 21 will be further described.

In FIG. 20, the PIA outputs are all labeled with their associated function and the outputs of PIA 135 are labeled as going to the main keyboard whereas the outputs of PIA 136 are labeled as going to the carriage control circuitry, to the lamp, to the main keyboard, and to the recorder. Likewise, the outputs of PIA 137 are indicated as going to the recorder while the outputs of PIA 138 go to the lamp and to the remote keyboard as hereinafter described. The data bus outputs D0 through D7 of each of the PIAs 135-138 are supplied to the data bus 36 via data bus buffers 501 and 502 as previously described.

The address decoder 503 is shown as including four inputs Y4, Y5, Y6 and Y7. These outputs are used to provide the PIA chip select with the Y7 output being connected to the $\overline{CS2}$ chip select input of PIA 135; the Y4 output is connected to the $\overline{CS2}$ chip select input of PIA 136; the Y6 output being connected directly to the $\overline{CS2}$ chip select output of PIA 137 via lead 505; and the Y5 output being connected to the $\overline{CS2}$ chip select input of PIA 138 via lead 506. Simultaneously, all four of the decoder outputs Y4, Y5, Y6, and Y7 are connected to the four inputs of a NAND gate 507 whose output is connected as one input of a two input NAND gate 508.

Figure 4:
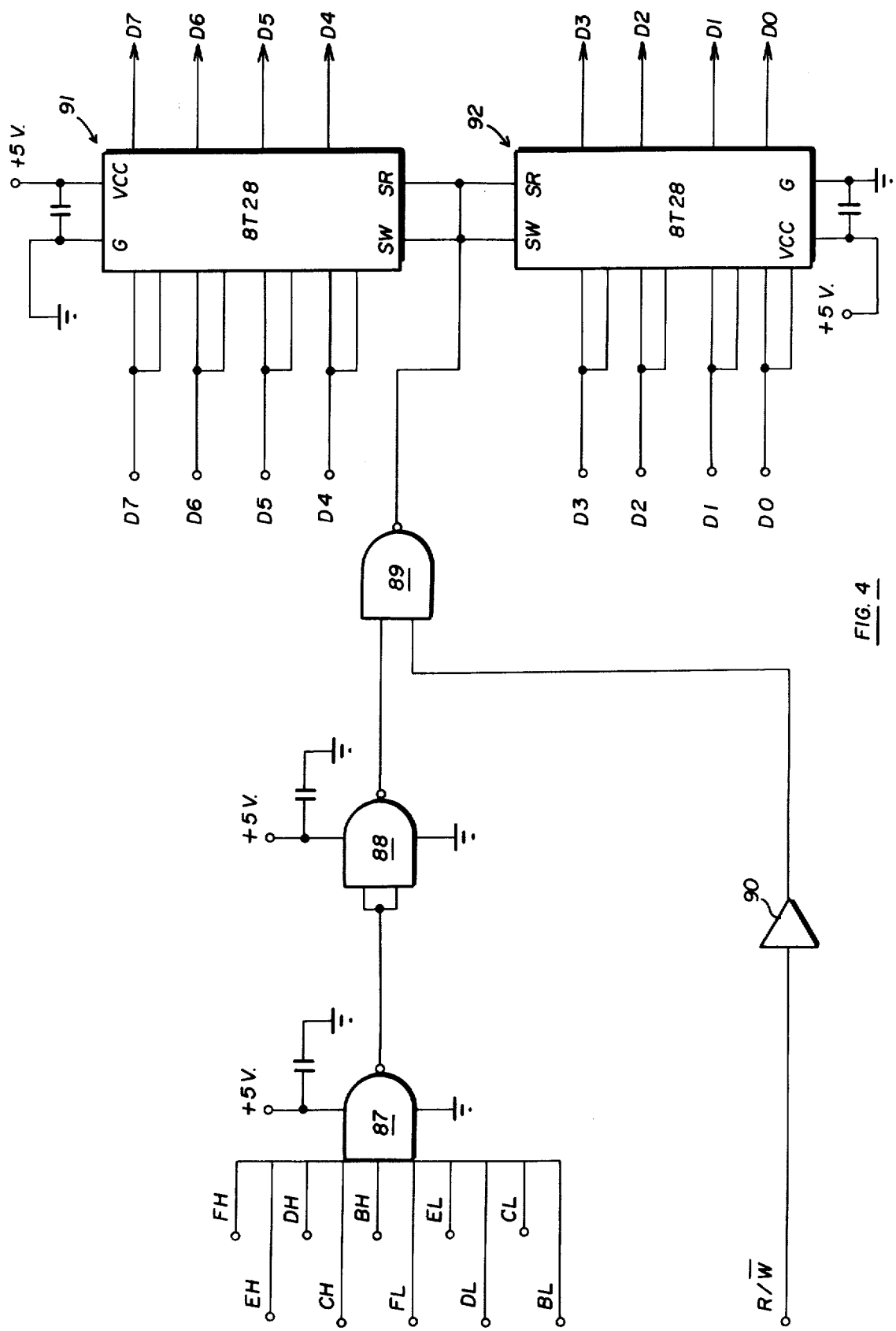
FIG. 4 is an electrical schematic diagram of the bi-directional data bus drivers associated with the Read Only Memories of block 32 and the Random Access Memories of block 33 of FIG. 1.

The other input of NAND gate 508 receives the read/write signal R/$\overline{W}$ and, as previously described with respect to FIG. 4, the output of NAND gate 508 will go high or low depending upon its inputs in order to control the direction at which the data lines D0 through D7 of the data bus 36 are driven as previously described. The IRQA and IRQB outputs of each of the PIAs 135, 136, 137 and 138 are commonly connected together via lead 509 and supplied to both inputs of a buffer NAND gate 510 which inverts the input signal and supplies the output to the base of a transistor 504 through resistor 511. The emitter electrode of transistor 504 is grounded while the collector supplies the interrupt request signal $\overline{IRQ}$ to the microprocessor 30 via lead 512 and the control bus 37. The control inputs to each of the PIAs 135, 136, 137, and 138 are represented by the group of control lines circled by the dotted line labeled 512 which includes the input lines bearing the signals 02, VMA, A0, A1, $\overline{RE}$, and R/$\overline{W}$ which control the operation of the PIAs as previously described.

A timer 513 is associated with PIA 136 to determine the time the scanned pattern is displayed in the auto step mode of operation, and control over the timer 513 is provided by the PIA 136. The timer 513 is, in the preferred embodiment of the present invention, a conventional 1455 timer with its reset input RE connected directly to the CB2 output of PIA 136 and the timer output OUT connected to the CB1 input of PIA 136. Pin number 1 of the timer 513 is connected directly to ground; pin 5 is connected to ground through a timing capacitor 514; pins 2 and 6 are connected to ground through a capacitor 515 and to the pin 7 terminal through a trim resistor 516. Pin 7 is also connected to a +5 volt source of potential through a resistor 517. The +5 volt source of potential as supplied directly to pin 8 and to the CS1 and VCC inputs of the PIA 136. The pin 8 input is also connected to ground through a capacitor 518 and its function will be briefly described hereinafter.

The carriage outputs of the PIA 136, i.e., the signals (1) $\overline{LEFT}$ LIM from output PA4; (2) $\overline{FRONT}$ LIM from output PA7; (3) $\overline{REAR}$ LIM from the PA6 output; and (4) $\overline{RT}$ LIM from the PA5 output of PIA 136 are supplied to the carriage circuit limit switches as indicated in FIG. 20 and are also supplied to the circuit of FIG. 21 where they are pulled up by a multiple resistor package designated generally by the reference numeral 520 which includes resistors R1 through R14. More specifically, the signals from the outputs PA4, PA7, PA6 and PA5 are supplied to one terminal of resistors R9, R10, R11 and R12 respectively while the opposite terminal of the resistors is connected to the +5 volt source of potential. These four signals are also supplied as the four inputs of a four input NAND gate 521 whose output is connected as one input of a two input NAND gate 522. The opposite input of NAND gate 522 receives the second clock phase signal $\phi2$ and the output is connected directly to the CA1 input of PIA 137. Additional information on the PIAs 135, 136, 137 and 138 and related circuitry of FIGS. 20 and 21 may be had from the following brief general description.

As stated previously, each PIA will respond to four addresses. The lowest address is normally how the PIA is referenced and in reading from a PIA, the processor 30 goes through a normal read cycle. That is, it places the read/write R/W in a high state, brings the signal VMA high and places the appropriate address on the address bus 35. Th address decoder 503 is a conventional one-of-eight decoder and its inputs are the address lines A10 through A15. Addresses A10, A11, and A12 determine which output of the decoder will be pulled low while addresses A13, A14 and A15 perform an enable function on the decoder. The A15 address which is supplied to the G1 input must be high and the A13 signal to the G2A input and A14 signal to the G2B input must be low prior to any output being selected. Thus, the three most significant bits of the address must be 100. The outputs used are Y4, Y5, Y6 and Y7 demanding an input count on C, B and A of four through seven or binary 100 through binary 111. Putting this information together shows that the decoder responds to signals between 100100 through 100111. The foremost significant bits determine the hex digit of the address of "nine". The next digit, defined by the next four bits and so on. Since there are no other devices responding to an address within the 9,000 block of addresses further decoding is not required.

Each output of the decoder 503 has been tied to a chip select input CS2 of a unique one of the PIAs 135, 136, 137, and 138 to provide a chip select function. Each of these outputs are also tied to a four input NAND gate 507 which serves as a part of the data bus driver direction control scheme which includes data bus drivers 501 and 502. When a chip select occurs, an input to NAND gate 507 goes low driving its output high and since this output is NAND'ed with the R/W line, this output is used to control the direction of drive of the data bus drivers 501 and 502 as previously described in FIG. 4.

All of the PIA data outputs D0 through D7 are bussed and the devices are designed for a bussed system and will only try to drive the line when proper chip select read conditions exist. By each device having a specific address, no multiple drive or bus contention condition will be encountered. As stated previously, the address decoder 503 selects one of the four possible PIAs by activating their chip select CS2 inputs. Also, each PIA responds to four addresses determined by the A0, A1 lines being applied to the RS0 and RS1 inputs respectively. The R/W input of each PIA is tied to the R/W buffered signal from the control bus, not shown, but which may be a conventional 8T97 device. The signal present at the enable input EN with the PIAs provide all of the internal timing and is therefore the second clock phase signal $\phi 2$ or some derivative thereof.

To summarize, the read/write cycle, at some time during the phase 1 clock signal, the processor places the address on the address line, brings the signal VMA high, and the R/W line to its proper level. This address is decoded by the address decoding circuit 503 bringing the proper output low to select the desired PIA. The VMA and R/W lines condition the PIA by providing another chip select and by providing the proper read/write mode. The data bus direction control via NAND gates 507 and 508 switches to its proper level in bus drives 501 and 502 to enable the transfer of data from the processor to the PIA for a write or from the PIA to the processor for a read operation. The address signals A0 and A1 select the proper internal register within the PIA as previously described. If it is a read cycle, then the second clock phase signal 02 on the enable input EN goes high to cause the internal transfer of data from the output ports to the data bus and this transfer will end when the second clock phase signal 02 falls by the processor accepting the data. If it is a write cycle, the data will be coming from the processor through the data bus drivers 501 and 502 during the second clock phase 02. As the enable signal falls at the PIA, the device will accept the data and transfer it into the proper internal registers to complete the cycle.

One of the remaining processor interface lines involved in the IRQ interrupt request line. Due to the programming involved, each PIA is capable of recognizing a falling or rising edge on a signal coming to the inputs CA1, CA2, CB1, and CB2. If programmed to do so, the PIA as a result of the edge detection will pull the wired IRQA and IRQB line low. This action will interrupt the processor by generating the interrupt request signal IRQ via NAND gate 510 and transistor 504 and the signal IRQ will interrupt the processor so that it can perform some desired function. When the PIA pulls the IRQ output pin low, it is seen by the inverting buffer 510 and the output of the buffer 510 drives the transistor 504 base high through the limiting resistor 511. The transistor will then conduct to pull the IRQ line low to signal the processor 30 of the interrupt request.

The discussion of the external input/output lines of each of the PIA devices will be briefly summarized below by the PIA reference numeral. Each line refers to the appropriately designated PIA input or output and any name or nemonic given thereto is followed by a brief description of its function and like functions will be grouped together to avoid redundancy.

The third PIA 135 or processor address 9C00 has its I/O lines delivered to the main chassis keyboard as indicated below:

PAO-PA4 Keyboard Data. These pins are input pins for the main chassis keyboard. PAO is the LSB.

PA5 Keyboard Valid. This line is high when the main chassis keyboard data (PA0-PA4) is valid.

PA7 DUMP This is an active low data dump inhibit switch input. The locking alternate action switch and LED indicator are located on the main chassis keyboard.

PA¢, PRO-PB7, QNCH, INS1, INS2, EXS, OD SRD, PKPK, FSA, EEL and ACF.

These are all outputs dedicated to drive the main chasis or front panel indicator lights of the same name via transistor switches.

CA1, CB1, X chop, Y chop. These inputs provide the processor with a count pulse from the X and Y carriage encoder circuitry on the main chassis keyboard. This enables the unit to maintain an internal position count of the carriage. The up/down directional information of the count is provided by X and Y direction (CA2 and CB2).

CA2, CB2 X DIRECTION Y Direction. These inputs provide directional information for the internal counter within the processor system which is associated with the carriage location. It is not a level sensitive input but a transition vs no transition type of operation.

The fourth PIA 136 is at processor memory address 9000. PIA 136 accepts inputs from the carriage control limit switches, the optics, and the main chassis keyboard with outputs to the motor control boards of the recorder. Control over the timer 513 is also performed by PIA 136 and this timer determines the time the scan pattern is displayed when operating in the auto step mode of operation. The inputs and outputs are as follows:

PA0 $\overline{\text{X MOTOR}}$. This output is a low enable for the carriage X axis (scan direction) motor control board (30-10). The direction of the motor drive will be determined by PA1 LEFT/$\overline{\text{RIGHT}}$ control, delivered to motor control board via main chassis keyboard as are the following PA1-PA7.

PA1 LEFT/$\overline{\text{RIGHT}}$. This output determines the direction of X axis drive high = LEFT, low = RIGHT.

PA7 FRONT/$\overline{\text{REAR}}$. This output determines the direction of Y axis drive high = FRONT, low = - RIGHT.

PA3 $\overline{\text{Y/MOTOR}}$. This low enable output turns on the Y axis (step direction) motor control board. It is associated with PA2 above for direction control.

PA4, 5, 6, 7 $\overline{\text{LEFT}}$, $\overline{\text{RIGHT}}$, $\overline{\text{REAR}}$, $\overline{\text{FRONT}}$ LIMIT. These input go to the carriage limit switches. They are pulled up by a multiple resistor package 520. As stated above these inputs are associated with an $\overline{\text{IRQ}}$ generating input at CA1 of PIA 137 via NAND gates 521, 522.

CA1 $\overline{\text{KBD SERVICE REQUEST}}$. This edge activated input requests the processor to read the main chassis keyboard.

CA2 $\overline{\text{CHART ON}}$. This output turns the chart recorder on when it goes low. This is the normal, full pen heat as required, chart on signal used during graph reproduction.

PB0 LOG/$\overline{\text{LIN}}$ MODE. This input provide information to the processor as to which operating mode the input amplifier 171 of FIG. 8 should be in. If the output is low it will switch to the linear mode of operation, high for log.

PB1 $\overline{\text{SAMPLE}}$. This output controls the sample and hold amplifier within the recorder module on the pen driver board (30-18).

PB2-PB5 Not Used.

PB6 LO/$\overline{\text{HI}}$ LAMP MODE. This input provides information as to the operating point for the visible lamp and the PM tube high voltage. If this input is high the processor will signal the power supply to be in the low mode for the visible lamp and PM tube high voltage. A low level on this input dictates the high lamp mode. These are the normal levels and are changed for the "LAMP" invert mode.

PB7 LO/$\overline{\text{HI}}$ LAMP CONTROL. This output drives the power supply switching for low and high lamp and PM tube high voltage.

CB1, CB2 This input and output, respectively, are associated with timer 513. It is used to set the display time for the scan on the oscilloscope during one of the auto step modes of operation. The output of CB2 disables the timer 513 by holding it in a reset condition. In the auto step mode of operation, if desired, the output of CB2 will be brought high after a scan has been made. This enables the timer 513 to start the timing period. As the time out transition is seen at CB1 from the output of the timer 513, the PIA 136 will commence to draw a graph of the scan.

The fifth PIA 137 of FIG. 21 is at system memory address 9400. All but one of its I/O ports are routed to the recorder printer along with two outputs from PIA 136. The inputs and outputs are as follows:

PA0-PA6, PA5-7 A0 through A9. These outputs drive the character generator for the printer within the recorder module. $A_0$ through $A_6$ are the ASCII character to be printed and $A_7$ through $A_9$ pertain to what column of the 7×9 dot matrix character is to be printed.

PA7, PB3, 4 CA2. Not Used.

PB0-PB2. SENTENCE DECODE A, B, C. These three outputs drive the decoding circuitry in the recorder that selects which sentence is being printed.

CA1 Input CA1 acts as an interrupt input for the carriage limit switches. If the carriage overruns a position and drives to an extreme it will depress a conventional limit switch. If any of the lines go low (depressed switch) the output NAND gate 521 goes high and if any of the lines go enabling NAND gate 522 to pass 02 a transition is seen at CA1 input. This transition will set a register within the PIA which, if programmed, will generate an $\overline{\text{IRQ}}$. The processor will turn off motor drive and display the prompt "LOCATION ERROR".

CB1 PRINT CLOCK. This is the input for the printer, clock which is located in the recorder module. The print routine in the processor is interrupt driven via $\overline{\text{IRQ}}$ from this edge triggered input.

CB2 $\overline{\text{PRINT CLOCK DIS}}$. This output, when low, enables the printer, clock, protective circuit, etc., in the recorder module.

The sixth and last peripheral interface adapter, PIA 138 of FIG. 21 is at memory address 9800 and this PIA is devoted to the remote keyboard and its associated display. The inputs and outputs are as follows:

PA0-PA6 B1 thru B7. These pins are inputs to the system for the keyboard portion of the remote keyboard assembly. B1 is the least significance bit, etc. A multiple resistor package 520 pulls these lines high.

PA7 Not used.

CA1 $\overline{\text{STROBE}}$. This is a service request input to the processor from the remote keyboard. A transition on this line sets an internal flag to tell the processor a key has been depressed.

CA2 $\overline{\text{EN DISPLAY}}$. This output is normally low to enable the circulating memory for the display portion of the remote keyboard assembly. This line will go high when the processor loads the referenced circulating memory.

CB2 $\overline{\text{STEP}}$. This output is utilized in incrementing the circulating memory during a loading of that memory. The increment of the memory counter will take place on the rising edge of this negative going pulse.

PB0-PB5 D0 through D5. These outputs supply the circulating memory for the display with data to be displayed. This takes place only during the load cycle of the memory.

PB6-7 CB1 Not used.

With the explanation given above, the discussion of the peripheral interface adapters and their associated circuitry is concluded and if a more detailed description is required, reference is again made to the Motorola Publication previously incorporated by reference herein. It is believed that the description given together with the listing and brief description of the signals on the non-processor side of the I/O ports is adequate for a thorough understanding of the present invention.

The recorder circuitry of block 50 of FIG. 1 has already been described and since the printer of block 52 of FIG. 1 is actually part of the recorder assembly, it will now be described. The recorder module enables the user of the Densitometer of the present invention to produce a permanent record of a scanned pattern. The reproduction of the pattern, as stated before, is made up of two sections. The analog trace of the waveform pattern is drawn on the grid pattern of the chart paper and the second section includes the printed information along the clear track along the bottom of the paper as previously described.

The printer circuitry of block 52 of FIG. 1 includes a voltage regulator cut-out circuit for maintaining optimum print quality and to protect the thermal print head from damage due to overvoltage conditions. The voltage regulator and cut-out circuitry will be described with reference to FIG. 22.

A resistor 530 has one terminal connected to a +28 volt source of potential and its opposite terminal connected to the cathode of a zener diode 531 whose anode is connected directly to ground. The junction of the zener diode 531 and resistor 530 is connected to ground through a capacitor 532 and is also connected to one terminal of a print heat adjust trim resistor 533 and the other terminal of trim resistor 533 is connected to ground through a resistor 534. The adjustable wiper element or tap 535 supplies the print heat adjust signal to the non-inverting input of an operational amplifier 536 configured as a conventional difference amplifier. The junction of the zener diode 531 and resistor 530 is also connected to one terminal of the second print cut-out adjustment trim resistor 537 and its opposite terminal is connected directly to ground. The wiper arm or voltage tap element 538 supplies the print cut out adjustment signal to the inverting input of operational amplifier 539 which is configured as a conventional comparator.

A +22 volt source of potential is connected to one terminal of a resistor 540 whose opposite terminal is connected to a first terminal of a second resistor 541 whose opposite terminal is connected to ground. The voltage divider node at the junction of resistors 540 and 541 is connected directly to the inverting input of the difference amplifier 536 and to the non-inverting input of the comparator 539. The output of comparator 539 is connected to one terminal of a first voltage divider resistor 542 whose opposite terminal is connected to a voltage divider node 543. Voltage divider node 543 is connected through a resistor 544 to ground. The voltage divider node 543 is connected through a resistor 545 to the non-inverting input of an operational amplifier 546 which is configured as a "one-shot" device. Voltage divider node 543 is also connected through a resistor 547 to the output of the one-shot 546. The inverting input of the one-shot 546 is connected to one terminal of a resistor 548 whose opposite terminal is connected through a diode 549 to the output of the one-shot 546 and simultaneously to a node 550. Node 550 is connected to ground through a capacitor 551 and is connected through a resistor 552 to the output of the one-shot 546.

The output of the one-shot 546 is also connected to the inverting input of an operational amplifier 553 whose non-inverting input is connected to a voltage divider including resistors 554 and 555. The resistor 554 has one terminal connected to a positive source of potential and its opposite terminal connected to the voltage divider output node which connects to the non-inverting input of amplifier 553 and the voltage divider node connects through a second resistor 555 directly to ground. The output of the amplifier 553 is connected directly to the base of a Darlington amplifier transistor 556 whose collector provides the printer cut out signal CUT OUT via lead 557. The emitter of transistors 556 is connected through a resistor 558 to ground, through a capacitor 559 to ground, and to the collector of a second Darlington transistor 560 whose emitter is connected directly to the +22 volt source of potential and whose base is connected directly to the output of the difference amplifier 536.

Figure 22:
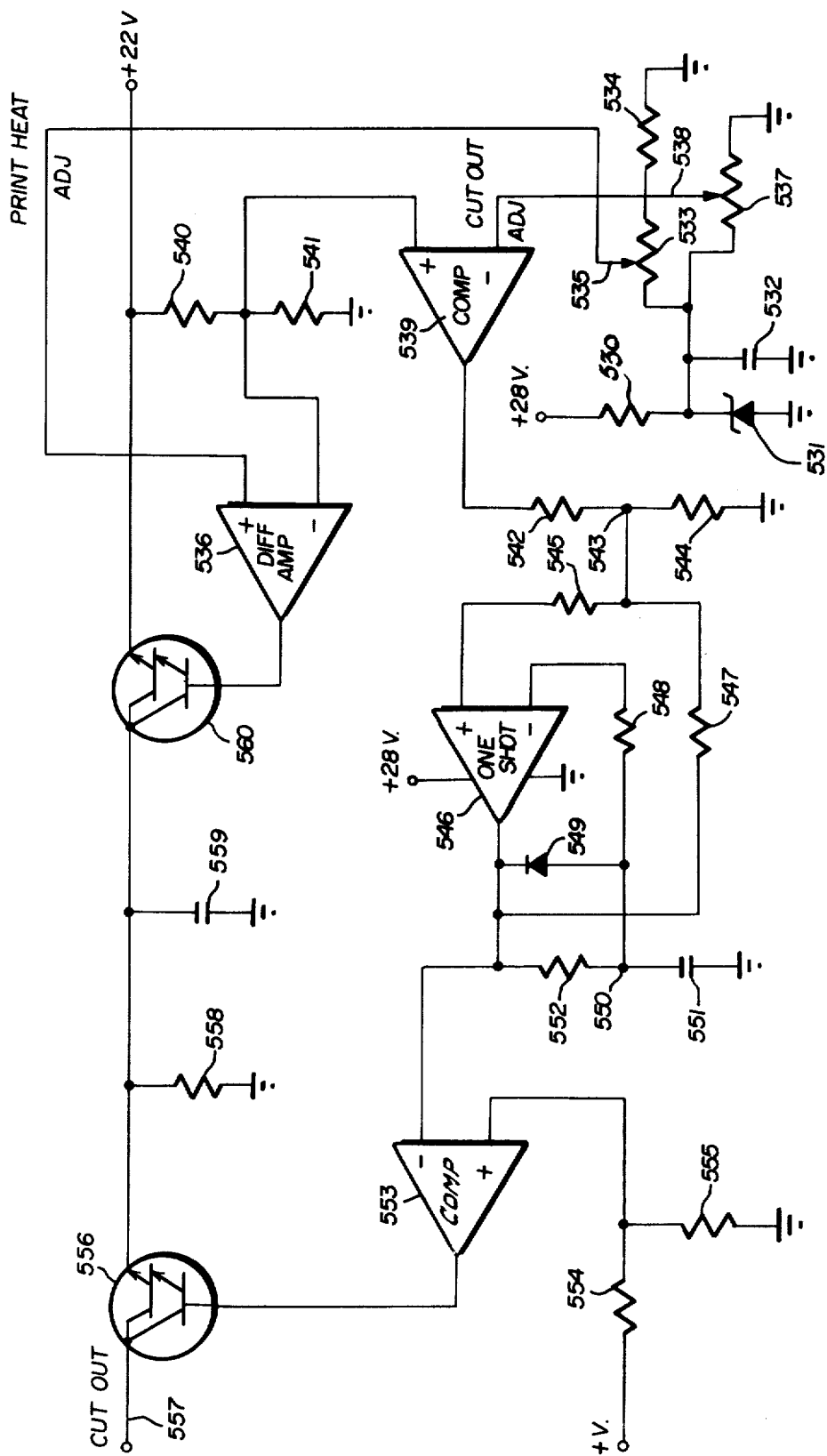
FIG. 22 is an electrical schematic diagram of a portion of the control circuitry associated with the printer of block 52 of FIG. 1.

The operation of the voltage regulation and cut-out circuitry of FIG. 22 will now be briefly described. The voltage regulator section includes operational amplifier 536 and a series pass element comprising transistor 560. The operational amplifier 536 is, in the preferred embodiment of the present invention, one-fourth of a quad op amp package such as a standard MC3403 IC while the Darlington transistors 556 and 560 may be conventional Tip 120 transistors. The difference amplifier 536 drives the series pass element 560 in a linear mode to control the voltage output. The output voltage is sensed on the inverting input of the op amp 536 by the voltage obtained from the resistive voltage divider comprising resistors 540 and 541. A print heat adjustment reference is applied to the non-inverting input of the amplifier 536 and is derived from a zener diode stabilized adjustable resistive voltage divider which includes resistor 530, zener diode 531, trim resistor 533 and resistor 534. Any difference between the reference voltage supplied to the non-inverting input and the output sense voltage is amplified and applied to the base of the series pass transistor 560 as a change in the base drive thereby bringing about a change in the output to return the voltage to the desired level.

The cut-out circuit controls the power applied to the voltage regulator circuit discussed above and utilizes operational amplifier 539 as a comparator by virtue of the open loop gain. The output voltage of the regulator is sensed at the resistive voltage divider made up of resistors 540 and 541 which is applied to the non-inverting input of comparator 539. The voltage applied to the trim resistor 537 and stabilized by the zener diode 531 is applied to the inverting input of comparator 539. If the printer voltage regulator output rises above the trip point set for the comparator 539, the comparator will toggle its output going high. This action will set the one-shot 546 causing a high signal to be applied to the inverting input of amplifier 553. Since amplifier 553 is also configured as a comparator with a reference voltage supplied to the non-inverting terminal via the voltage divider pair 554, 555, a high signal is supplied to the inverting input will bring the output of the comparator 553 to ground causing transistor 556 to go into cut-off thereby removing the applied voltage from the regulator circuit. The one-shot 546 will reset causing the printer voltage to be re-applied and this action will continue until the output voltage of the regulator is brought down to a level of less than the trip point. The one-shot 546 contains a positive feedback loop such that as a high input signal is applied by way of resistor 545, the output starts going high which reinforces the applied signal via resistor 547. Capacitor 551 starts charging toward the output voltage through resistor 552 and after a certain time has elapsed the voltage on the capacitor 551 and thus the inverting input of the comparator 553 will become higher than the input level applied to the non-inverting reference input. When this occurs, the output of the one-shot 546 will go low to discharge the timing capacitor 551 through the diode 549 and if the positive input level has been removed from the one-shot 546, it will stay reset to enable the printer applied voltage. Therefore, the regulator and cut-out circuitry of FIG. 22 constantly monitor the voltage supplied to the printer and regulate it within predetermined limits and if the trip limit is exceeded, the voltage output is cut off for a predetermined period of time before it is re-applied and checked again. This goes on until the proper voltage levels are achieved and maintained, as known in the art.

Figure 23:
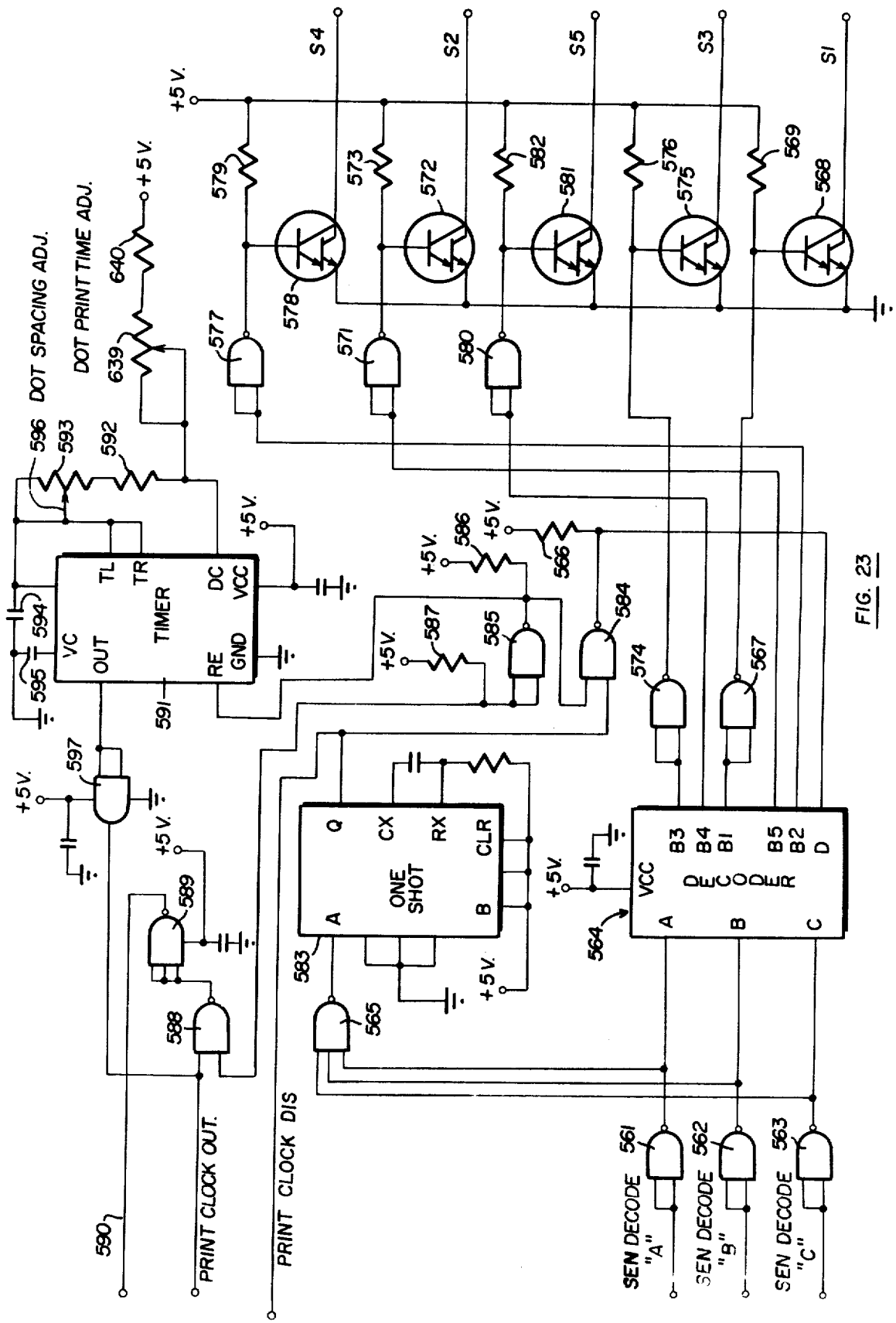
FIG. 23 is an electrical schematic diagram of additional print control circuitry associated with block 52.

The printer circuitry including the circuits for the dot drive the printer clock, the sentence select circuitry and the protective circuit will now be described with reference to FIGS. 23 and 24. In FIG. 23, the sentence decode "A" from the PB0 output of PIA 137 of FIG. 21 is supplied directly to both inputs of the logical AND gate 561 which serves as a buffer. The sentence decode "B" signal from the PB1 output of PIA 137 is also connected to both inputs of a two input logical AND gate 562 which serves as a buffer and similarly, the sentence decode "C" signal from output PB2 of PIA 137 is connected to both inputs of a buffering AND gate 563. The output of the AND gate buffer 561 is connected directly to the "A" input of a one-of-ten decoder 564 such as a conventional 7442 device and simultaneously is supplied to one input of a three input NAND gate 565. The output of the buffering AND gate 562 is connected directly to the "B" input of buffer 564 and to the second input of NAND gate 565. Lastly, the output of buffered AND gate 563 is supplied to the "C" input of the decoder 564 and to the third and last input of NAND gate 565.

The "D" input of the one-of-ten decoder 564 is connected to a +5 volt source of potential through a resistor 566 while the "B1" output is connected to both inputs of a logical NAND gate 567 used as an inverting buffer drive and the output of NAND gate 567 is connected directly to the base of a Darlington configured transistor 568. The base of transistor 568 is also connected through a resistor 569 to a +5 volt source of potential while the emitter electrode is connected directly to ground and the collector supplies the Select Sentence number one command "S1" to the actual printer, not shown, but known in the art for selecting which sentence is to be printed at a given time.

The "B2" output of the decoder 564 is connected directly to both inputs of a logical NAND gate 571 which serves as an inverting buffer driver and the output of gate 571 is connected to the base of a transistor 572 and through a resistor 573 is connected to a +5 volt source of potential. The emitter of transistor 572 is connected directly to ground and the collector supplies the Select Sentence number two command "S2" to the printer.

The "B3" output of the one-of-ten decoder 564 is connected to both inputs of a logical NAND gate 574 which serves as an inverting buffer driver and its output is connected to the base of a transistor 575 and through a resistor 576 to a +5 volt source of potential. The emitter electrode of transistor 575 is connected directly to ground while the collector supplies the Select Sentence number 3 command "S3" to the printer. The "B4" output of the decoder 564 is connected to both inputs number 3 command "S3" to the printer. The "B4" output of the decoder 564 is connected to both inputs of a NAND gate 577 which serves as an inverting buffer and the output of NAND gate 577 is connected to the base of a transistor 578 and is also connected through a resistor 579 to the +5 volt source of potential.

Lastly, the "B5" output of decoder 564 is connected to both inputs of a logical NAND gate 580 which serves as an inverting buffer driver and the output of NAND gate 580 is connected to the base of a transistor 581 and is further connected through a resistor 582 to a +5 volt source of potential. The emitter electrodes of transistors 578 and 581 are connected directly to ground while the collector of transistor 578 supplies the Select Sentence number four command "S4" to the printer and the collector of transistor 581 supplies the Select Sentence number five command "S5" to the printer for sentence selection purposes. The output of the sentence select NAND gate 565 is connected directly to the "A" input of a one-shot multivibrator 583 such as a conventional 74123 device which is used in the re-triggerable mode. The non-inverting output Q is used to supply the Print Clock Disable signal to the CB2 input of the PIA 137 of FIG. 21 and also supplies this signal to a first input of NAND gate 584. The output of NAND gate 584 is connected to a +5 volt source of potential through the resistor 566 and then to the "D" input of the one-of-ten decoder 564 previously described. The second input of NAND gate 584 is taken from the output of NAND gate 585 and the output of NAND gate 585 is also connected to a +5 volt source of potential through a pull-up resistor 586. Both inputs of NAND gate 585 are connected together so that the NAND Gate 585 serves as an inverting buffer. The inputs of NAND gate 585 are also connected to a +5 volt source of potential to a pull-up resistor 587 and are also connected to one input of a NAND gate 588. The other input of NAND gate 588 is the print clock out signal generated by the circuitry of FIG. 23 as hereinafter described and which is also supplied back to the CB1 input of PIA 137 of FIG. 21.

The output of NAND gate 588 is also connected to all inputs of the three input NAND gate 589 which serves as an inverting buffer and its output is connected via lead 590 to the circuit of FIG. 24 as hereinafter described. The output of NAND gate 585 is also connected to the reset input "RE" of the timer 591 which, in the preferred embodiment of the present invention, is a conventional 555 timer. The timer 591 has its "DC" input connected via resistor 592 to a trim resistor 593 which is connected through a capacitor 594 to ground and the "VC" output is also connected to ground through a capacitor 595. The "TL" and "TR" outputs of the timer 591 are connected to the potentiometer wiper arm 596 and then through capacitor 594 to ground. This is a conventional configuration for a 555 timer with the external capacitors and resistors establishing the RC time constant and therefore the rate and period of the timer or clock 591. The output OUT of the timer 591 is connected to both inputs of a logical AND gate 597 which serves as a buffer driver to supply the print clock out signal to the input of NAND gate 588 and to the CB1 input of PIA 137 as previously described.

Figure 24:
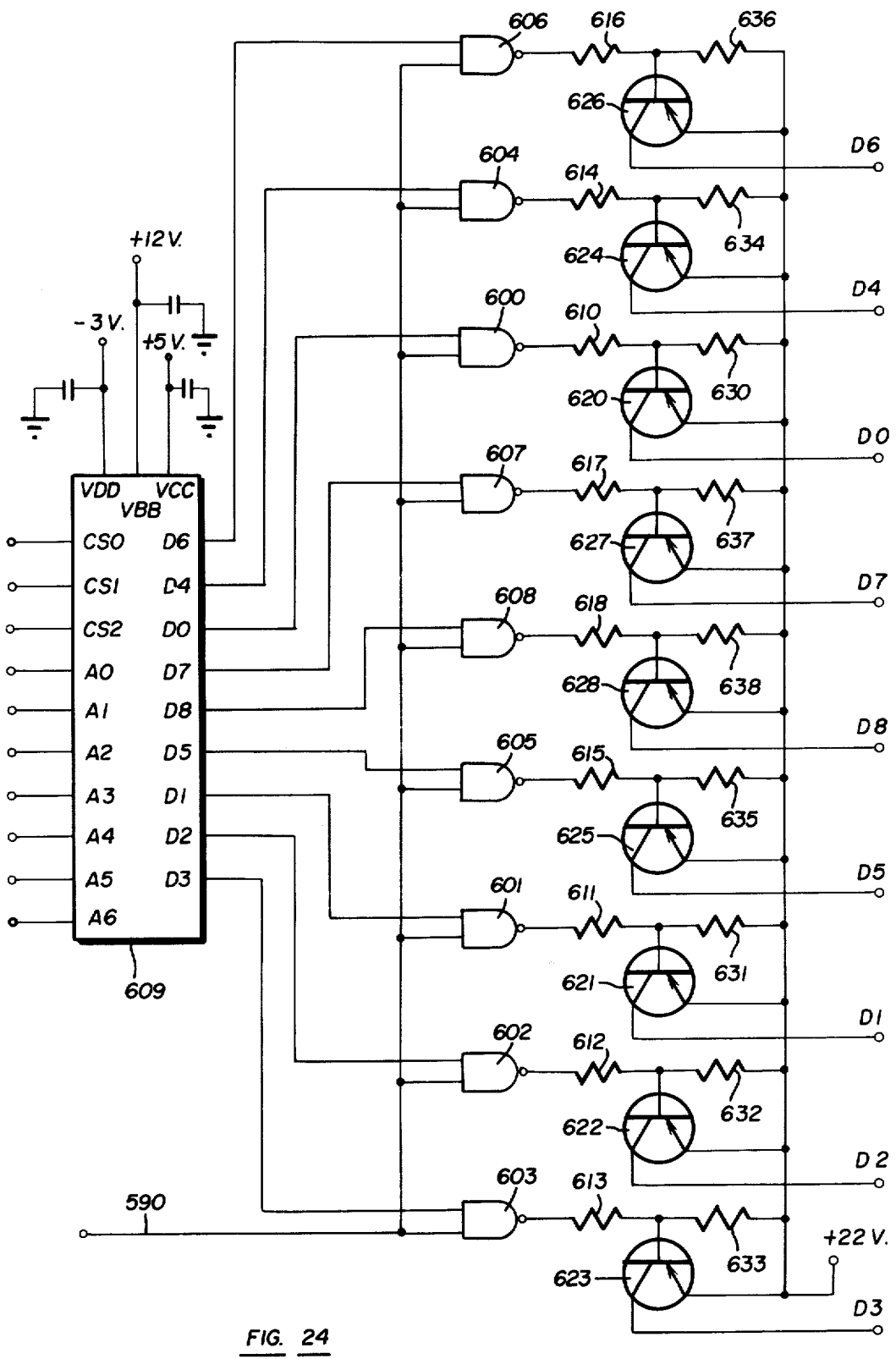
FIG. 24 is a schematic diagram of the print head driver circuit associated with the printer of block 52.

Lead 590 from the output of the NAND gate buffer 589 of FIG. 23 is connected to one input of each of nine separate NAND gates 600 through 608 of FIG. 24. The other input to each of the NAND gates 600 through 608 are taken from the corresponding output D0 through D8 of a decoder 609. In the preferred embodiment of the present invention, the decoder 609 is a conventional MOS memory chip such as a MC6581 which performs the necessary decoding function. The CS0, CS1 and CS2 inputs receive the CS0, CS1 and CS2 signals from the PB5, PB6 and PB7 outputs of the PIA 137 of FIG. 21. Similarly, the inputs A0 through A6 of the decoder 605 are coupled via leads C0 through C6 to the ouputs PA0 through PA6 of the PIA 137 of FIG. 21 to provide the proper ASCII coded characters to the recorder printer.

The outputs of the NAND gates 600 through 608 are each connected through a corresponding resistor 610 through 618 respectively to the base of an output transistor 620 through 628, respectively. The base of each of the transistors 620 through 628 is also connected through a resistor 630 through 638, respectively, to a +22 volt source of potential. The emitter pf each transistor is also connected directly to the +22 volt source of potential while the collector of each of the transistors 620 through 628 is used to output the character information signals D0 through D8, respectively, to the conventional dot matrix printer of the present invention, not shown, but known in the art.

A brief summary of the operation of the circuitry of FIG. 23 and 24 will now be given with the dot drive circuitry discussed first. As the chart papers advances and printed information is to be produced, the microprocessor 30 will present ASCII coded to the recorder printer. Each character is made up of select dots from a seven wide by nine high dot matrix on the printed paper. Therefore, a code transformation is required from ASCII to a seven X9 dot matrix. This decoding is performed by the memory decoder 609. The decoder has three column select inputs CS0, CS1 and CS2 and six character inputs, A0 through A6. The thermal printing elements on the print head are arranged as a single line of 50 dots multiplexed into ten groups of five dots each. By virtue of the fact that the 7×9 dot matrix characters are to be produced from a single column of dots, a column select decode is required producing a horizontal type scan of the character. The actual dot burns progress from column one to sentence 1, sentence 2, sentence 3, sentence 4, and sentence 5. Then from column 2 to sentence 1, sentence 2, etc., and then through each of the five sentences of column three, etc., through column 7 in a like manner.

The output of the decoder 609 includes nine dot information lines D0 through D8 and these reply to open collector NAND gates 600 through 608 while the other input of each of the NAND gate 600 through 608 is supplied by a buffered clock signal derived from the timer 591 of FIG. 23. Therefore, for a dot to be enabled, the decoder must produce a high dot output and the printer clocked drive signal must be high. A precaution taken to prevent the destructive effects of continuously applied burn voltage on the print head elements. Upon the NAND gates receipt of two high level inputs, its output will go low sinking current through the two resistors associated with its output. This brings the base of the associated output transistors 620 through 628 to a potential sufficiently below its respective emitter allowing the transistor to go into saturation. This current is then applied to the respect dot on all sentences and depending upon which sentence is now enabled, one of the dots will heat up producing a burn or colored marking on the thermally sensitive chart paper as known in the art.

The clock associated with the printer of the present invention comprises the timer 591 of FIG. 23. This timer is enabled by a low enable signal input from the PIA 137 of FIG. 21. Associated with the timer 951 are a trim pot or a trim resistor 593 which controls the time the clock is low and is referred to the dot spacing adjustment and a second trim pot or trimming resistor 639 which adjusts the time the clock is high and therefore the dot burn time. This is referred to as the dot print time adjustment. For a nominal printing voltage of 20 volts, the time low should be about 0.4 milliseconds and the time high should be approximately 2.0 milliseconds. This will produce a well-formed character of reasonable intensity. The clock output is buffered by AND gate 597 and the clock signal is returned back to the microprocessor 30 to request a character up-dating and applied to an input of NAND GATE 488 for inclusion into the protective circuitry supplied to the dot driver NAND gates as hereinafter described.

The sentence selection circuitry accepts an input signal from the microprocessor 30 representative of the sentence to be enabled for the dot information that is present in the decoder 609 of FIG. 24. These signals are buffered by AND gates 561, 562 and 563 and are then applied to the inputs of a one-of-ten decoder 564. The decoder 564 its output (an active low) according to the binary input value present at the inputs A, B, C, and D. Input D is a protective signal and will be discussed briefly below. The low enable outputs from the decoder 564 are buffered by open collector NAND gates and a NAND gate high output is applied to the base of output transistors 568, 572, 575, 578, and 581 which are utilized as the enable current sinks for the five sentence selection signals previously described.

At the end of each sentence enable period, the sentence selection circuitry inputs go to binary 111 attempting to select sentence 7. This is an unused output of the decoder 764 and so no sentence is enabled, but this condition is detected by the three input NAND gate 565 which goes low setting a one shot multivibrator 583. The one shot is used in a re-triggerable mode and the output goes high causing the output of NAND gate 388 to go low and the output of NAND gate 389 to go high thereby enabling each of the dot driver NAND gates 600 through 608. This enables the dot drivers and the output of the one shot 583 is also applied to one input of NAND gate 584 whose other input is controlled by the low enable signal via the print clock disable signal from the PIA 137 inverted via NAND gate 585. The inversion brings the output of NAND gate 584 low shifting the decoder 564 into the lower range of its outputs. If an up-date from the microprocessor 30 does not occur within the time frame set by the one-shot 583, its output will time out disabling the dot drivers in shifting the sentence select decoder 564 to its higher outputs which are not used thus disabling the sentence enable current sink transistors associated with its outputs. This protective feature gently enhances the reliability and maintainability of the circuitry of the present invention.

The motor drive circuitry of the present invention is associated with the carriage of block 57 of FIG. 1 which is used to physically move the sample with respect to the optics for scanning purposes. The motor control circuitry and carriage encoder functions are performed by the circuitry of FIGS. 25, 26 and 27. It will be understood that the microprocessor-controlled densitometer of the present invention will include two sets of such circuits, one set for each axis of carriage travel. The X axis is the scan direction or the left/right movement and the Y axis is the step direction or front-/back movement. To avoid duplication, the following discussion will deal only with the X axis but it is to be understood that similar circuitry is used for the Y axis control as well.

The motor control circuitry of FIG. 25 includes a clutch control circuit which includes a first input which is high when the clutch is on and a second input which is high when the other clutch is on. The first Clutch-on input is taken from the output of a buffer amplifier 640 whose input receives X MOTOR ON signal as hereinafter described and whose output is supplied to node 641. Node 641 is then connected to the Clutch ON input and supplied through a resistor 642 to the base of a transistor 643. The other Clutch ON input is connected through a resistor 644 to the base of transistor 643. Transistor 643 has its emitter connected directly to ground and its collector connected to the cathode of a light emitting diode (LED) 645 whose anode is connected to a +5 volt source of potential through a resistor 646. Associated with the LED 645 is a phototransistor 647 having its collector connected to a +16 volt source of potential through a resistor 648 and its emitter connected to the base of a Darlington driver transistor 649. The base of transistor 649 is connected to ground through a resistor 650 while the emitter is connected directly to ground. The collector of drive transistor 649 is connected to the clutch represented by block 651 and the other terminal of the clutch is connected directly to a +15 volt source of potential.

When the X MOTOR ON command from the PA0 of PIA 136 of FIG. 20 is transmitted to the circuit of FIG. 25, it is supplied to the input of an inverting buffer 640 and simultaneously through the parallel combination of a resistor 652 and capacitor 653 to a +5 volt source of potential. When the motor is to be turned ON, a low signal is transmitted from the PIA 136 to the input of the inverting buffer 640 causing the output at node 641 to go high. When the high at node 61 is transmitted through the Clutch-On lead and the current-limiting resistor 642, it drives the base of transistor 643 and brings transistor 643 out of cut-off and into conduction. With transistor 643 conducting, the +5 volt source of potential supplies current through resistor 646 and the LED 645 causing LED 645 to emit light. The emitted light is detected by the base of phototransistor 647 since they are optically coupled together and causes the phototransistor 647 to conduct. Current flows from the +16 volt source of potential through resistor 648 and the conducting phototransistor 647 to the base of drive transistor 649 causing it to conduct. With transistor 649 turned ON, conducting current will be supplied from the +16 volt source through the clutch 651 to ground via transistor 649. In the OFF condition, the base of drive transistor 649 is pulled low by resistor 650 to keep the transistor in cut-off and remove current flow from the windings of the clutch 651.

In addition to the X MOTOR ON signal input from the PIA 136 of FIG. 20 which is supplied to the input of inverting buffer 640, the LEFT/RT directional signal is supplied from the PAI output of PIA 136 to the input of an inverting buffer amplifier 654 and simultaneously to a +5 volt source of potential through the parallel combination of the resistor 655 and a capacitor 656. The output of the inverter 654 is connected to the input of a second inverter 655 and to one input of a four-input NAND gate 656. The output of inverter 640 which is taken from node 641 is connected as the second input of NAND gate 656 while the output of inverter 655 is connected as one input of a second four-input NAND gate 657. The output of NAND gate 656 is connected to the input of an inverting buffer 658 whose output is connected to the input of a NAND gate driver 659 whose output is connected to the cathode of an LED 660 whose anode is connected to a +5 volt source of potential through a resistor 661.

A phototransistor 662 is optically coupled to the LED 660 and receives the radiation emitted therefrom at its base. The collector of phototransistor 662 is connected to a +16 volt source of potential through a resistor 663 while the emitter is connected directly to the base of the transistor 664. Transistor 664 has its emitter connected directly to ground and its collector connected to a voltage divider node formed at the junction of a first resistor 665 whose opposite terminal is connected to a +16 volt source of potential and a second resistor 666 whose opposite terminal is connected directly to the base of a transistor 667. Transistor 667 has its emitter connected to ground and its collector connected via lead 668 through a resistor 669 to the base of the Darlington transistor 670 to be hereinafter described.

The collector of transistor 667 is also connected to a +16 volt source of potential through a resistor 671 and through a resistor 672 to the base of a transistor 673. The emitter of transistor 673 is connected to ground and a capacitor 674 is connected between the base of transistor 673 and ground. The collector of transistor 673 is connected to a +16 volt source of potential through a resistor 675 and is also connected through a resistor 676 to the base of a Darlington-type transistor 677. The collector of Darlington transistor 677 is connected via lead 678 which connects to other circuit components as hereinafter described while the emitter of transistor 677 is connected via lead 679 to a node 680 as hereinafter described.

The output of the four input NAND gate 656 is also connected as one input of a two input NAND gate 681 whose output is connected to the "A" input of a one-shot 682. The Q output of the one-shot 682 is connected via lead 683 to one input of a logical NAND gate 684 and to the A input of a second one-shot 685. The Q output of the one-shot 685 is connected to both inputs of the two input NAND gate 686 and to the input of a NAND gate buffer 687 whose output is connected to the cathode of an LED 688 whose anode is connected through a resistor 689 to a +5 volt source of potential. The LED 688 is optically coupled to a phototransistor 690 and the collector of the photo transistor 690 is connected to a +16 volt source of potential to a resistor 691 while the emitter is connected directly to the base of a transistor 692. The emitter of transistor 692 is connected directly to ground while the collector is connected to one terminal of a relay coil 693 whose opposite terminal is connected to a +16 volt source of potential and a diode 694 is connected across the coil 693 with its anode coupled to the collector of transistor 692 and its cathode connected to the +16 volt source of potential. The relay coil 693 is used for operating a switch member 723 associated therewith as indicated by the dotted line through the coil 693 as hereinafter described.

The output of the two input inverting NAND gate buffer 686 is connected to the second input of NAND gate 684 and the output of NAND gate 684 is connected directly to the input of an inverting amplifier 695. The output of the inverter 695 is connected to another input of the four input NAND gate 657 and to the third input of NAND gate 656. The output of NAND gate 657 is connected directly to the input of an inverter 696 whose output is connected to the input of a NAND gate driver 697. The output of the NAND gate driver 697 is connected to the cathode of an LED 698 whose anode is connected to a +5 volt source of potential through a resistor 699. A phototransistor 700 which is optically coupled to the LED 698 receives the light emitted therefrom at its base and has its collector connected to +16 volt source of potential through a resistor 701 and its emitter connected directly to the base of a transistor 702. The emitter of transistor 702 is connected to ground and the collector is connected through a resistor 703 to the base of a transistor 704. Transistor 704 has its emitter connected directly to ground and its collector connected to a +16 volt source of potential through a resistor 705. The collector of transistor 702 is also connected to a +16 volt source of potential through a resistor 706. The output of the NAND gate 657 is connected as one input of NAND gate 657, is connected as one input of NAND gate 681, and is the fourth and last input of the four input NAND gate 656 while the output of NAND gate 656 is connected as the second input of NAND gate 681 and as the fourth and last input of the four input NAND gate 657.

A +16 volt source of potential is coupled to ground through a capacitor 706 and is also connected to one terminal of a resistor 707 whose opposite terminal is connected to the cathode of the zener diode 708 whose anode is grounded. The junction of the cathode of the zener diode 708 and the resistor 707 is connected to one terminal of a trim resistor or potentiometer 709 whose opposite terminal is grounded. The potentiometer tap or wiper arm 710 is connected through resistor 711 to the non-inverting input of an operational amplifier 712 and the non-inverting input is also coupled to ground through a capacitor 713. The output of the operational amplifier 712 is taken from node 714 and node 714 is connected to the anode of a diode 715 whose cathode is connected directly to the base of a Darlington-type transistor 716. The collector of transistor 716 is connected to the +16 volt source of potential while the emitter is connected to the collector of transistor 670 and the collector of still in another Darlington-type transistor 717. The emitter of transistor 716 is connected through a resistor 718 back to the inverting input of the amplifier 712. The inverting input of the amplifier 712 is also connected through a capacitor 719 to the output node 714.

The collector of transistor 670 is connected to the emitter of transistor 716 and the collector of transistor 717 while the base is connected via resisto 669 and lead 668 to the collector of transistor 667. The emitter of transistor 670 is connected to the anode of a diode 720 whose cathode is connected to a normally-closed switch contact terminal 721. The normally-closed switch contact terminal 721 is connected directly to the emitter of still another Darlington-type transistor 722. A relay-operated switch member 723 is normally cloed upon contact 721 and is connected to one plate of a capacitor 724 and to one terminal of an inductor or motor drive coil 725. The opposite terminal of the coil 725 and the opposite plate of capacitor 724 is connected to node 680. As previously described, node 680 is connected via lead 679 to the emitter of transistor 677 and it is also connected to a normally-opened switch contact terminal 726 and to the cathode of a diode 727 whose anode is connected to the emitter of transistor 717. The switch member 723 is positioned between the normally-closed switch contact 721 and the normally-opened switch contact 726 under control of the relay coil 693 previously described.

The collector of transistor 704 previously described is also connected through a resistor 728 to the base of transistor 717 and the collector of transistor 717 is connected to the collector of transistor 670 and the emitter of transistor 716 and the emitter is connected to the anode of diode 727 as previously described. The collector of transistor 704 is also connected through a resistor 729 to the base of the transistor 730 and the base is also coupled to ground through a transistor 731. The emitter of transistor 730 is grounded while the collector is connected to a +16 volt source of potential through a resistor 732 and to the base of transistor 722 through a resistor 733. As previously described, the emitter of transistor 722 is connected to the normally-closed switch contact 721 while the collector is connected via lead 678 to the collector of transistor 677 and through a resistor 734 to the inverting input of an operational amplifier 735. The non-inverting input of amplifier 735 is connected to ground through a resistor 736 and the output is taken from node 737. Negative feedback is provided from the output node 737 to the inverting input through the parallel combination of a capacitor 738 and a series path including a first resistor 739 and a trim resistor 740. The inverting input of amplifier 735 is connected to one terminal of the trim resistor 740 and to its associated wiper arm for providing negative feedback to the amplifier 735. Output node 737 is connected through a resistor 741 to the inverting input of amplifier 712 to complete the overall description of the structure of the circuit of FIG. 25. The function of circuit of FIG. 25 will now be described briefly herein below.

At the isolated ground system interface represented by the dotted blocks 742 and 743 which contain the LED's and associated phototransistors which provide the optical coupling between the circuit portions, the outputs are a Right Enable Signal at the emitter of phototransistor 662; a Left Enable Signal at the emitter of phototransistor 700; and a Brake Enable at emitter of phototransistor 690. The input from the processor system includes a low enable on signal (the signal $\overline{\text{X MOTOR ON}}$) and a direction control line (LEFT/$\overline{\text{RT}}$). Therefore, this on/off and direction and control requires transformation into the proper signal levels and this is performed by the TTL logic circuitry of FIG. 25.

The main element involved with either direction enable signal is the four input NAND gate 656 or 657. These NAND gates provide a low enable output which is inverted by inverter 658 or 696, respectively. The outputs inverters 658, 696 provide a high enable output into the open collector buffers 659, 697 respectively and the outputs of the buffers 659, 697 are low which sinks current through resistors 661, 699 to cause the LED's 660, 698 to conduct turning on their associated phototransistors 662, 700, respectively, by optical coupling with the LED's 660, 698 in the current path.

In order for one of the four input NAND gates 656 or 657 to activate a motor on, four conditions must be met, i.e., all inputs must be high. The first condition is that the other direction cannot be on which is provided by cross coupling at the outputs and a second condition is that a Brake Enable signal is not present which is the output of inverter 655 whose output is supplied as an input to both of the NAND gates 656 and 657. The third condition is that an on command from the processor exists which is a low enable input to the buffer inverter 640. When this input is pulled high and filtered by the RC combination comprising resistor 655 and capacitor 656, it is supplied to the input of the buffer 640 giving a high enable output which is applied to the quad input NAND gates 656 and 657. The fourth and final condition or input is the direction control signal from the microprocessor 30 which, like the on/off control is pulled high and de-glitched by the combination of resistor 655 and capacitor 656. This input is also applied to an inverter 654 for buffering and the output of this buffer is a high enable for one direction and is applied to quad input NAND gate 656 but it is also inverted by the inverting buffer 655 so the opposite signal is supplied as one input of the quad NAND gate 657. In this manner, the direction control is to decided by which quad input NAND gate is enabled and a redundant "Exclusive or" check is provided. This gives a brief description on the control signal derivation.

The brake signal is given when any motion command is terminated. This is decoded by the NAND gate 681. When the motion command is terminated, both inputs of NAND gate 681 go high allowing the output to go low and a low at the output of NAND gate 681 will trigger the one shot 682. The $\overline{Q}$ output of the one shot will inhibit further motion commands through NAND gate 684 and inverter 695 bringing one of the inpus of each of the quad input NAND gates 656, 657 low. The falling edge of this $\overline{Q}$ output will also trigger the brake one-shot 685. The $\overline{Q}$ output of the brake one-shot 685 will enable the optoisolator comprising LED 688 and phototransistor 690 via the inverting buffer 687. The $\overline{Q}$ output is also inverted by NAND gate 686 and applied to the input of NAND gate 684 to inhibit further motion commands. This redundancy is included to prevent the motion commands from being valid in the event one of the two one-shots 682, 685 had triggered off of a noise spike. The on inhibit and brake one-shots 682 and 685, respectively, are maintained separate to allow the brake relay to reset prior to resuming motion.

The isolated ground system switching and regulation circuitry of FIG. 25 will now be described. The transistor switching on the isolated ground system will be discussed to include braking, each direction enable, and the devices associated with motor speed control. When the brake signal is active, phototransistor 690 is on applying a +16 volts to the base of transistor 692 through the current-limiting resistor 691. This turns transistor 692 on allowing it to sink current through the relay coil 693. Thus energizing the relay coil 693 shorts the motor power input leads together as it disconnects power and when the control one-shot 682 times out, transistor 692 turns off releasing the relay coil 693. Diode 694 clamps the inductive kick to the +16 volts supply level protecting transistor 692 from damage.

The action of LED 698 and phototransitors 700 being enabled for the left direction drive applies +16 volts to the base of transistor 702 through current limiting resistor 701. This causes transistor 702 to switch to a conductive state which in turn turns transistor 704 off bringing its collector potential high. The high potential at the collector of transistor 704 is applied to the base of the power driver transistor 717 through curent-limiting resistor 628. Transistor 717 conducts and power is now applied to one side of the motor windings by the emitter of transistor 717 through blocking diode 727.

When the collector of transistor 704 goes high turning transistor 717 on, the RC network of resistor 729 and capacitor 731 starts to charge. As this RC network charges, the base drive of transistor 730 will be increasing bringing it slowly into conduction. This gradually brings the base of the ground return transistor 722 slowly to ground. As the base of the ground return transistor 722 approaches ground, it will slowly start to conduct to afford a soft start-up for the motor. This prevents some of the ground and supply transients from appearing and the ground return for the motor is through the emitter of transistor 722 and out the collector to ground through the current sense resistor 744.

To drive in the opposite direction, the same sequence takes place through transistors 664, 667 and 673 for the power driving transistor 670, the blocking diode 720 and the ground return transistor 677. The RC network in the base of the ground return driver for both transistor 677 and transistor 722 also ensures that the power drive is off first thus relieving the relay 693 from interrupting motor currents. This turn-off time constant is not as long as the turn-on as the capacitor is discharging through the base of transistors 730 or 673.

The speed control circuit controls the voltage applied to the power drivers 670 and 717 and thus the DC motor represented by the coil 725. The basic voltage regulator, operational amplifier 712 in combination with the driver transistor 716, are controlled by the zenered reference and feedback amplifier 735. The zener reference includes a zener diode 708 with resistor 707 limiting the avalanche current through the diode. The zener potential is applied to the trim resistor 709 for speed control adjustments and the wiper 710 of the trim resistor 709 is applied to the non-inverting input of the amplifier 712 through the RC filter network comprising resistor 711 and capacitor 713. The feedback for the amplifiers obtained at the output of the series pass element comprising driver transistor 716 by resistor 718 returning to the inverting input of the amplifier 712. Diode 715 prevents the base of the series past transitor 716 from receiving a negative potential and capacitor 719 slows the loop time down. In operation, amplifier 712 will drive the base of the series pass element 716 to provide the proper output voltage and the speed may be adjusted by the trim resistor 709 for fine adjustments.

The current sense amplifier 735 amplifies the voltage developed across resistor 744 in the ground return path for the motor. The gain of this amplifier stage is adjustable and resistor 736 reduces the effects of input bias current. In operation, the output of the current sense amplifier 735 will drop the reference point for the voltage divider comprising resistors 741 and 718. As the motor runs, a positive voltage is developed at resistor 744 and amplified by the current sense amplifier 735. The output of the amplifier 735 is somewhat negative and as the motor load is increased, the current drawn by the motor increases presenting a higher voltage across resistor 744. This is in turn a more negative voltage at the bottom of the voltage divider which reduces the potential of the inverting input of the regulator amplifier 712. This action increases the base drive to the series pass transistor 716 thereby supplying a higher potential at its emitter for the sensed increased load.

This concludes the description of the motor control circuitry of FIG. 25 and the operation thereof and since all of the components used in the circuit are conventional off-the-shelf items, the above description should be more than adequate but it should be recognized that any conventional motor drive system and any conventional motor drive control circuit therefor can be used in the system of the present invention for selectively positioning the carriage as desired.

Figure 26:
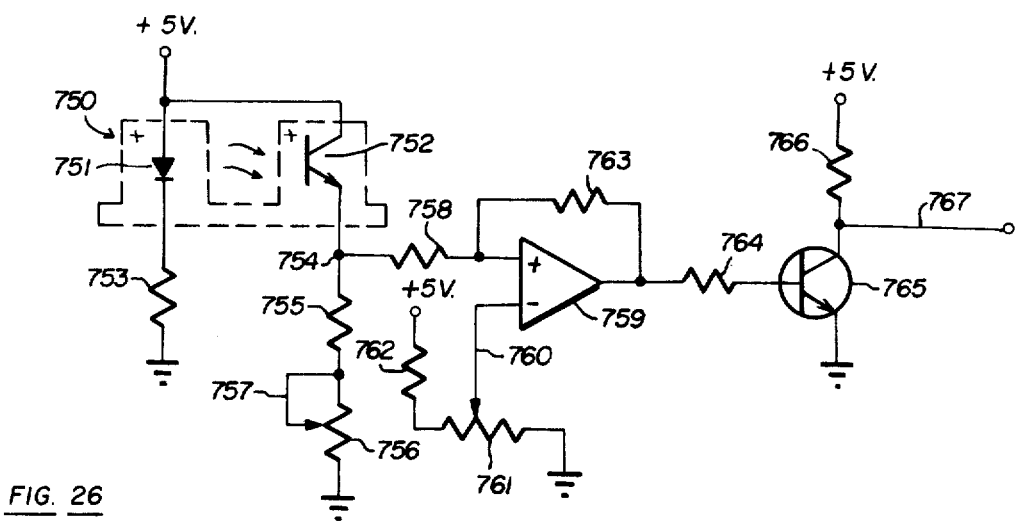
FIGS. 26 and 27 are electrical schematic diagrams of the carriage position encoder circuits for determining the X-axis position of the carriage of block 57.
Figure 27:
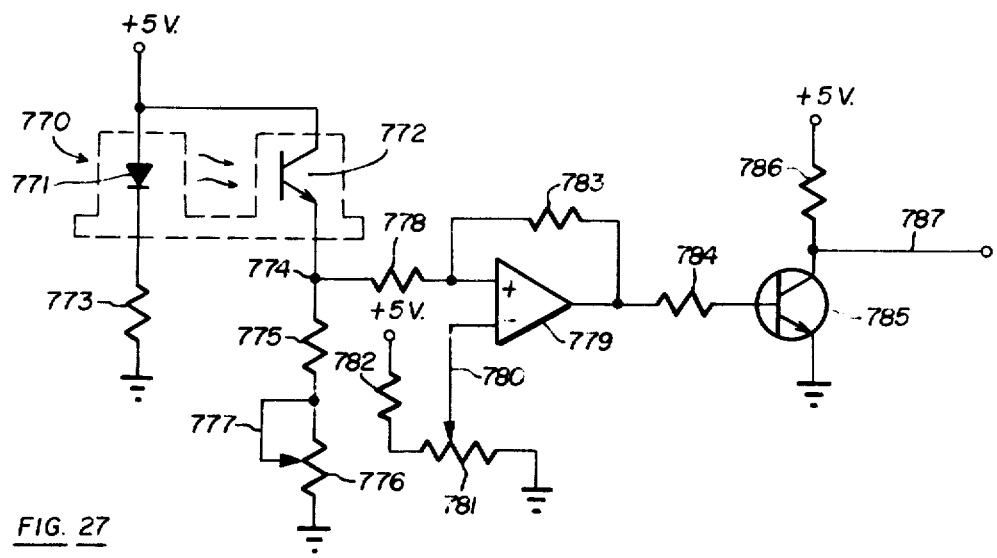

The carriage encoder circuitry is shown in FIGS. 26 and 27 for the "X" position signal supplied to the main chassis keyboard control logic as hereinafter described. A duplicate set of encoders, now shown but substantially identical to those of FIGS. 26 and 27 will be used for the "Y" positional information. Since the circuits of FIGS. 26 and 27 are substantially identical, the circuit of FIG. 26 will be described and the circuit of FIG. 27 will be given corresponding reference numerals corresponding to those of FIG. 26 but twenty numbers higher.

The carriage encoders of FIGS. 26 and 27 develop signals which are used to convey the actual current direction and position of the carriage to the processor 30. This is performed by optical switches represented by the dotted blocks 750, FIG. 26, and 770 of FIG. 27. A slotted disc, not shown but conventional in the art, is mounted on the actual drive mechanism and the signals produced by the optical switches 750, 770 which straddle the slotted disc or manipulated by the logic circuits as hereinafter described. The optical switch 750 is constructed such that one leg of the optical switch 750 includes a light emitting diode 751 and the other leg contains a phototransistor 752. In the preferred embodiment of the present invention, the optical switch assembly 750 and 770 are conventional SPX 2762 optical switch elements and the viewing angle of the phototransistors 752, 772 is restricted to approximately a 0.009 inch slit. As the slotted disc rotates in the space between the LED 751 and the phototransistor 752, the phototransistor is interrupted alternatively by bars and slits. This produces a sine wave output at the emitter of the phototransistor as known in the art.

The structure of FIG. 26 has the anode of the LED 751 connected directly to a +5 volt source of potential and its cathode connected to ground through a resistor 753. The anode of LED 751 also supplies the +5 volt source of potential to the collector of the phototransistor 752 and the emitter of transistor 752 is coupled to an output node 754. Node 754 is connected to one terminal of a resistor 755 whose opposite terminal is connected to a first terminal of a trim pot or trim resistor 756 whose opposite terminal is connected to ground. A potentiometer wiper arm extends from the junction of resistor 755 and the trim resistor 756 so that its wiper arm may be selectively positioned along the potentiometer 756 to vary the resistance thereof and thus the voltage at node 754. Node 754 is connected through a resistor 758 to the non-inverting input of an operational amplifier 759 and the inverting input of operational amplifier 759 is connected to the potentiometer wiper arm 760.

The potentiometer wiper arm 760 is selectively positionable along a potentiometer or trim resistor 761 having one terminal connected to ground and its opposite terminal connected to a +5 volt source of potential through a resistor 762. The output of the operational amplifier 759 supplies positive feedback to the non-inverting input through a resistor 763. The output of the amplifier 759 is also connected through a resistor 764 to the base of transistor 765. The emitter of transistor 765 is grounded and the collector is connected to a +5 volt source of potential through a resistor 766. The output of the circuit which supplies the positional information to the circuitry described hereinafter is taken from the collector and supplied thereto via lead 767.

The operation of the circuits of FIGS. 26 and 27 will now be described with specific reference to the "X" positional information but it is to be understood that a pair of similar circuits provide the required "Y" positional information. As the optical switches 750 (770) produce the sine wave output at the emitter of phototransistors 752 (772) due to the rotation of the slotted disc alternatively passing and blocking the light from the LED 751 (771) to the base of the phototransistor 752 (772) as conventionally known. This sine wave output is supplied to the output node 754 (774). Power is supplied to the circuit as the +5 volt source as applied to the anode of the LED 751 (771) and the collector of the phototransistor 752 (772). The LED current is limited by the current limiting resistor 753 (773).

The phototransistor signal at the output node 754 (774) is developed across resistors 755 (775) and trim resistors 756 (776) and this output signal is supplied from the output node 754 (774) through isolation resistor 758 (778) to the inverting input of the operational amplifier 759 (779). To provide positive switching the amplifier 759 (779) is operated in an open loop mode with positive feedback provided by the feedback resistor 763 (783). The reference or switching point threshold is determined by the voltage divider combination which includes a resistor 762 (782) and trim resistor 761 (781) across the +5 volt supply.

The output of the operational amplifier 759 (779) provides base drive current to the output transistor 765 (785) and the transistor switch output is obtained at the collector thereof which is supplied with power from the +5 volt source of potential through the resistor 766 (786). The collector output of the transistor 765 supplies its output signal via lead 767 while the collector output of transistor 785 supplies its output via lead 787 to circuitry to be hereinafter described for the purpose of providing carriage encoder feedback signals which convey both directional and positional carriage information back to the microprocessor 30 as hereinafter described with reference to the circuit of FIG. 35.

Figure 19:
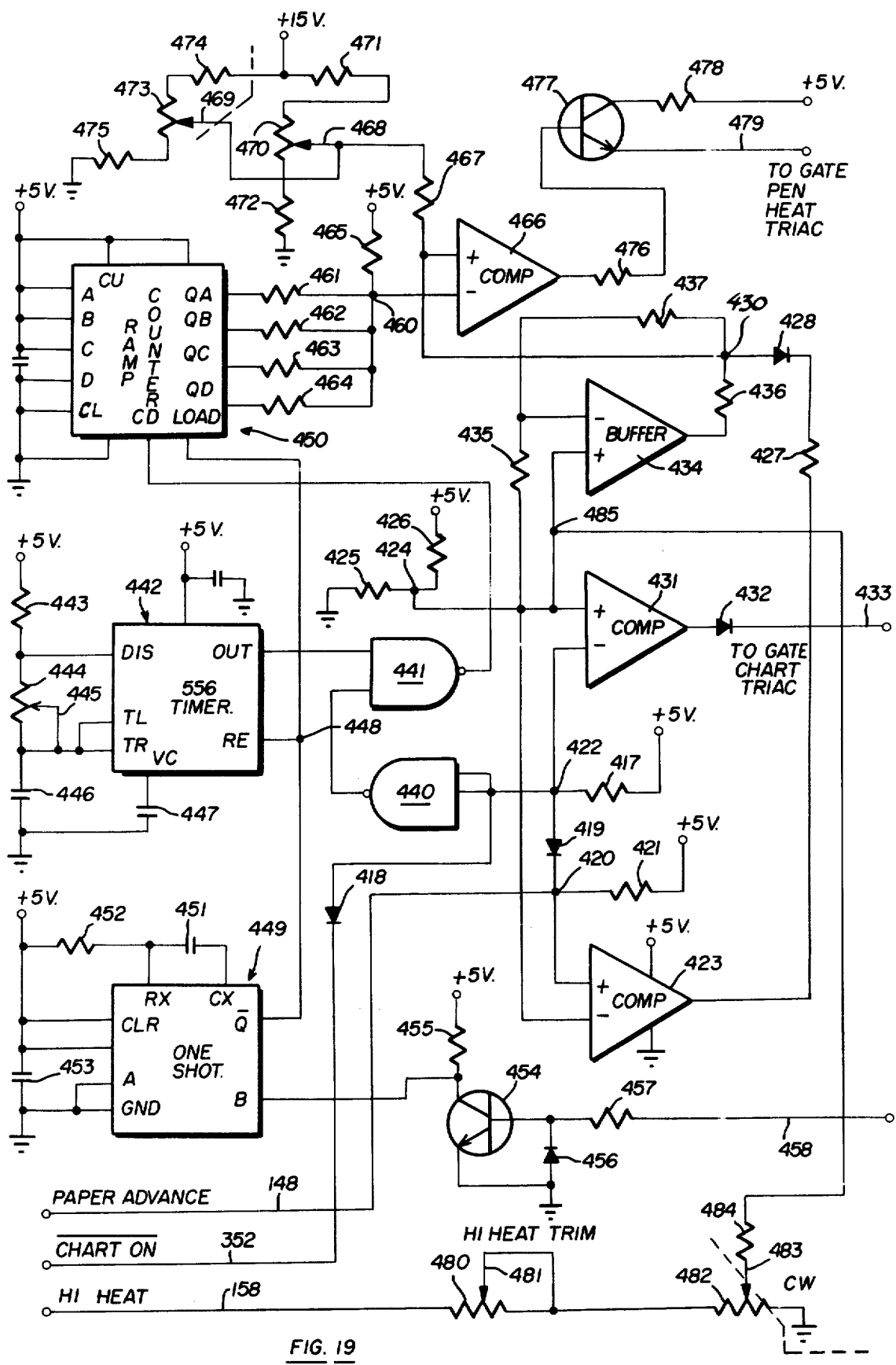
FIG. 19 is an electrical schematic diagram of still another portion of the pen driver circuitry associated with block 50 of FIG. 1.
Figure 28:
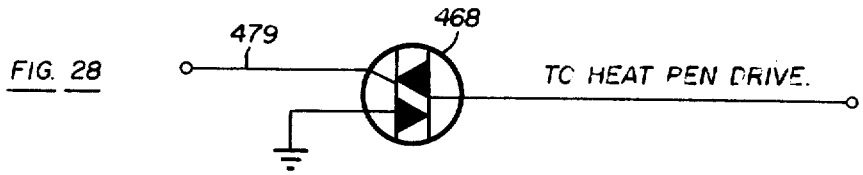
FIGS. 28 and 29 are triac control circuits used to control the heat pen drive and chart motor drive, respectively.
Figure 29:
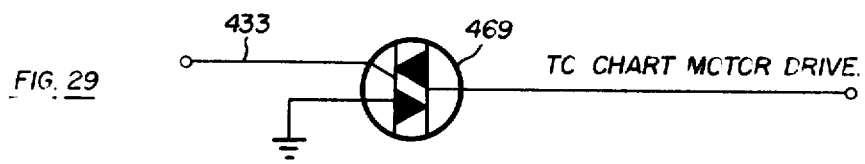

The circuits of FIGS. 28 and 29 are the triac drive circuitry used to drive the heat pen and the chart motor referred to in the description of FIG. 19. The output of the drive transistor 477 of FIG. 19 supplies the heat pen control signal via lead 479 to the gate of a triac 468 and the triac output is used to control the power supply to the heat pen driver, as conventionally known in the art. Since the circuitry of FIG. 19 controls the point in the AC cycle waveform with which the comparator 466 trips to operate transistor 477, the triac 468 will be synchronized to various points in the AC cycle to control the amount of power supplied to the heat pen driver, as conventionally known in the art. Similarly, the output of comparator 431 of FIG. 19 is supplied through diode 432 and lead 433 to the gate electrode of a triac 469 and the output of the triac 469 is used to control the chart motor drive. Again, since the output of comparator 431 toggles back and forth as the trip point is exceeded, triac 469 will be turned on at differing points in the AC waveform thereby controlling the amount of power supplied to the chart drive motor, as conventionally known in the motor control art.

The circuitry associated with the remote keyboard represented by block 44 of FIG. 1, includes two major portions. One circuit portion relates to the keyboard functions themselves while the other portion relates to a recirculating memory used with the display portion of the package represented by block 40 of FIG. 1. The memory system of FIG. 30 will be discussed first followed by a description of the keyboard circuitry of FIG. 31. At the heart of the recirculating memory display control system is a random access memory RAM 790 which, in the preferred embodiment of the present invention, is a conventional Motorola MC6810 RAM organized to have the capacity of 128 words each of which is eight bits wide. The addressable inputs of the memory 790 are designated A0 through A6 but only addressed inputs A0 through A4 are active since address inputs A5 and A6 are grounded. Similarly, the data outputs of the memory 790 are designated D0 through D7 but only data outputs D0 through A5 are active since data outputs D6 and D7 are grounded.

Since the basic operation of a random access memory was previously described with reference to FIG. 5, only a brief description will be given herein as it relates to the remaining circuitry of FIGS. 30 and 31. The display enabled input $\overline{\text{EN DISPLAY}}$ is supplied from the CA2 output of PIA 138 of FIG. 21 with a low signal representing a run condition and a high signal representing a low condition. The signal $\overline{\text{EN DISPLAY}}$ is connected to the input of an inverting buffer amplifier 791. Its output is connected (1) to the cathode of a clamping diode 792 whose anode is grounded; (2) to the read/write input R/W of the RAM 790; (3) to the L=BLANK output of the Burroughs Self-Scan display panels, not shown, but known in the art, and represented by block 40 of FIG. 1; (4) to one input of a logical NAND gate 793 which is part of a quad NAND gate package 797 which includes four two-input NAND gates 793, 794, 795 and 796; (5) to the "2B" input of the one shot multivibrator 798; (6) to the "1A" input of the one shot multivibrator 799; and (7) to the "1B" input of the one shot multivibrator 800.

The STEP signal is supplied to the circuit of FIG. 30 from the CB2 output of PIA 138 of FIG. 21 and connected through the parallel combination of a resistor 801 and a capacitor 802 to a +5 volt source of potential and simultaneously to one input of NAND gate 794. The DATA UPDATE output signal from the Burroughs' self-scan display panel is connected to one input of NAND gate 793 and to the cathode of the clamping diode 803 whose anode is grounded. The output of NAND gate 793 is connected directly to the second input of NAND gate 794 and the output of NAND gate 794 is connected directly to the CS0 of the RAM 790 and to the 1A input of the number 1 Memory Address Control Counter 804.

The one shot multivibrator 798 has associated therewith a conventional RC external network including resistor 805 and capacitor 806 for establishing the timing period of the one shot as conventionally known. The $\overline{Q}$ output of the one shot 798 is connected as one input of a logical NAND gate 807. A second one shot multivibrator 791 is also supplied with the conventional RC network including resistor 808 and capacitor 809 for establishing the timing period thereof. The $\overline{Q}$ output supplies the second input of NAND gate 807 and the output of NAND gate 807 is connected to both inputs of a two input NAND gate 810 which acts as a buffer inverter and its output is connected directly to one input of a NAND gate 795.

The third one shot multivibrator 800 also has as its associated therewith a conventional RC network including resistor 811 and capacitor 812 for establishing the timing cycle thereof as conventionally known. The $\overline{Q}$ output of the one shot 800 is connected to the second input of NAND gate 795 and the output of NAND gate 795 supplies the RESET signal to the R01 input of the MAC counter 804; to the R01 input of the second MAC counter 813; and to the input of a buffer inverter 814 whose output is connected to the cathode of a clamping diode 815 whose anode is connected to ground and whose output is also connected to supply the RESET signal to the Burroughs' self-scan display panel previously described.

The number 2 memory address control counter 813 has its A output connected to one input of NAND gate 796 and to the A2 address input of the RAM 790. The "1A" output of counter 813 is connected directly to the "D" output of counter 804 and to the "A3" address input of RAM 790. The second input of NAND gate 796 is connected to the "C" output of counter 804. The output of NAND gate 796 is connected directly to the "1A" input of the one shot 800. The "1A " input of the number 2 MAC counter 813 is connected to the "D" output of the number 1 MAC counter 804.

The outputs of the number 1 Memory Address Control Counter 804 are connected as follows. The "A" output is connected back to the "1B" input of counter 804 and to the A0 data input of RAM 790. The "B" output of counter 804 is connected directly to the A1 input of RAM 790 and the "C" output of counter 804 is connected both to one input of NAND gate 796 and to the "A2" input of RAM 790. The "B" output of counter 804 is connected both to the "1A" input of the number 2 Memory Access Control Counter 813 and to the "A3" input of RAM 790. The "A4" input of the RAM 790 is connected to the "A" output of the number 2 Memory Address Control Counter 813 which connects to the other input of NAND gate 796 as previously described.

A display clock 815 is formed from a conventional 555 timer and used to deliver input pulses to the Self-Scan Display Panel previously described. The clock or timer 815 is conventional and includes the external RC network comprising resistor 816, trim resistor 817 and capacitors 818 and 819. Resistor 816 has one terminal connected directly to a +5 volt source of potential which is also supplied to the RE and VCC inputs of the timer 815. The other terminal of resistor 816 is connected to one terminal of the trim resistor or trim pot 717 whose opposite terminal is commonly connected to the PH and TR inputs of the timer 815. The potentiometer wiper arm 820 is connected from the opposite terminal of the trim resistor 817 and used to vary the resistance in the circuit by its position along the potentiometer resistor 817 as known in the art. The opposite terminal of trim resistor 817 is also connected to ground through a capacitor 818. The CV input of the timer 815 is connected to ground through a capacitor 819 and the output OUT supplies the display clock pulses to the Burroughs' Self-Scan Display Panels previously described. In the preferred embodiment of the present invention, the one shot multivibrator 798, 799 and 800 are conventional, off-the-shelf 7493 devices. As previously described, the timer 815 is a standard 555 unit and the RAM 790 is a conventional MC 6810 device.

The operation of the recirculating memory and display control system of FIG. 30 will now be described briefly. As mentioned above, the random access memory 790 is organized into 128 words each of which is eight bits wide. A total of 20 locations are used and only six of the eight bits available are used. The memory addresses are controlled by the Memory Address Control Counters 804 and 813 with the rest of the circuitry generating the reset pulses and chip select signals. The RAM 790 has two operating states. One is the "load" condition where the RAM is being loaded or written into and the second condition is the "run" state where the memory is presenting data to the display. These conditions will be briefly discussed in that order.

To begin the Load Cycle, the input EN DISPLAY will go high and when this signal is applied to the inverting buffer 791, the output goes low and is used to blank the display as known in the art. This low is also applied to the RAM 790 at the R/$\overline{\text{W}}$ input placing the RAM 790 in the write mode. The signal at the output of the inverting buffer 791 is also applied to the "1A" input of the one shot 799 causing it to generate a ten microsecond RESET pulse through NAND gate 707, 810, and 795 and the RESET signal is applied to the counters 804, 813.

With the Memory Address Control Counters 804 and 813 RESET to zero, the address of the memory location to be written into first is zero. The low load signal from the output of buffer amplifier 791 is also applied to one input of NAND gate 793 forcing its output high to enable NAND gate 794 to pass the input signal STEP, when required, from the PIA 138, FIG. 21, as previously described. Data is then presented by the processor 30 to the inputs D0 through D5 via he PB0 through PB5 outputs of PIA 138. This data will be the first display position character in a modified ASCII format. The input data requiring a low, forward biases the blocking diodes 840 through 845 as required. The data is thus applied to the D0 through D5 inputs of RAM 790 and written into the selected address therein.

The processor 30 now gives a STEP command which is applied to the other input of NAND gate 794 to produce a high output. When the output of NAND gate 794 goes high, the CS0 input of the RAM sees a negative edge and stores the data into the memory. This negative edge is also applied to the number 1 memory address control counter 804 via the "1A" input. This will increment the count stored in the counter 804 causing the next memory location in RAM 790 to be addressed. As this sequence continues for each memory location count, the number 1 MAC counter 804 will eventually reach a count of binary 1111. The next count input pulse will bring about a count of 0000. The "D" output of the counter 804 going low increments the number 2 MAC counter 813 in the incremented count appears at the "A" output thereof.

When "A" output of counter 813 goes high and is supplied to the A4 address of RAM 790, it allows the remaining or upper memory locations to be accessed as required. This process continues until the processor 30 has written all 20 characters for the display into the RAM 790. When this has been done, the processor 30 writes the data at inputs D0 through D5 high for the blocking diodes 840 through 845, respectively, and brings the Load signal at the input of the inverting buffer 791 low for the run mode. The rising edge at the output of the inverting amplifier 791 is applied to the "2B" input of one shot 798 causing it to produce a timed ouput pulse. The RESET pulse from the Q output of the one shot 798 is applied to the MAC counters 804 and 813 through NAND gates 807, 810 and 795 as previously described to cause the counters 804 and 813 to be RESET to 0000 ready to display the first memory location addressed. This RESET pulse is also applied to the display RESET input as the signal RESET via the output of the inverting buffer 714.

As the load signal is brought low, the output of the inverting buffer 791 goes high to bring the display out of the blank mode. The RAM 790 is brought back into the read mode via the R/$\overline{\text{W}}$ input. Therefore, the first data is presented at the data outputs D0-D5 of the RAM 790 and applied to the Self-Scan Display Panel as the signals B1, B2, B4, B8, B16, and B32, respectively. The display, having been RESET from the signal at the output of the buffer inverter 814 is now ready to display the first character. The display clock 815 delivers the input pulses to the display and these pulses are used to develop certain signals required within a display. After the first character display time, the display outputs a data update pulse which is supplied back to one input of NAND gate 793. With this input signal going low, a falling edge is produced at the output of NAND gate 794. This in turn clocks the number 1 Memory Address Control Counter 804 to the next address as well as disabling the outputs of the RAM 790 by a low at the CS0 input. As the data update pulse goes back high, the CS0 output is brought high causing the data for this address to be presented to the display for its display time. The display cycle is thus repeated for each of the remaining characters.

As the characters are clocked out by the operation of the counter 804, it will eventually increment until a binary count of 1111 is reached. The next count input pulse will produce a count 0000 and the falling edge at the "D" output will increment the counter 813. This brings the "A" output of counter 813 high setting the A for address line of the RAM 790 high for the remaining characters thereby enabling the higher address basis of the memory to be accessed. This also sets the input of NAND gate 796 high. As the count on the number 1 MAC counter 804 increases to 4 (binary 0100) the "C" output will go high. When this occurs the other input of NAND gate 796 goes high and the output falls. The low at the output of NAND gate 796 is supplied to the "1A" input of the one shot 800 whose "B" input is already high by virtue of the run mode. This enables the one shot 800 to produce a three microsecond pulse at the $\overline{\text{Q}}$ output. This pulse is applied through NAND gate 795 to RESET the counters 804 and 813 to a 0000 state. The other input of NAND gate 795 is already high since the other two one shots 798 and 799 have already timed out. This process continues until the processor 30 enters another load cycle.

The display clock 815 has associated therewith a RC network for establishing the timing thereof as conventionally known. The RC network includes resistors 816 and 826, trim resistor 817 and timing capacitor 818. The trim resistor 817 should be adjusted such that the output waveform of the timer is high for approximately 70 microseconds and has a total cycle time of approximately 110 microseconds.

The clamp diodes 792, 803 and 825 are protective devices installed to aid in preventing damage to the inverting buffers 791 and 814 and to the NAND gate 793. This damage can occur if the large negative supply has not been bled down prior to disconnecting the display. The pull-up resistor 801 at the input of NAND gate 794 which receives the STEP signal from the PIA 138 is bypassed by a capacitor 802 which removes some of the high frequency transients. These transients can cause the NAND gate 794 to produce extra count pulses which are supplied to the counter 804. This will clock extra or false data into the RAM 790 resulting in an undesirable display but the RC combination of resistor 801 and capacitor 802 eliminates or at least minimizes this possibility. This completes the discussion of the Self-Scan Display refresh circuitry and both the load and the run cycles have been discussed. While the specific interface circuitry has not been specifically covered, it is conventionally known as is the Burroughs'

Self-Scan Display Panels used in the display of block 40 of FIG. 1.

Figure 31:
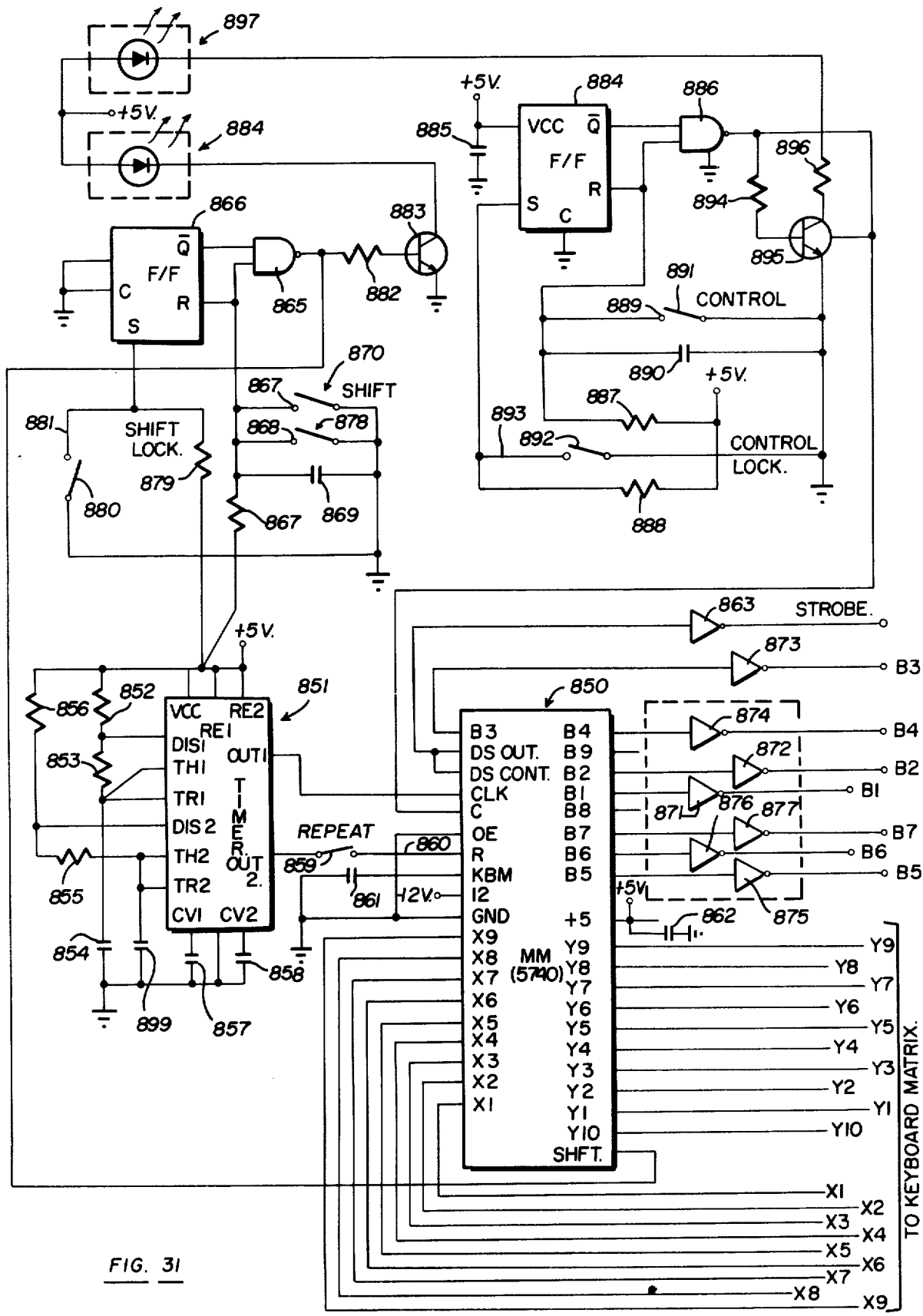
FIG. 31 is an electrical schematic diagram of the control circuitry for the remote keyboard of block 44 of FIG. 1.

The remote keyboard circuitry itself is represented by the circuitry of FIG. 31. The keyboard includes 61 keys of which 56 are data producing keys and the remaining 5 keys are used to modify the data. The basic system, in the preferred embodiment of the present invention, utilizes a conventional MM5740AA/F keyboard encoder 850. This encoder has 56 data keys arranged in the matrix on its input lines and the matrix is decoded when key closure is made and the appropriate output delivered to the processor system through the buffer network is hereinafter described. There are four other input circuits associated with the encoder 850 including the basic clock and repeat clock of module 851, the shift circuitry and the control circuitry hereinafter described.

The timer module 851 is, in the preferred embodiment of the present invention, a conventinal 556 dual timer integrated circuit package. The first side of the timer of clock module 851 has the VCC, RE1 and RE2 input connected directly to a +5 volt source of potential. The +5 volt source of potential is connected to the D1S1 input through a resistor 852 and then through a resistor 853 to both inputs DH1 and TR1 before being connected to ground through a capacitor 854. The TH2 and TR2 inputs are commonly coupled together and then through a resistor 855 are connected to the D1S2 input which is further connected through a resistor 856 to the +5 volt source of potential. The CV1 and CV2 outputs are coupled to ground through capacitors 857 and 858 respectively. The basic clock output from the first side of the timer, the output OUT 1 is connected directly to the clock input CLK of the encoder 850 while the output of the second side of the timer 851, the repeat clock output OUT 2 is connected to a positionable switch arm 859. The switch arm 859 is normally opened but may be closed on a contact lead 860 which is connected directly to the repeat input R of the encoder 850.

The encoder module 850 has its OE input and ground input connected directly to ground and its KBM input connected to ground through a capacitor 861. The −12 volt input is connected to a −12 volt source of potential and the +5 volt input is connected to a +5 volt source of potential and through a capacitor 862 to ground. The data strobe output DS out and data strobe control output DS CONT are commonly coupled together and connected to the input of an inverting bufer 863 which supplies the strobe signal to the CA1 input of PIA 138 of FIG. 21 and simultaneously to one terminal of the resistor R1 which forms a portion of the ganged resistor network of FIG. 21 as described previously.

The first seven key code outputs B1 through B7 of the encoder 850 are connected to inputs of inverting buffers 871 through 877, respectively and the outputs of these inverters supply the signals B1 through B7 to the inputs PA0 through PA 6, respectively of the Peripheral Interface Adapter 138 of FIG. 21. The encoder has the input keys arranged in a XY matrix from the outputs X1 through X9 and the inputs Y1 through Y10 and these inputs and outputs are shown as being associated with a conventional keyboard matrix system which is not shown but well known in the art. The shift output SHFT is connected to the output of a logical NAND gate 865 which has one input connected directly to the $\overline{Q}$ output of a conventional R/S flip-flop 866. The reset input R of flip-flop 866 is connected to the second input of NAND gate 865 and is also connected to a first terminal of a resistor 867 whose opposite terminal is connected to a +5 volt source of potential. The reset input R is also connected to a first normally open switch contact 867, to a second normally open switch contact 868 and to one plate of a capacitor 869 whose opposite plate is connected directly to ground. A first normally opened shift switch arm 870 which may be closed upon the normally open contact 867 is connected to ground as is a second switch arm 878 which can be closed upon the normally opened contact 868. The +5 volt source of potential is also connected through a resistor 879 to the set input S of the flip-flop 866 and ground is connected to a normally open switch arm 880 which can be closed upon a normally open Shift Lock contact 881 which is connected directly to the set S input of R/S flip-flop 886.

As previously described, the output of NAND gate 865 is connected directly to the shift input of the encoder 850 and is also connected through a resistor 882 to the base of the transistor 883, the emitter of transistor 883 is connected directly to ground and the collector is connected to the cathode of an LED 884 whose anode is connected to a +5 volt source of potential.

The control circuitry which is virtually identical to the shift circuitry including R/S flip-flop 866, NAND gate 865 and transistor 883 will now be described. A control R/S flip-flop 884 has its VCC input connected directly to a +5 volt source of potential and through a capacitor 885 to ground. The $\overline{Q}$ output of flip-flop 884 is connected as one input as a logical NAND gate 886 and the other input of NAND gate 886 is connected to the reset input R of the R/S flip-flop 884. The second input of NAND gate 886 which is coupled to the reset input R is also connected through a resistor 887 to a +5 volt source of potential. The +5 volt source of potential is further connected through a resistor 888 to the set input S of flip-flop 884. The reset input R is further connected to a normally open control switch contact 889 and through a capacitor 890 to ground.

A control switch arm 891 which is normally open but adapted to close upon the contact 889 is also connected directly to ground as is a control lock switch arm 892 which is normally open. The normally open Control Lock switch arm 892 is selectively closed upon the normally open switch contact 893 which is connected directly to the set input S of flip-flop 884. The $\overline{Q}$ output and the reset input R of flip-flop 884 are connected as both inputs of NAND gate 886 and the output of NAND gate 886 is connected through a resistor 894 to the base of a transistor 895 whose collector is connected through a resistor 896 to the cathode of an LED 897 whose anode is connected to a +5 source of potential. The emitter of transistor 895 is connected directly to ground as is the Control switch arm 891 and the Control Lock switch arm 892.

The operation of the circuitry of FIG. 31 will now be briefly described. The two clocks represented by the dual timer module 851 both have their reset inputs RE1 and RE2 tied high to a +5 volt source for a free-running motor operation. The encoder master clock output is taken from the output OUT1 and supplied to the clock input CLK of the encoder 850. As conventionally known, the timing of the basic clock is established by the RC network including resistors 852 and 853 and capacitor 854. Its control voltage is by-passed by capacitor 857 and the basic clock operates at approximately 7 khz. The repeat clock outputs from the second half of the timer module 851 is taken from the OUT2 output which has a frequency of approximatelyt 7 hz. which, as conventionally known, is established by the RC network comprising resistors 855 and 856 and timing capacitor 899 with the control voltage by-passed by the capacitor 858. When the repeat key is down, switch 859 closes on the contact 860 and connects the repeat clock output OUR2 to the repeat input R of the encoder module 850.

The Shift and Control inputs to the encoder 850 are virtually identical circuits and the operation will be discussed for the control function it being understood that the operation for the shift function is substantially identical. At Power on, the capacitor 890 which is connected to the reset input R of the R/S flip-flop 884 maintains a low level for a short period of time. This causes the R/S flip-flop 884 to reset bringing its Q output high. This high signal enable NAND gate 886. After the capacitor 890 charges the reset input is brought high along with the other input of NAND gate 886. This brings the output of NAND gate 886 low turning the transistor 895 off. The low is also applied to the encoder as an off condition for the control input C. This condition is stable until the Control key represented by switch 891 or the Control Lock Key represented by switch arm 892 is closed when the key is depressed.

When the Control key is depressed, the second input of NAND gate 886 is immediately brought low and its output goes high giving the encoder 850 the control input via a high signal at the C input thereof. Similarly, the high at the output of the NAND gate 886 will supply base drive current through the current limiting resistor 894 to transistor 895 rendering it conducting. In the collector circuit of transistor 895 is a light emitting diode (LED) 897 which is used as a user indicator for the control function. The collector resistor 896 limits the LED current. When the Control key is released, the main gate input is returned high through the pull-up resistor 887 thus allowing the output of the main gate 886 to again go low to remove the control mode of operation.

Upon the depression of the Control Lock key, the set input of the R/S flip-flop 884 is grounded low from its normally pulled-up position provided by the pull-up resistor 887 and the +5 volt source of potential. With the set input going low, the Q output of flip-flop 884 goes low to turn on the control mode by bringing the output of main gate 886 high. This condition is also stable until reset by the depression of the control key. The Control key going low provides a reset function to return the control mode on and then off as the normally open key 891 is released. As stated above, the Shift and Shift Lock function of the circuit including flip-flop 886, main gate 865 and transistor 883 is substantially identical to the operation of the Control and Control Lock circuitry with the output of the shift circuit being applied to the shift input SHFT of the encoder 850.

The encoder 850 has the input keys arranged in a conventional XY matrix from the outputs X1 through X9 and the inputs Y1 through Y10. East X output is driven high for one clock cycle in the keyboard scan. If a key is down, one of the inputs Y1 through Y10 which are internally precharged low will be driven high through the switch by the X output. This combination of a certain X out and Y in produces a key code at the outputs B1 through B9 of the encoder. Only the 7 least significant bits are used of the 9 possible outputs with the B8 and B9 outputs being unused. When a valid key depression has been decoded, the data strobe output DS out will be brought high and delivered to the processors system through the inverting buffer 863 to provide the strobe signal to the PIA input CA1 of the Peripheral Interface Adapter 138 of FIG. 21. This requests the processor to read the keyboard output from B1 through B7. The data strobe control output DS COND is connected to the date strobe output to produce a data strobe output pulse equal to one clock cycle duration. The output enable output OE is tied low to enable the outputs B1 through B9 at all times and the key bounce mask input KBM has a capacitor 861 tied between it and ground for key switch bounce delay.

Figure 32:
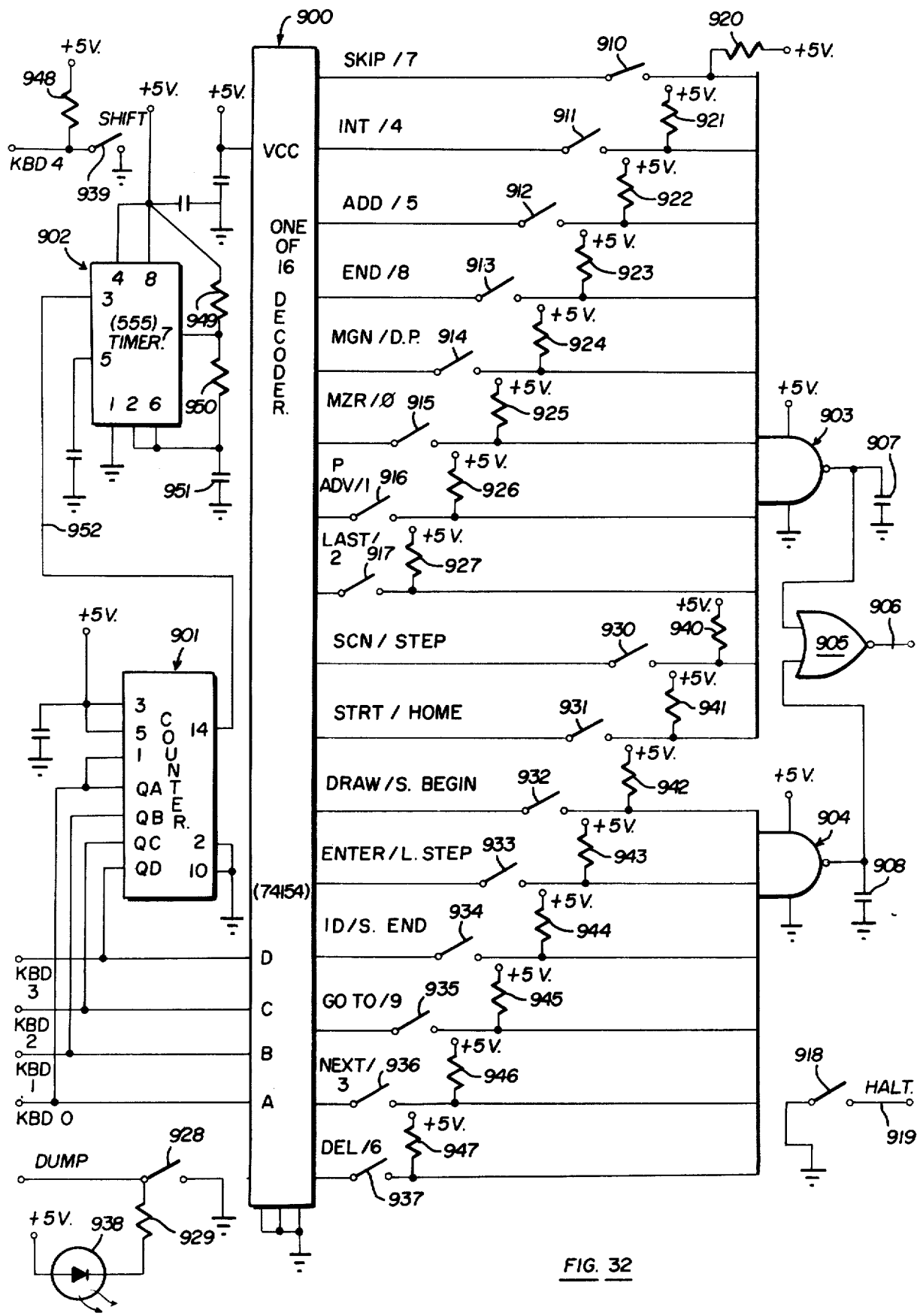
FIG. 32 is an electrical schematic diagram of the main chassis keyboard circuitry of block 42 of FIG. 1.

The keyboard circuitry of FIG. 32 includes a one-of-sixteen decoder 900 driven by a four bit binary counter 901 which is continuously cycled through its sixteen possible output states by a free-running timer 902. The outputs of the decoder 900 form two groups of eight keys each and each key is used as one input of an eight input NAND gate 903 or 904. The outputs of the NAND gages 903 and 904 supply the two inputs to a logical NOR gate 905 whose output is supplied via lead 906 to the circuit of FIG. 33 as hereinafter described.

More specifically, the sixteen outputs of the decoder 900 are divided into two groups of eight each and each key has a first value or control function when the shift key is depressed or closed and a second value or control function when the shift key is released. The two values (shift key released and depressed) are given on the input line with a "/" therebetween. The first eight keyboard entries to the decoder 900 are the key signals SKIP/7; INT/4; ADD/5; END/8; MGN/D.P.; MZR?): P ADV/1; and LAST/2 and each of these keyboard entry lines to the decoder 900 is connected to a normally open switch arm 910 through 917, respectively, each of which represents the corresponding keyboard key. The normally open contact of each of the associated switches 910 through 917 is connected to one of the eight inputs of NAND gate 903 and each is connected through a pull-up resistor 920 through 927 respectively, to a +5 volt source of potential.

Similarly, the second eight keyboard outputs of the decoder 900 are designated SCN/STEP; STRT/HOME; DRAW/S.BGN.: ENTER/L.STEP: ID/S.END; GO TO/9; NEXT/3; and DEL/6. Each of these eight outputs is connected to the normally open switching arms 930 through 937, respectively, and each of the switch arms represent one of the key members of the main chassis keyboard. Each of the key switches 930 through 937 is connected to one of the eight inputs of NAND gate 904 and each is connected to a +5 volt source of potential through pull-on resistors 940 through 947, respectively.

The outputs of the eight input NAND gates 903 and 904 are connected to ground through capacitors 907 and 908, respectively. The output of NAND gate 903 is connected to one input of a two input NOR gate 905 whose other input is connected to the output of NAND gate 904, and the output of NOR gate 906 supplies a control signal to the circuit of FIG. 33 as hereinafter described.

A HALT signal is generated by the closure of a normally-opened HALT switch key represented by the normally-opened switching member 918 which is grounded. The normally open contact supplies the signal HALT to the NMI input of the microprocessor 30 of FIG. 2 to stop the machine from executing its present operation.

The signal DUMP is controlled by the operation of a dump switch represented by the normally-opened switch element 928 and the contact element associated with switch 928 is grounded. The switch element 928 supplies the signal DUMP to the PA7 input of PIA135 of FIG. 20 as previously described. The switching member 928 is also connected to a +5 volt source of potential through a resistor 929 having one terminal connected to the switch element 928 and its opposite terminal connected to the cathode of a light emitting diode 938 whose anode is connected to the +5 volt source. Therefore, the signal DUMP is normally high so that a data dump will not occur. However, when the dump switch 928 is closed, the signal DUMP goes low and permits a data dump allowing the output ports to feed a computer for on-line storage of the collected information. The closure of switch 928 completes a current path betweeen the +5 volt source of potential and ground causing the LED 938 to be illuminated to indicate the dump condition.

The signal SHIFT is controlled by the operation of a shift key represented by the normally-opened switch element 939 whose switch contact is grounded. The switch element 939 is used to supply the SHIFT signal back to the PA4 input of PIA135 of FIG. 20 via the keyboard data line KB DATA4. The normally-opened switch 939 is also connected to a +5 volt source of potential through a pull-up resistor 948 such that in normal operation with the shift key open, a high SHIFT signal is outputted on the keyboard data path KBD4 but when the shift key is depressed and the switch 939 closed on its grounded contact, the output signal SHFT is pulled low to indicate a shift condition and select the second value or control function for the particular keyboard input being decoded.

A timing circuit 902 which, in the preferred embodiment of the present invention, may be a conventional 555 timer configured as a free-running oscillator, the frequency of whose operation is established by the RC conbination of resistor 949, resistor 950, and timing capacitor 951 which establish the frequency at approximately 800 Hz. The output of the timer 902 is supplied from the pin 3 output and connected via lead 952 to the pin 14 input of a four bit counter 901 which is continually cycled through its sixteen possible output states by the free-running clock 902. The binary counter 901 is, in the preferred embodiment of the present invention, a conventional 7493 device. The four outputs of the four bit counter 901 are taken from outputs QA, QB, QC, and QD and connected to the corresponding outputs A, B, C, and D, of the one-of-sixteen decoder 900 to be supplied back to the inputs PA0, PA1, PA2, and PA3 of the Peripheral Interface Adapter 135 of FIG. 20 via the keyboard data paths KBD0, KBD1, KBD2, and KBD3, respectively.

Figure 33:
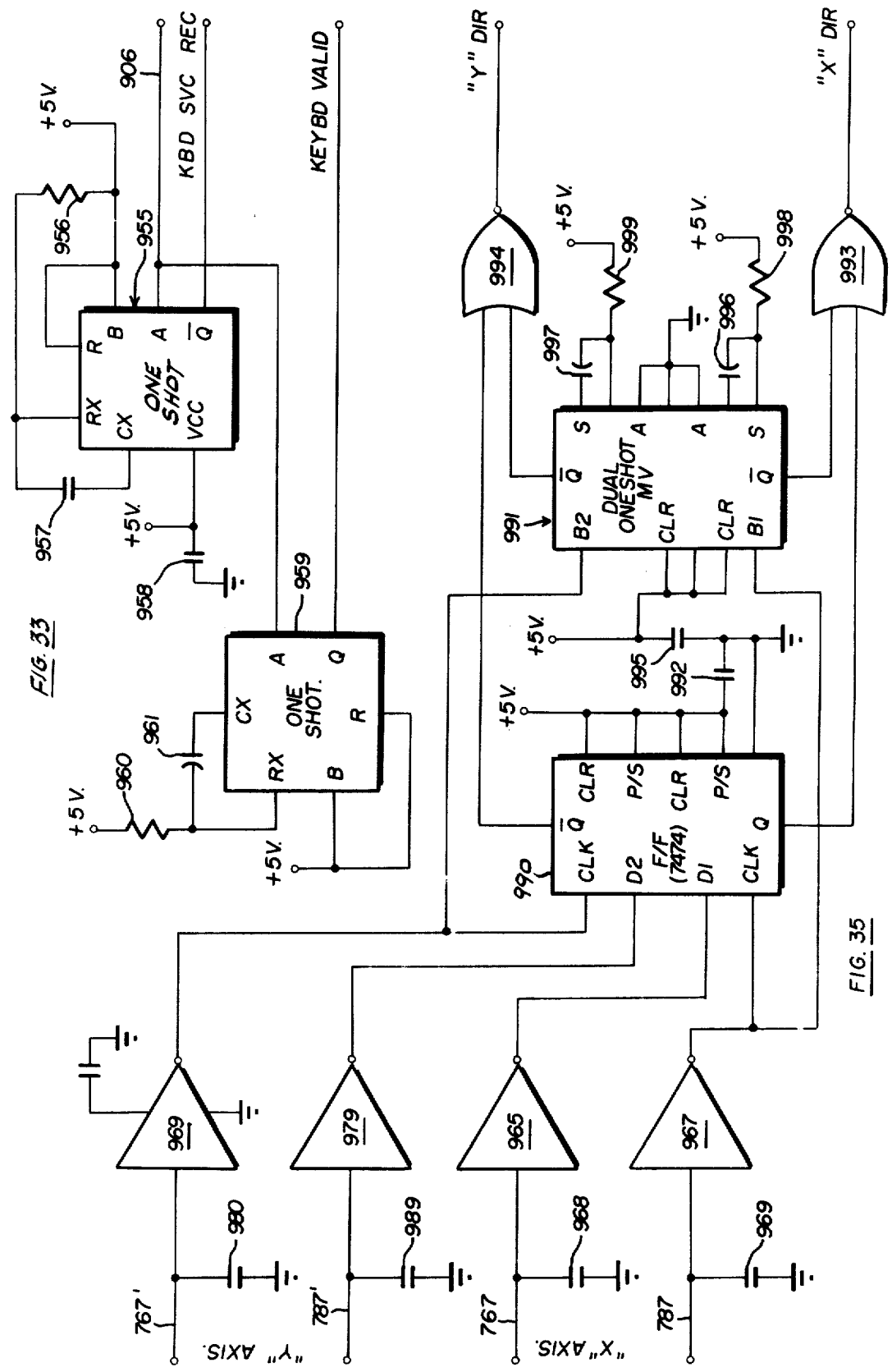
FIG. 33 is a detailed block diagram of additional keyboard circuitry associated with the main chassis keyboard of FIG. 32.

The output of NOR gate 905 is connected via lead 906 to the "A" input of a conventional one-shot multivibrator 955 of FIG. 33. A +5 volt source of potential is commonly connected to the "B" input and to the clear or reset input "R" of the one-shot 955. The +5 volt source of potential is also connected through a resistor 956 directly to the RX input and through a capacitor 957 to the CX input. The VCC input is connected directly to a +5 volt source of potential and to ground through a capacitor 958. The Q output of the one-shot 955 outputs the keyboard service request signal KBD SVC REQ to the CA1 input of the Peripheral Interface Adapter 136 of FIG. 20 are previously described.

The output signal from NAND gate 905 of FIG. 32 is also supplied via lead 906 to the "A" input of a second one-shot multivibrator 959. A +5 volt source of potential is connected through a resistor 960 to the RX input and the RX input is coupled to the CX input through a capacitor 961. A +5 volt source of potential is coupled directly to the "B" input and to the clear or reset input "R" of the one-shot 959 while the Q output supplies the keyboard valid signal KEYBD VALID to the PA5 input of the Peripheral Interface Adapter 135 of FIG. 20.

The main chassis keyboard circuitry of FIGS. 32 and 33 will now be briefly described. The primary component of the keyboard circuitry is the one-of-sixteen decoder 900 which is driven by the four bit binary counter 901. The four bit binary counter is continuously cycled through its sixteen possible output states by the free-running clock or timer 902 whose frequency is established by the RC network comprising resistors 949, 950 and capacitor 951. At each output count of the counter 901 the equivalent output of the decoder 900 is brought low. When a key is depressed on the keyboard, one of the sixteen switches is closed bringing one of the eight inputs of NAND gate 903 or NAND gate 904 low by this decoded count. Since all eight inputs of each of the NAND gates 903 and 904 are normally pulled high by their associated pull-up resistors, when a key is closed and the counter cycles to its equivalent output bringing the respective input of the closed key low, the input of its NAND gate 903 or 904 will go high.

Since the outputs of the two NAND gates 903 and 904 are NOR'ed together by NOR gate 905, the output of NOR gate 905 will go low and this low will be seen by both "A" inputs of the one-shots 955 and 959. The one-shot 955 operates in a retriggerable mode with its timing set greater than sixteen clock cycles of the timer 902 so as to insure providing only a single output transition per key closure. The Q output of one-shot 955 is used by the processor as the keyboard service request. The one-shot 959 is also triggered by the low signal at the output of NOR gate 905 and provides a time frame for the processor to read the output count from the counter 901. All propagation delays through the decoding network 900 will be hidden until this one-shot is triggered. The Q output goes high and should return low prior to the next count being instigated by the clock 902. This time frame is set by the RC network comprising resistor 960 and capacitor 961. Therefore, the processor 30 will not accept the output count until this key valid signal is present.

The three other key switches associated with the main chassis keyboard and shown on the circuit of FIG. 32 include the SHIFT switch which enables the decoded key switch information to be doubled; the HALT switch which is connected back to the non-maskable interrupt input of the microprocessor 30 of FIG. 2 and the function of the NMI input is basically used to regain control of the processor system; and the DUMP key is a normally high level to the processor system which is used to inhibit the optional data dump permitted by the preferred embodiment of the present invention.

Figure 34:
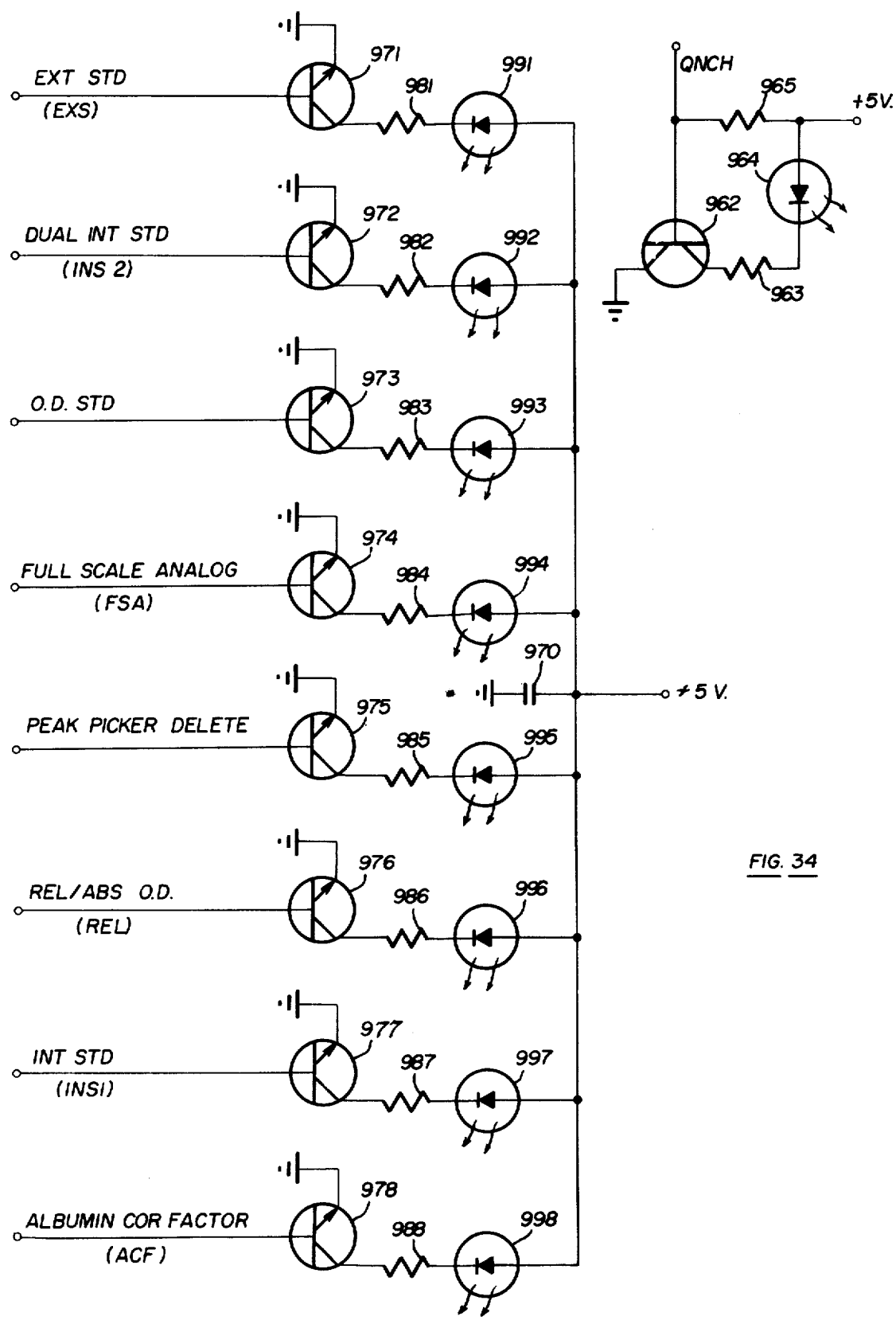
FIG. 34 is an electrical schematic diagram of the indicators associated with the keyboard circuit.

There are ten LED indicators located on the main chassis keyboard and they are associated with options which are not shown but which are defined at the intputs of the circuitry of FIG. 34 and by the dump circuit of FIG. 32. When the quench mode is activated by the depression of the quench key on the front panel or the remote keyboard, the signal QNCH which is normally low is pulled high and when this high signal is presented to the base of transistor 962 it switches to a conductive state. The emitter of transistor 962 is connected directly to ground and the collector is connected to the current-limiting resistor 963 to the cathode of LED 964. The base of transistor 964 is also connected directly to the anode of LED 964. Therefore, when the quench signal QNCH is in its normally low state, transistor 962 is biased in the non-conductive state and no indication is supplied by LED 964, but when the quench key is operated, the signal QNCH goes high causing transistor 962 to conduct to complete a current path between the +5 volt source of potential and ground through LED 964, current limiting resistor 963 and the conducting transistor 962. The current through the LED 964 causes it to emit light and provide a visual indication of the quench mode having been selected.

Eight other options (not shown) supply the following eight signals (1) the External Standard Selection signal EXS; (2) the Dual Internal Standard signal INS2; (3) the Optical Density standard O.D.STD; (4) the Full Scale Analog signal FSA; (5) the Peak Picker Delete signal PKPK; (6) the Relative or Absolute Optical Density Selection signal REL; (7) the Internal Standard signal INS1; and (8) the Albumin Correction Factor ACF and each of these signals is supplied to the base of a corresponding transistor 971 through 978, respectively. The emitter of each of the transistors 971 through 978 is connected directly to ground while each collector is connected through a current-limiting resistor 981 through 988, respectively, to the cathode of an LED 991 through 998, respectively, whose corresponding anodes are commonly coupled to a +5 volt source of potential and to ground through a capacitor 970.

The remaining eight LED indicators 991 through 998 operate a little differently from the quench indicator 964 and the dump indicator 938. The output signals are normally low keeping the transistors 971 through 978 in a non-conductive state but when a particular key depression causes a high to appear at the base of one of the transistors 971 through 978, it is conductive and completes a current path between the +5 volt source of potential and ground via the corresponding LED, its current-limiting resistor and the conducting transistor thereby causing the selected LED to give off a visual indication of the particular key function actuated.

FIG. 35 shows circuitry for modifying the signals from the carriage encoders of FIGS. 26 and 27 and provide outputs which signal the processor to count up or down for carriage movement tracking. The outputs from the "X" axis encoders of the circuits of FIGS. 26 and 27 are supplied via input leads 767 and 787 of inverting buffers with Schmitt trigger inputs 965 and 967, respectively. The input leads 767 and 787 to the buffers 965 and 967 are coupled to ground through capacitors 968 and 969 respectively.

Similarly, the "Y" axis inputs from a pair of encoder circuits similar to those of FIGS. 26 and 27 are supplied via leads 767', 787' to the inputs of a pair of inverting buffers with Schmitt trigger inputs designated by reference numerals 969 and 979 respectively. Each of the inputs to the buffers 969 and 979 are capacitively coupled to ground through a capacitor 980 and 989, respectively. In the preferred embodiment of the present invention, the inverting buffers with Schmitt trigger inputs 965, 967, 969 and 979 are conventional 7414 devices.

The output of the buffer 967 is connected directly to the clock input CLK of one side of dual D-type flip-flop 990 which, in the preferred embodiment of the present invention is a conventional 7474 device. The output of buffer 967 is also connected directly to the B input of one side of a dual oneshot multivibrator 991 which, in the preferred embodiment of the present invention, is a conventional 74123 device. Similarly, the output of buffer 969 is connected to the second clock input CLK of the flip-flop 990 and to the second B input of the one-shot 991. Alternatively, the output of the X axis buffer 965 is supplied to the D1 input of flip-flop 990 while the output of amplifier 979 is connected directly to the D2 input of the flip-flop 990.

The flip-flop 990 has its first and second clear outputs and its first and second per-set outputs connected directly to a +5 volt source of potential and all are capacitively coupled to ground through a capacitor 992. The Q output of flip-flop 990 is connected to one input of a two input NOR gate 993 while the $\bar{Q}$ output of the first side of the dual one-shot 991 is connected to the second input of NOR gate 993. The $\bar{Q}$ output of the flip-flop 990 is connected as the first input of a second NOR gate 994 whose second input is connected to the $\bar{Q}$ output of the second side of the dual one-shot 991. The dual one-shot 991 has both clear inputs connected directly to the +5 volt source of potential and capacitively coupled to ground through the capacitor 995. Similarly, both A inputs are connected directly to ground and the side number 1 and side number 2 S inputs are connected to capacitors 996 and 997 and resistors 998 and 999, respectively, to +5 volt sources of potential. The output of NOR gate 993 supplies the "X" direction signal to the CA2 input of the peripheral interface adapter 135 of FIG. 20 while the output of NOR gate 994 supplies the "Y" direction signal to the CB2 input of PIA 135 as previously described.

The square wave output from the carriage encoder circuitry of FIGS. 26 and 27 for the X axis and similar circuitry for the Y axis are supplied to the inputs of inverting buffers with Schmitt trigger inputs represented by reference numerals 965, 967, 969, 979 each of whose inputs are by-passed by a capacitor 968, 969, 980, and 989, respectively, to attenuate high frequency noise. The outputs of these buffers are applied to the D-type flip-flop 990 which receives one signal from each pair of amplifiers at its "D" input and the other at its clock input. The signals suppied to the clock input are also supplied to the "B" input of the one-shot 991 and the $\bar{Q}$ output of the one-shots is used to gate the outputs of NOR gates 993 and 994 to provide the X direction and Y direction chop signals to the PIA 135 previously described. This chop signal is used to signal the processor to increment or decrement the internal counters associated with the X and Y axis controllers.

The direction of increment versus decrement information is output from the NOR gates 993 and 994. In one direction, the phase difference in the two signals associated with one axis will produce a low at the D input of flip-flop 990 as the clock input signal rises and this will produce a high on the $\bar{Q}$ output which is NOR'ed by the NOR gates 993, 994. With one input of the NOR gates 995 or 994 high, a high pulse from the $\bar{Q}$ output of the one-shot 991 which is supplied to the other input of the NOR gates 993, 994 will cuase no pulse output from the NOR gates 993, 994. In the opposite direction, the D input of the flip-flop 990 will be high when the clock input goes high and this produces a low output which when NOR'ed with the output of the one-shot 991 will produce output pulses on the NOR gate versus the no pulse conditions described above. Therefore, the absence or presence of a pulse from the output of NOR gates 993 and 994 is used at a processor edge-sensitive input to determine the direction of carriage movement as previously described.

In order to further understand the operation of the present system and particularly the keyboard functions, the following additional information is provided. In the preferred embodiment of the present invention, the main chassis keyboard includes the sixteen data/control keys illustrated in FIG. 32; five function keys designated CONTROL, CONTROL LOCK, SHIFT, SHIFT LOCK, and REPEAT; and various other keys for controlling such functions as DUMP, HALT, RESET, CLEAR, BKSP and REL/LONG, as desired.

On the other hand, the remote keyboiard includes 56 data/command keys and five control keys. The five control keys operate the functions CONTROL, CONTROL LOCK, SHIFT, SHIFT LOCK, and REPEAT. The 56 data/command keys include the ten number keys zero through nine and the twenty-six alphabetic keys. Each of these keys provides a dual function since either the alpha-numeric information or the control function will be selected depending on whether or not the shift key is engaged. Twenty other keys control various keyboard-operated functions such as HOME, S BGN, S END, STEP, L STEP, DUMP, RESET, PACK/+, CLEAR, REL/LONG, LAST/, , NEXT/., ID//,-(minus), ENTER, HALT, SHIFT, and the like. The following is a listing of valid key entries which are not test functions and they are listed first in numerical order followed by alphabetical order. The numeric and alphabetic keys in a non-shift, non-control function represent their respective character and are used for patient identification, total protein information entry, or when it is desired, to enter other information into the computer. Of the functions listed below, several are indicated on the front panel of the machine including External Standard, Internal Standard, Dual Internal Standard, Albumin Correction Factor, Quench, Full Scale, Peak Pick, OD Standard, Relative OD, and Data Dump Inhibit, as previously described.

To facilitate listing, the key alpha or numeric character will be listed in normal order followed by the key's respective functional abreviation and the brief description of the action involved.

| Alpha Numeric Designation | Key Name | Function Performed |
|---|---|---|
| 1 | Skip | This key is used during data entry or the stand-by mode to enable the user to skip a specific pattern in the scan sequence. The code entered into memory for this pattern can be viewed by following the skip code entry by a "LAST" command. This code will remain associated with that sequence number until cleared by the "CLEAR" function key and re-entered. |
| 2 | End | During the stand-by mode this key sets the ending point for stepping which if not otherwise entered is through the forty-eighth scan. |
| 3 | SRCH | The search function will search through memory for a given sequence number or patient ID, retrieve it and present it on the display. The operation is as follows. First type in that sequence number or patient ID to be searched for, key |

-continued

| Alpha Numeric Designation | Key Name | Function Performed |
|---|---|---|
| | | "SRCH", and the system will request a key of "ID" or "SQS" representing ID and sequence respectively. If the information is valid the data will be presented on the display and can be cleared or changed for re-entry. If the information is not valid, the data presented will be the forty-eighth sequence number and its associated data. |
| 4 | SQS | This is the sequence input for the above routine (SRCH). |
| 5 | % | This "PERCENT" is valid only during the oscilloscope mode and will display the current scan's percentage values. The first key depression results in the first fractions percentage being displayed on the machine console. At this point the user has the option of stepping through the values by using the "NEXT" and "LAST" keys. To exit the routine a "CLEAR" key depression is required which will return the unit to displaying the scan on the oscilloscope. |
| 6 | NSP | The "NOT SERUM PROTEIN" key inhibits or enables the printing of the Albumin, Alpha 1, etc. headers on the graph output, as well as changing the printing of "TPGM%" to "U%". In the not serum protein mode the A/G ratio is deleted from the graphical output. This mode also selects a longer scan length, if selected, during the carriage set up procedures. A message is displayed indicating the current mode as well as a front panel indicator lamp following the entry. This is an alternate action key. |
| 7 | EXS | The "EXTERNAL STANDARD" key is also an alternate action key. It is as well displayed on the front panel by an indicator lamp. This mode allows the user to input total protein values for each sample. The corresponding scans graph will include that value scaled to the percentages. This is the normal or default mode which the machine comes up in. The total protein entry is made on the right hand side of the display. If ten patient ID characters have been entered, the machine is expecting the total protein entry. If there is no ID or only a few characters, either repetitive space bar or "/" will shift the input area to the total protein input area. |
| 8 | INS1 | The "INTERNAL STANDARD" mode derives total protein values from a standard scan's total integrals or amplitudes. In this mode the first scan made should be a "standard" with an associated total activity value entered into memory. See the explanation of "7,EXS" above for total protein entry. Succeeding scans will have their total protein value determined by the ratio between its total integral (amplitude) and the standard total integral (amplitude). There is no set relationship between where the standards must occur in the sequence of scans. However, whenever a standard is scanned it is presumed the following scans are to be scaled to that standard until another standard is encountered. In this mode of operation the graphical output is scaled to the standard unless the "FSA" (Full Scale Adjust) option is valid. The standard to which a scan is scaled to will be identified on the output graph. |
| 9 | INS2 | The "DUAL INTERNAL STANDARD" mode originates total protein values in the same way as the "INS1". However, a second standard is to immediately follow the first standard. When a non-standard |

-continued

| Alpha Numeric Designation | Key Name | Function Performed |
|---|---|---|
| | | scan is made, a comparison is made between the non-standard scan's total integral (amplitude) and the second standard. If the non-standard scan's totals are greater than the second standard's totals then the first standard is used as the ratio determining total. Therefore, the second standard should be the dilution of the first. The scan to which the non-standard was scaled to will be indicated on the printout. |
| A | SCAN | The scan function produces a scan providing the existance of the proper carriage location inputs. |
| B | INT | The integral function is an alternate action input which directs the machine to print or not print (default mode), the total and fraction integrals (amplitudes). |
| C | Kill | The kill function deletes an entire fraction area from calculations. The fraction is selected by centering the cursor between the fractions marks visible on the oscilloscope, and depressing the "KILL" key. The result is that the fraction will drop to baseline indicating the fraction is to be omitted. To reinstate the fractions value a "SENS" "KILL" key sequence or a "SENS" function should be executed. Refer to the "SENS" function listing for a complete description of the effects of this key. Up to three "KILL" areas may be selected for any scan.<br><br>When the "DRAW" command is given and a kill area exists a request will be made for a plus or a minus input. This will produce a graph with or without the kill area being included in only the graphical portion of the output. A hardware option exists to produce either a positive fraction mark for the area or a trace which is chopped as an indication of the "KILL" area not being reflected in the computations. |
| D | MZR | The manual zero routine has two resultant actions. The first is during the stand-by mode. During this mode the "MZR" key turns the display into a digital voltmeter which is monitoring the input signal. Thus it can be used to set up the front panel analog gain and zero adjustments by moving the carriage to the appropriate position below the light beam either to the background portion of the pattern for a zero set up or to the densest portion of the pattern for a gain adjust.<br><br>The second function of the "MZR" key is to allow the user to select a zero point along a pattern displayed on the oscilloscope. This is accomplished after scanning by depressing the "MZR" key once to display the raw or unadjusted data collected during scanning. The cursor is then set to the point where the desired zero level is and the "MZR" key depressed a second time. This has no affect on the machine zero only the current scan's baseline. The fraction locations and beginning and ending points of scanned data are not affected. |
| E | CBL | The change baseline function is another multiple key input. The first depression will display a prompt to the user. This prompt requests a "0" or a number followed by a plus or a minus. The "0" resets the baseline to the machine picked baseline. The number plus or minus shifts the baseline up or down by an amount equal to the entered number multiplied by one-one hundredth of the originally displayed graphical data. If a baseline shift greater than nine-one hundredths of the original is necessary a repetitive operation is required to obtain the percent shift desired. |
| F | MGN | The manual gain routine selects a unity gain analog output to the recorder such that the user can control the peak value of the output to the recorder. In the case of the graph the automatic full scale scaling is precluded. This routine is selectable from either the stand-by mode or the oscilloscope mode. It is indicated on the graphical output by the printing of a "G" on line three following the total protein value. |
| G | STPT | While in the oscilloscope mode the start point function selects a point along the curve at a fraction mark located to the right of the cursor for the starting point of data. |
| H | AMP | The amplitude key selects on an alternating basis the integral mode (default) and the amplitude percent mode. This key is valid during either the stand-by mode or the oscilloscope mode. This allows one to obtain both sets of data after a scan is made. This function is indicated on the output graph by an "I%" or "A%" being printed following the sequence number on line two. |
| I | LAMP | The lamp key sets the visible light source to an alternate mode. For example, if high power setting is desired the lamp key depression will set the lamp to the high power setting with an "INVERT" prompt. To reset the lamp to the original machine configuration another "LAMP" key depression and the prompt "NORMAL" will effect the change. |
| J | | Although this key is not labeled as such, it does have a control function. It produces a code, in the control mode, which is a backspace. See "BKSP". |
| K | PKPK | The peak pick routine is another alternate action key accessible from either the stand-by mode or the oscilloscope mode. Its function is to delete all but the beginning and ending fraction marks from the current scan so the user can select all fraction marks within the scan. The machine will respond with a prompt "NO FRACTIONS" for this mode. The next depression of the "PKPK" key will reinstate the machine picked fraction marks and prompt of "FRACTIONS". This mode is indicated on the machine front panel by an indicator lamp.<br><br>Since a fraction is defined by the locations of two marks along the waveform and the beginning and ending points are selectable, a mark should appear at the beginning and ending points of the waveform. Therefore, if a long and/or very noisy scan is made some fraction marks may not be easily discernable from the scan waveform on the oscilloscope. A depression of this function key deletes all but the required fraction marks for 100 percent representation (i.e., beginning and ending). The rest of the fraction marks are then easily inserted using the "ADD" function in conjunction with the cursor. |
| L | FSA | The full scale adjust routine is another alternate action key accessible from either the stand-by or oscilloscope mode. Its function is to inhibit the automatic graph amplitude scaling that takes place in some of the modes of operation, such as the internal standard mode. |
| M | | Although this key is not labeled with a |

| Alpha Numeric Designation | Key Name | Function Performed |
|---|---|---|
| | | control function, it does produce a code in that mode. The resulting code is a duplication of the "ENTER" key. |
| N | GOTO | The GOTO function directs the densitometer system of the present invention to assume the pre-scan position at the desired scan sequence number. In operation one would depress the "GOTO" key and the two numerical keys associated with the desired scan such as "GOTO"-"2"-"4", and the machine will drive the carriage to the appropriate scan position and wait for further commands. |
| O | P.ADV | This is an alternate action function key which is accessible during the stand-by and oscilloscope modes. It provides the service of advancing the chart paper. |
| P | TEST | This is the test key which accesses and precedes the test functions. |
| Q | STRT | The start key starts the auto step sequence of events. From the stand-by mode of operation, the start key brings about a carriage movement to the displayed sequence numbers respective scan. The machine will then wait for verification of the correct position and another depression of the "STRT" key at which time the auto step sequence of events commences. From the oscilloscope mode of operation the key will bring about another reaction. It is assumed auto step operation has been in effect and a manual intervention has taken place resulting in the desired graph from the present scan. Therefore, the machine will step to the next scan as though the manual intervention had not taken place. |
| R | ACF | The albumin correction factor key performs in much the same way as the "CBL" function. That is the number entered multiplied by one-one hundredth of the scans amplitude. The number entered should also be followed by a plus or a minus to indicate the direction of the charge. Once entered that value remains for future scans until changed or a power on or reset occurs. |
| S | DRAW | The draw command instructs the machine to produce an output graph. If a "KILL" area exists a prompt will be displayed requesting an input as to whether or not the graph is to be drawn with or without the "KILL" area, as discussed under the "KILL" routine. This key is valid only during the oscilloscope mode. |
| T | SLOPE | The slope function substracts out a triangular area beneath the current scan. The beginning and ending point of this triangular area are determined by the beginning and ending fraction marks. The amplitude of this triangular area is determined by the height of the fraction mark, either beginning or ending, located the furthest distance from the baseline, see "TEST" "SLOPE" to obtain a graphical output of this triangular area. The graph of a pattern which has been subjected to the "SLOPE" routine will contain an "S" which is printed on line two following the I or A% mode indication. |
| U | QNCH | The quench key functions as an alternate action key, accessible from either the stand-by or oscilloscope mode. This function once set remains in effect until either a machine power on or another "QNCH" key depression. The result of the mode being in force is an inversion of the sampled data. |
| V | SENS | The sensitivity key is valid from the oscilloscope only and affects future scans until reset by a power on or another "SENS" key depression. |
| W | INVT | The invert mode is an alternate action key valid during the stand-by mode of operation only. The key will change the analog portion of the machine to be the alternate mode determined by the switches located in the optics which are operated by the attenuator/collimator disk. |
| X | DEL | The delete function is used to delete a fraction mark at the cursor location. As with the "ADD" function, if the cursor is not located on the waveform displayed on the oscilloscope no action will take place. |
| Y | ODSTD | The OD standard key is used in setting up the machine to compute, and output on the graphs produced, the respective optical density of the peaks located between fraction marks. This in conjunction with the amplitude percent mode and amplitudes will display vertical deflection information about scans produced. |
| Z | ADD | The add function is used to add a fraction mark at the cursor location. As with the "DEL" function, if the cursor is not located on the waveform displayed on the oscilloscope no action will take place. |

The following keys have neither a numerical value nor an alphabetic character associated with them and are used exclusively as command and control keys and include the following

| Key Name | Function Performed |
|---|---|
| "HALT" | The halt key will stop the machine from its present operation and return to the stand-by mode awaiting instructions or data. This will not alter machine locations or destroy patient data. |
| "HOME" | The home function has two basic functions. The first deals with the automatic set up of the carriage scan locations. The machine will compute the necessary addresses for the carriage and will respond with the number of steps programmed in. If carriage information is already in existence within the machine it presumes an alternate mode of operation. It should be noted that the carriage locational information is required for automatic step over operation. However, for a manual type step over operation the only required inputs are the scan begin and end information. |
| "S.BGN" | The scan begin key should be depressed when the carriage is located with the pattern to be scanned |

-continued

| Key Name | Function Performed |
|---|---|
| | just to the right of the light beam plus any over scan area. This will enter the first column scan begin limit, the next depression of this key will result in entering the second column scan beginning point and the next will be the first again. |
| "S.END" | The scan end key operates in the same fashion as the "S.BGN" key above with the exception that it deals with the scan ending point and has no effect on the scan begin position. |
| "STEP" | Each depression of this key results in a step being programmed into the machine at the current location of the carriage. There is a limit of twenty-four steps per column or side of the carriage. |
| "L.STEP" | The last step function key enables the user of the densitometer system of the present invention to rapidly program steps into the machine. |
| "DUMP" | This key is made available to the users of the machine who are using one of the output ports to feed a computer for online storage of the collected information. In its on condition a data dump will not occur. Thus a scan can be produced several times on the scanner without the data being sent out over the lines. |
| "RESET" | This is the panic button. It will simulate a power on reset. If after completing a seris of scans it is desired to re-establish the original machine configuration a depression of this key will result in such action. |
| "CTRL" | This is the control key which allows the user to access the functions which are listed above most of the alphabetic keys. |
| "CTRL LOCK" | This key serves to lock the keyboard in the control mode. Thus the user may operate the keyboard with one hand or finger. |
| "SHIFT" | The shift function allows the user to access the routines which are listed above most the numeric keys in the case of the remote keyboard and above all keys on the machine's main chassis keyboard. |
| "SHIFT LOCK" | This key locks the remote keyboard into the "SHIFT" mode. It does not affect the machine's main chassis keyboard. |
| "REPT" | This is the repeat key. It is useful in stepping through the entered patient information using "NEXT" and/or "LAST". |
| "PACK+" | The pack function allows the user to delete the printed fraction information printed on the graph. It is an alternate action key and the results of the key depression are displayed as a message on the machine console. |
| "BKSP" | This is the backspace key. It functions as a normal backspace. |
| "CLEAR" | This is the clear function. It is used to clear entered data and/or as an input after certain commands. |
| "REL/LONG" | The relative OD or the absolute OD is selected by the use of the "SHIFT" "LONG" key. This is an alternate action key. This selection is valid during either the stand-by mode or the oscilloscope mode. The values printed on the output graph will indicate on line four, first character, the selected types of values being printed. The "LONG" key serves to set an alternate data point selection mode which allows the user to sample longer patterns. The primary reason for this function is to adjust the number of data points of a scan to quantity which will fit into memory available without overflow. |
| "LAST/" | The comma is a valid input for the patient ID region of the display only. The "LAST" key of "SHIFT" "," is used to bring the previous sequence number and patient information from memory to the display. |
| "NEXT/" | The period or decimal point is valid key entry for either the patient ID area or the total protein entry area of the display. The "NEXT" function is similar to the "LAST" function above. However, it retrieves the next sequence number and patient information, if entered, from memory to the display. |
| "ID/ /" | The "ID" functions as a display refresh request input. Thus, if a prompt is displayed and the user wishes to reinstate the display with the current sequence number and its associated information a depression of this key is required in a "SHIFT" mode. This function is valid during either the stand-by or oscilloscope mode. In the "NON-SHIFT" mode this key serves as a tabulation |

| Key Name | Function Performed |
|---|---|
| | command to shift the input to the total value region of the display. This function is valid only during the stand-by mode where patient data entry is possible. |
| "—(MINUS)" | The minus sign is used as an input in response to machine requested key entries. |
| "ENTER" | The enter key serves to enter the displayed data into the machines memory. |

Figure 36:
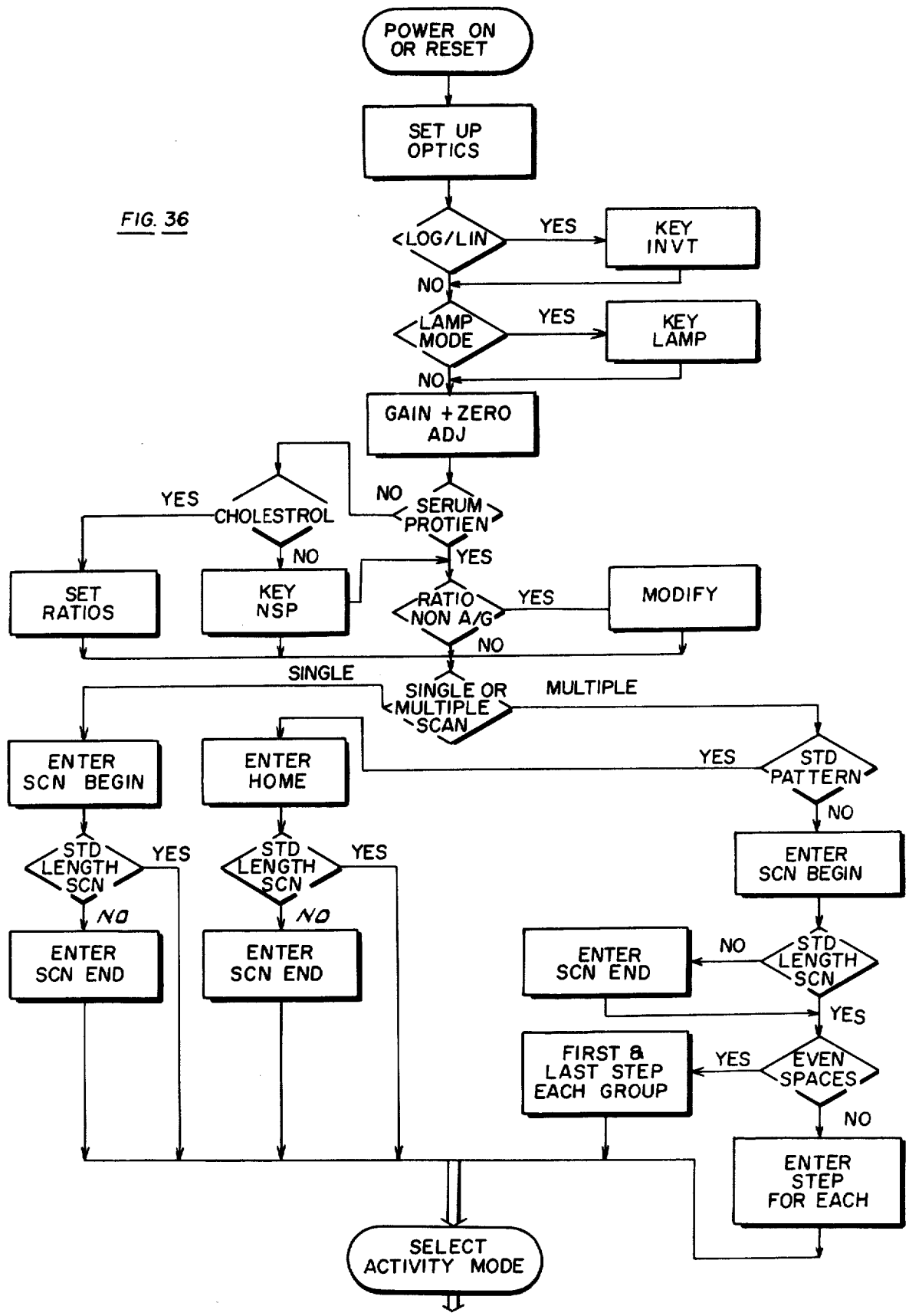
FIGS. 36 and 37 represent a single overall flow chart illustrating the operation of the densitometer system of the present invention.
Figure 37:
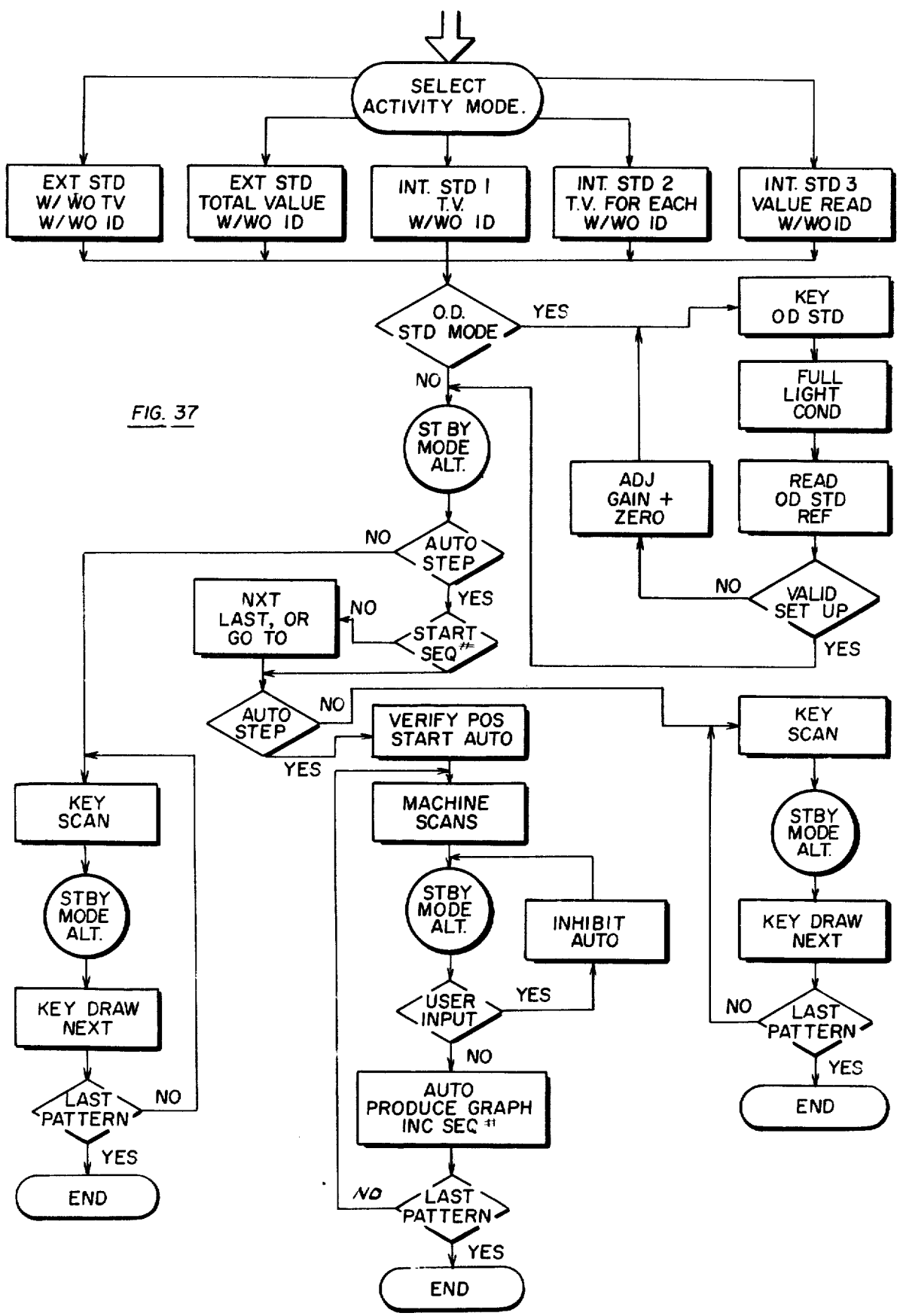
Figure 38:
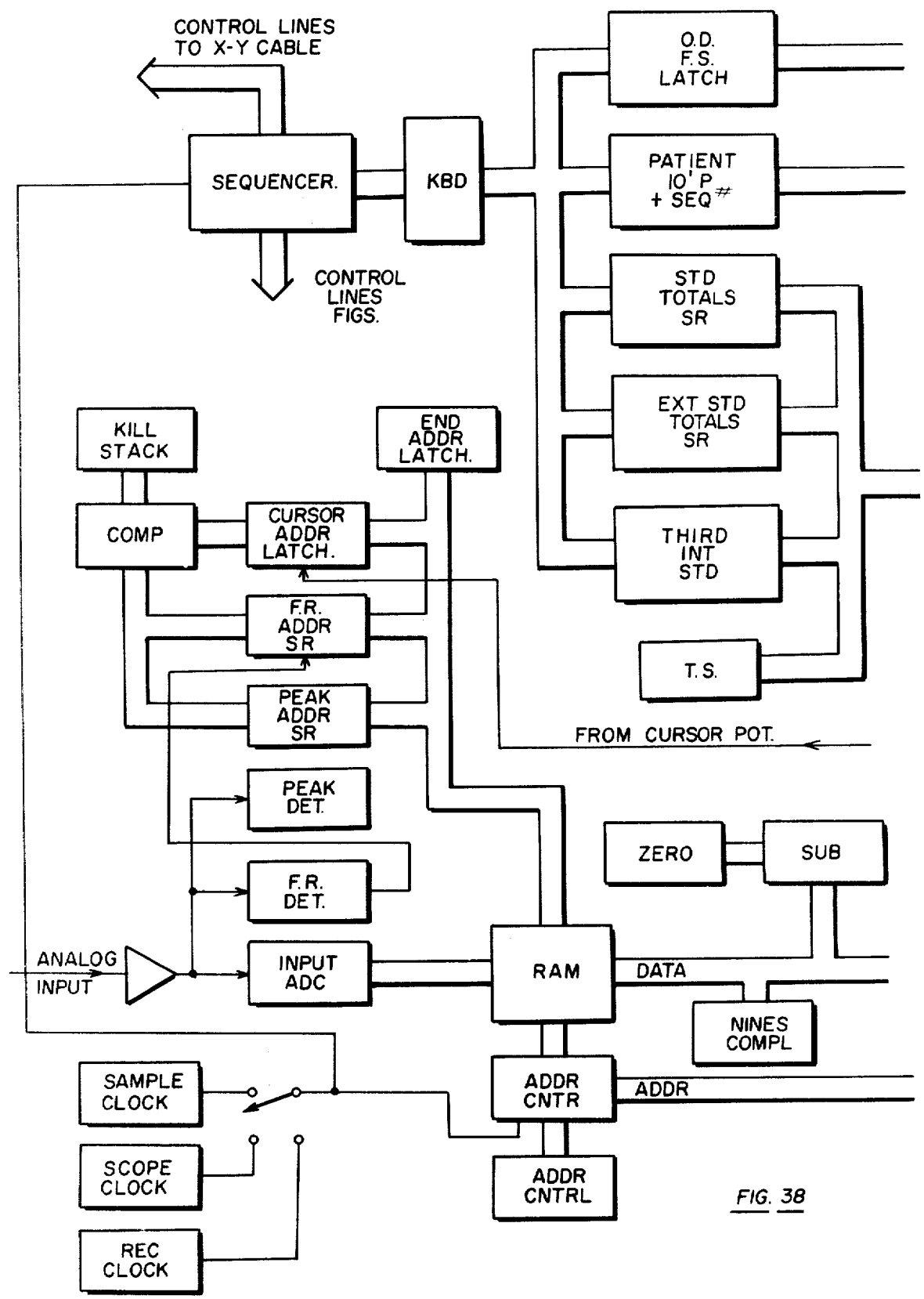
FIGS. 38 through 41 represent a single block flow diagram representing a hardware-implemented version of the program used in the preferred embodiment of the present invention and is used for describing the actual operation of the system of the present invention.
Figure 39:
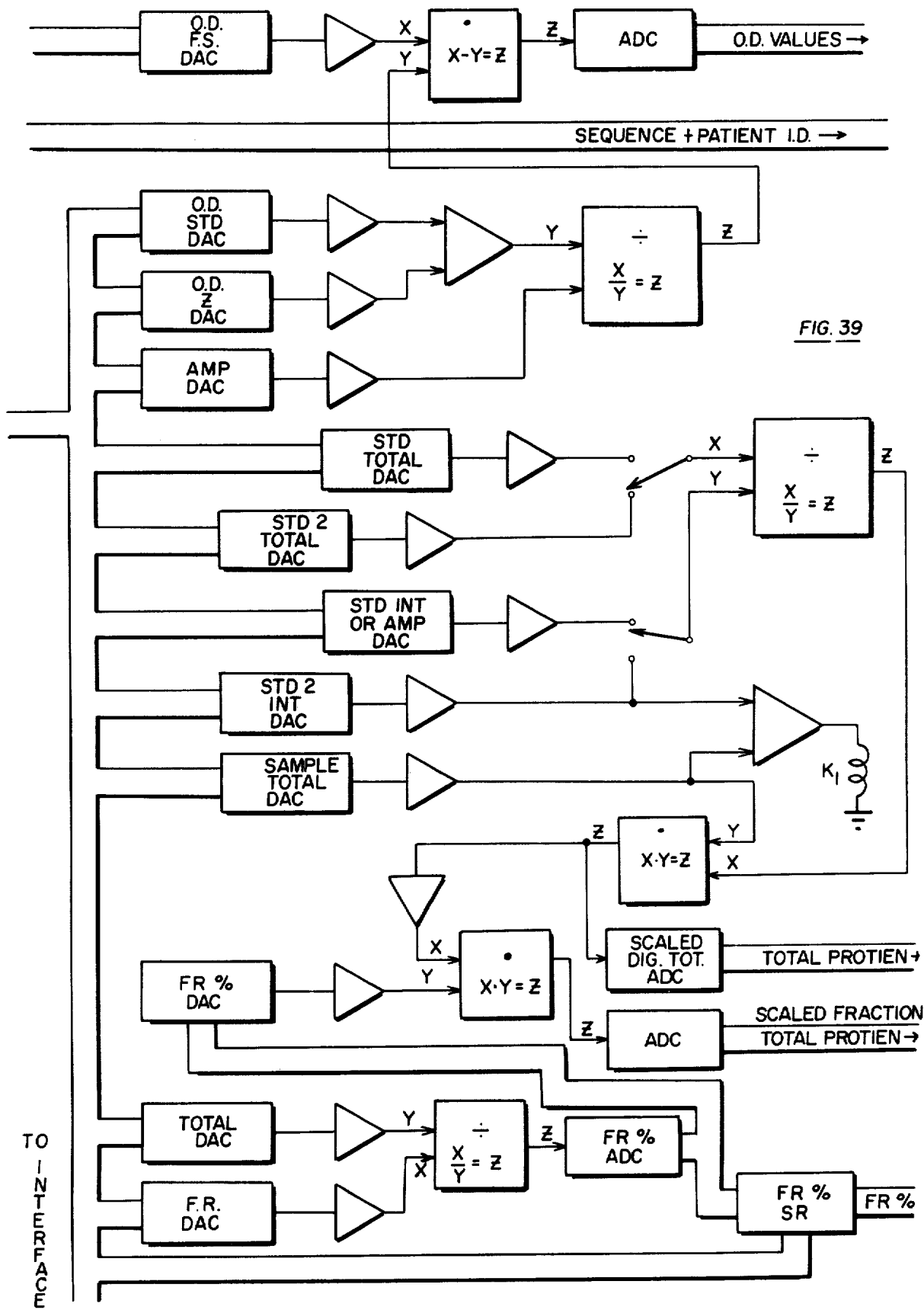

FIGS. 36 and 37 illustrate the overall flow diagram of the operation of the microprocessor-controlled densitometer of the persent invention and show the various alternate modes of operation.

Figure 42:
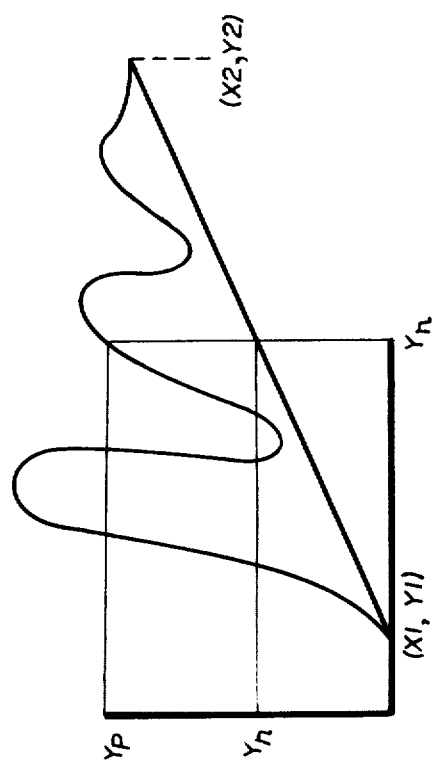
FIG. 42 is a graph relating the pattern and trace and the generated slope with the calculation operation defined by the circuit of FIG. 41.

In the preferred embodiment of the present invention, a program is stored in the read only memories of FIG. 3 and while the programming is conventional and well within the level of ordinary skill for a programmer, a copy of the program listing is attached hereto as an APPENDIX and incorporated by reference herein. Furthermore, for ease of explanation in describing the operation of the densitometer system of the present invention under the program control of the microprocessor 30, the circuitry of FIGS. 38, 39, 40 and 41 which represent an alternate hardware embodiment of the program will be used. The graph of FIG. 42 illustrates the computations accomplished by the circuitry of FIG. 41 and requires no great explanation.

In FIGS. 38 through 41, the individual blocks are not referenced by number since each block is labeled and in the preferred embodiment of the present invention each DAC is a conventional digital-to-analog converter such as a twelve bit binary coded decimal Ad563 device; each ADC is a conventional analog-to-digital converter such as a conventional ADC171 device; each analog multiplier or divider which is represented by the multiplication dot or the division symbol are conventional analog multipliers such as AD532 devices. Similarly, each of the latches is a conventional 74100 eight bit latch; each of the shift registers SR are conventional devices such as a Motorola MC14517B; each adder is a conventional device such as a Motorola MC14560; each subtractor is a conventional device such as a Motorla MC14561 and each of the clocks can be a conventional device such as national semiconductor NE555 timer or the like. The random access memory or RAM can be a conventional EMM4202 4K×1 RAM; the address counter may be a conventional presetable binary coded decimal up/down counter as a 7492 device; and the nine's complement box may be a commercially available off-the-shelf device such as Motorola MC14561. To summarize, all of the devices shown in the blocks of FIGS. 38 through 41 are conventional and since they are used as an alternate embodiment of the program and for ease of explaining the overall operation of the system, additional information will not be necessary to those skilled in these arts.

The overall operation of the densitometer system of the present invention will now be described. The user will enter into the keyboard the mode the machine is to be in. This mode information will select the proper program steps for the microprocessor to execute or, with reference to FIGS. 38-41, the proper sequence for the sequencer to follow. This will differentiate between External Standard and Internal Standards 1, 2 and 3. The user follows by entering the total values and patient names which are entered into the proper shift register under program control or by the sequencer. The size of the shift registers, adders, DAC's and ADC's are not called out in the diagram but can be any word length required for proper data resolution.

At the start of a scan the sequencer instructs the X-Y table or carriage to scan. As the sample is passed between the light source and sensor the resulting electrical signal is applied to the A1 amplifier. The INPUT ADC is an analog to digital converter which samples or converts the incoming analog signal into digital words. These digital words are stored in the RAM (Random Access Memory). The addresses of the RAM are determined by the address counter (ADDR CNTR) which was reset at the beginning of the scan sequence by the program or sequencer. The address counter increments the address by the sample clock input. The X-Y carriage table continues to traverse the sample until the end of scan position is reached. When this occurs the end address is latched into the END ADDR LATCH. The sequencer then switches clocks to the scope clock. (The auto gain function is not shown). The lowest reading is stored in the block labeled "Zero". This value is subtracted out from all of the data for auto zero correction.

The sequencer or program (henceforth it will be assumed that any reference to the sequncer refers equally to the program as executed by the processor 30) ensures the scope-recorder switch is to the scope position. At this time the data is sent from the RAM to the VERT DAC via the data bus where a digital to analog conversion is performed for the oscilloscope vertical deflection. The sequencer enables the HORIZ DAC which transforms the incrementing address from ADDR CNTR to an analog ramp for the oscilloscope horizontal deflection. This sequence continues until all the data is displayed, determined by END ADDR LATCH, at which time the sequencer resets the ADDR CNTR for another oscilloscope trace. This process is repeated rapidly for the visual presentation of the density profile on the oscilloscope.

During the scan time where the INPUT ADC is converting the input signal the PEAK DETECT and FR DETECT are producing output signals when a high point or low point are reached. These signals are applied to PF ADDR and FR ADDR shift registers (SR), respectively. These shift registers hold the addresses of the peak signals and fraction or low point signals. These addresses are stored for future reference and their use is covered later.

The operator is now viewing the pattern on the oscilloscope. He has the option of editing the scan using the cursor as a pointer on the oscilloscope display, in conjunction with labeled keys on the keyboard (KYBD) or of simply reviewing the scope trace without editing changes and then recording same. The editing options include Kill, Add, Delete, Start Point, End Point, Change Base Line, Albumin Correction Factor, and Quench. These functions will now be discussed, in the above order.

Prior to covering the above functions, the cursor operation will be discussed. As the scan data is being presented on the oscilloscope each sampled point along the signal is associated with a unique address. The incrementing addresses produce a ramp voltage for the horizontal deflection which is compared to an adjustable voltage (CURSOR CONTROL POTENTIOMETER). When the ramp, and thus the corresponding address, is at the cursor location the comparators output will make a transition whch will latch that address into the CURSOR ADDR LATCH. The sequencer then adds a vertical amount to the VERT DAC at ADDER and takes a short time out. This produces the visual effect on the oscilloscope display of a bright dot slightly elevated from the pattern trace. It is this visual feedback to the operator that indicates the position of the cursor. This cursor will follow the trace on the oscilloscope as the user moves the control potentiometer. Thus, a unique address is associated with the cursor within the electronics. The user, as stated, can use this cursor as a pointer. When a key is depressed the sequencer will know where the cursor is by the address in the latch. Now, on to the functions.

The Kill function deletes an area of the curve from computations. This area is bounded by fraction marks which are represented within the machine as addresses. To perform this function the operator will set the cursor, visible on the oscilloscope, within two fraction marks and depress the "KILL" key. The sequencer then outputs from the recycling shift register FR ADDRS the fraction addresses. These are compared at COMPARATOR, a digital comparator, with the cursor latched address at CURSOR ADDR LATCH. When the sequencer locates the cursor between two fraction marks the fraction addresses are latched into the KILL STACK shift register (i.e., $fr_n < x < fr_{n+1}$). As the oscilloscope display commences the FR ADDRS shift register is reset to the first fraction location.

The CURSOR ADDR LATCH then is opened to a non-latch or feedthrough operation. This allows the comparator to monitor the output address. As the comparator senses a match (i.e., fraction location is being put out) the sequencer switches the kill stack output to the comparator to check if the fraction has been killed. If not, the FR ADDR is stepped to the next mark and the VERT DAC added to by ADDER for visual indication of the fraction mark. The display process then continues. If the fraction mark was a killed area the sequencer will clear the VERT DAC and continue through the addresses after stepping FR ADDR to the next fraction address. This will drop the vertical trace on the oscilloscope to baseline between the killed fraction-fraction marks. When the end of the killed fraction has been reached the sequencer enables the VERT DAC to again accept input data, after checking the next fraction for a killed condition and stepping KILL STACK to the next kill address.

It should be noted that the manner in which the addresses are placed onto the KILL STACK shift register is important. They should be in ascending order to comply with FR ADDR order. This can be performed by the sequencer. During the computational sequence, prior to the outputs being printed, the sequencer will compare the KILL STACK against the FR ADDR and not sum any killed area into the integrals or amplitudes. Thus, the killed area does not enter into the computations.

The add function is used to manually add a fraction mark at some point along the curve or density profile. The operator will bring the function about by setting the cursor at the desired point and depress the ADD key on the keyboard (KYBD). The sequencer, as before, cycles the existing fraction addresses through the comparator and locates the COMPARATOR ADDR LATCH address such that $fr_n < x < fr_{n+1}$. The sequencer then inserts this fraction location into the fraction stack at FR ADDR shift register.

It should be noted that the kill stack is not checked out for adding or deleting fraction marks. It is beyond comprehension why an operator would desire to do such. Therefore, the kill stack remains unaffected.

The Delete fraction mark is similar except the sequencer removes that fraction address from the FR ADDR shift register. The cursor is place in front or to the left of the fraction mark to be deleted. This allows the sequencer to delete the next higher fraction mark than the cursor. To reiterate the sequence of events: The user places cursor to left of fraction mark, presses delete, sequencer cycles address to read cursor at latch, cycles RD ADDR to find fraction address to delete. This address is removed from the shift register (FR ADDR) and the remaining ones shifted in to retain consecutive nature of the stack.

The STPT or start point function selects a new beginning point for the scanned sample being presented on the oscilloscope. This is done by the operator setting the cursor in front mark which will be the new starting point on the display. The user would then depress the STPT key. The sequencer would then locate the cursor by enabling the latch (CURSOR ADDR LATCH) and cycling ADDR CNTR through the addresses. The cursor comparator would enable the latch as the desired address is passed. The sequencer would then cycle through the FR ADDR shift register deleting fraction locations until a fraction address was found greater than the cursor address. This fraction mark would then be the new starting point of data. The sequencer would then store this address in ADDR CONTROL as the reset location. This would allow the ADDR CNTR to reset to this new value in lieu of $\phi\phi\phi\phi$. Therefore, the displayed graph on the oscilloscope would start at that point. The computations would also start at that point when required.

The ENDPT or end point function selects a new ending point of data. It is brought about by the user setting the cursor to the right of the fraction mark which is to be the new ending point and depressing the ENDPT key. The sequencer follows the same process to identify the cursor address. It then latches that address at the END ADDR LATCH and deletes the remaining fraction addresses at FR ADDR.

Once the user is satisfied with the presentation a DRAW key is depressed, or automatically in the auto mode, a graph is produced. Prior to the actual reproduction of the graph the numerical data is required. The computations are brought about by the sequencer clocking the data into the proper registers. The sequence discussed now will be an example of the external standard mode. In this mode the total proteins have been input by the user and are stacked into EXT STD TOTALS shift register.

The first computation required is the fraction percentage. These are based on the total integral to fraction integral ratio for the integral percent mode. An alternate mode is the amplitude percent where the fraction percentages are based on total amplitude to fraction amplitude ratio. To obtain these summations and values the sequencer resets the ADDR CNTR to the beginning address held in ADDR CONTROL. The sequencer then enables the adder labeled INT TOT (Integral Totals) such that all the data points will be summed when they are put out. The sequencer compares the first fraction address at FR ADDR with the starting point address. If they are the same the data summation will begin. If not the sequencer will increment the address until the first fraction address is obtained prior to summing.

To sum the data points the sequencer enables the adder at INT FR, enables the address to the RAM and clocks the two adders INT TOT and INT FR. The next data point is accessed by incrementing the address and checking it against the next address in FR ADDR to detect the end of the fraction. If it is not the end, the data is output and clocked into the adders INT TOT and INT FR and the process continues. When the end of a fraction is reached the sum at INT FR is clocked out of the adder into the shift register for future reference. Also, the next end fraction mark is accessed at FR ADDR, the INT FR is cleared and the process is repeated until all data points have been summed at INT TOT and each fraction sum has been clocked into its shift register. This provides $$\sum_{1}^{n} x$$

where n is the number of data points between first and last fraction mark and $$\sum_{a}^{b} x$$

for each fraction where a to b are the fraction marks.

Had the user opted for the amplitude percent mode the sequencer would cycle through the addresses observing the fraction mark delineation. Between fraction mark addresses the data would be output from the RAM and subtracted from the next data point. When a lower data point is detected (i.e., first borrow condition) it is held in ADDER until the end of fraction is reached and the address in CURSOR ADDR LATCH while the subtraction continues. If another peak is found before the end of fraction is reached the last peak (ADDER) is subtracted from the new peak. The highest data is placed in ADDER and its address saved at CURSOR ADDR LATCH. When the end of fraction is reached the address is clocked into PK ADDR and the data point is summed into AMP TOTAL adder and clocked into AMP FR shift register.

To begin the computation of the fraction percentages the sequencer directs the proper total value from either the INT TOTAL or AMP TOTAL to the TOTAL DAC. This digital to analog converter delivers its output to the Y input of a divider module. The sequencer then directs each fraction, in turn, from the AMP FR or the INT FR shift register to the FR DAC. The output of this DAC is delivered to the divider module dividend input (x). The output of this divider module is an analog voltage representative of the fractions value (amplitude or integral) divided by the total value (amplitude or integral) or its percent value. This is changed back into a digital word by the FR% ADC and stored at FR% SR for temporary storage and future reference. The percentage values will be clocked out of this shift register when required at FR%. As the total and fraction values are clocked into the computational circuits DAC's the integrals or amplitudes are available for output at INT or AMP.

The produce a total Protein output in the External standard mode the sequencer overrides the Dual Internal standard comparator at the output of STD 2 INT DAC. This is done by clearing the STD 2 INT DAC and writing the samples into the STD TOTAL DAC and STD INT OR AMP DAC whose outputs are selected by K1 by the override condition. This produces a divided equal divisor condition at the divider module giving a Z output equaling one. Therefore, the output at the multiplier is the analog equivalent to this user assigned total protein value since the multiplier (x) is one or unity. This analog equivalent is transformed into a digital word for output by the SCALED DIG TOT ADC at TOTAL PROTEIN.

The protein of each fraction (i.e., % of total) is then available at SCALED FRACTION TOTAL PROTEIN as each percent value is computed above. This is performed by the FR% DAC transforming the digital percentage to an equivalent analog signal and the resultant multiplication X·Y=Z of the Total Value. This analog output is then transformed to a digital output by ADC.

The ratio value is standardly the A/G Ratio or the first fraction to the remaining fractions. The user has the option of changing this ratio to be the Total to any fraction or any fraction to any fraction via the keyboard. The sequencer will direct the required fraction values (amplitude or integral) to the RATIO 1 DAC and Ratio 2 DAC. Again the DAC's transform their digital input to analog equivalents which are applied to divider module X/Y=Z whose output is the analog ratio. This is transformed for output to a digital word by the RATIO ADC.

The remaining information required is the patient identification and the sequence number of the scan. This is output from the PATIENT ID and SEQ # shift register.

In the External standard mode the Total protein values of the sample are input by the user for each scan. In the internal standard modes the total protein values are inferred from a standard scan. In order to perform this a standard is processed first through the system and the data about that scan is held in the proper registers. Then, as succeeding scans are made, the information collected about the standard is used to compute the total protein values of each sample as it is processed. This is based on the presumption that since the dyes used adhere to the protein then the level of density implies the level of total protein.

To differentiate between modes the operator will depress the proper mode key on the keyboard. This will set up the sequencer for the internal standard 1, 2 or 3. The user will then enter the standards total protein values. Presumably the first scan is a standard. However, after that there is no requirement for another standard. To clarify, wherever the user enters a total value that scan will be processed as a standard and the succeeding scans as variables, until another standard is reached by virtue of its total protein entry being associated with a sequence number. Thus, the user may process one standard per 48 samples on multiple plates or they may opt to use one standard per plate. In the flow of events the user will also enter the patient identification for the samples to be run.

Once the user has entered the proper data the start command will be given at the keyboard. The unit will then scan the first standard. As the standard is processed its output will be derived as though it were under the external standard conditions described above. The total protein value will be in STD TOTALS shift register instead of EXT STD TOTALS. However, the sequencer will direct the total integrals from INT TOTAL to the STD T INT latch, the total amplitude from AMP TOTAL to STD T AMP latch, and then find the peak amplitude placing it in STD PEAK AMP. This peak amplitude is found by the sequencer in the same method the fraction peak amplitude was found earlier but with the beginning and ending addresses as delimiters in lieu of the fraction marks.

The sequencer will then direct the XY table (carriage) to the next scan. If the unit is now in internal standard 1 this next sample is one of the unknowns. The unit will scan, as before, sampling data, etc. However, when the unit is ready to output the total protein the standards total protein will be directed by the sequencer from the STD TOTALS shift registers to the STD TOTAL DAC. The comparator driving K1 will again be overridden by clearing STD 2 INT DAC. The sequencer will direct the standards total integrals or amplitudes, as required, from STD T INT or STD T AMP to the STD INT OR AMP DAC. These two DAC's have their output applied to a divider module X/Y = Z via K1A and B. The quotient provided by the divider is X units per integration. This is to be multiplied by the unknown samples total integral (via SAMPLE TOTAL DAC) at X·Y = Z. This will provide an analog output equivalent to that unknown samples total protein. This analog signal is transformed into a digital word for output by SCALED DIG TOT ADC. It also serves as the total during the fraction scaling, as before, for the SCALED FRACTION TOTAL PROTEIN. The rest of the sequence is then directed by the sequencer, as before, for the other outputs.

If the user had selected the third internal standard when setting the machine the values used at STD TOTAL DAC and STD INT OR AMP DAC would have been input directly. That is the numerical data would have been entered directly from the keyboard and latched at 3RD INT STD in lieu of values directly measured by the machine stored at STD T INT or STD T AMP. Then when the sequencer required this information it would use the entered values to determine the total protein units per integration ratio at the STD TOTAL DAC and STD INT OR AMP DAC. These values are used for all scans thereafter.

During the process for the Dual internal standard or internal standard 2 a test is made. To begin with the dual standard uses two standard scans. The first standard of the sequence should be the densest immediately followed by the diluted standard. These two standards have their total protein value entered by the user. The scans following the standards will be treated as variables until another pair of standards are encountered similar to the internal standard 1. As the standards are scanned data is collected about them and stored for future reference. As a succeeding unknown scan is made the two standards assigned total protein values are placed in STD TOTAL DAC for the first or densest and in STD 2 TOTAL DAC for the second. The total integral or amplitudes are directed to the STD INT OR AMP DAC for the first or densest and to STD 2 INT DAC for the second standard.

Now, as the variable scans total integrals or amplitudes are directed to the SAMPLE TOTAL DAC the test is made. If the SAMPLE TOTAL DAC is less than the STD 2 INT DAC the comparator driving K1 will select the second standard to scale to. This is by K1A selecting STD 2 INT DAC for the integrals or amplitudes of the second standard. Also by K1B selecting the second standard total protein value at STD 2 INT DAC. If, on the other hand, the sample total integrals or amplitudes were greater K1 would select the first standards values at STD TOTAL DAC and STD INT OR AMP DAC for the total protein values and total integrals or amplitudes, respectively.

This dual internal standard allows a deviation from a linear relationship of protein/dye adhesion and density profile. Thus, if a serum has a nonlinear region the dual standard allows a closer approximation of total protein value.

The OD STD enables the user to obtain the optical density values of each fraction in a scan. To bring this about the user enters via the keyboard the O.D. full scale value. This value is stored in ODFS LATCH.

As part of the set up routine the user instructs the machine to read a neutral density filter of known O.D. In this hardware approximation this filter should be of the full scale OD entered above. In the Cliniscan almost any value of filter may be used. However, this filter is read through the analog input by the INPUT ADC and directed by the sequencer to the OD STD DAC. The user then instructs the machine to read the zero or full light condition. This value is directed by the sequencer to the OD Z DAC. The difference between the two analog signals is taken for a machine input level for that full scale OD value. Then each fraction peak is divided by this level via the AMP DAC and the divider module. The resulting quotient is multiplied by the user assigned full scale OD value at OD FS DAC. The output is transformed to a digital word by the ADC. This is done for each fraction, as stated above, with output values at OPTICAL DENSITY VALUES.

Figure 40:
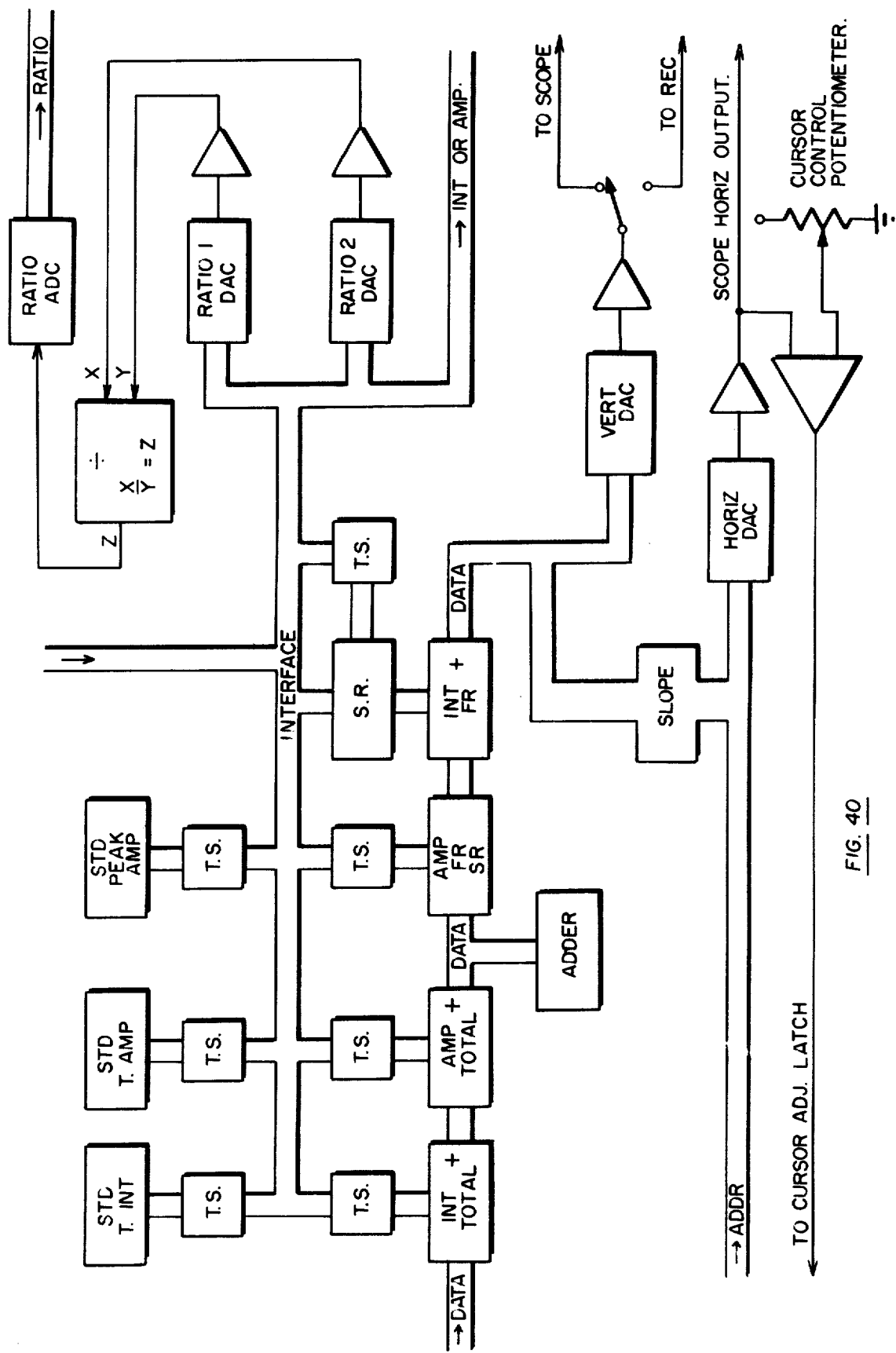
Figure 41:
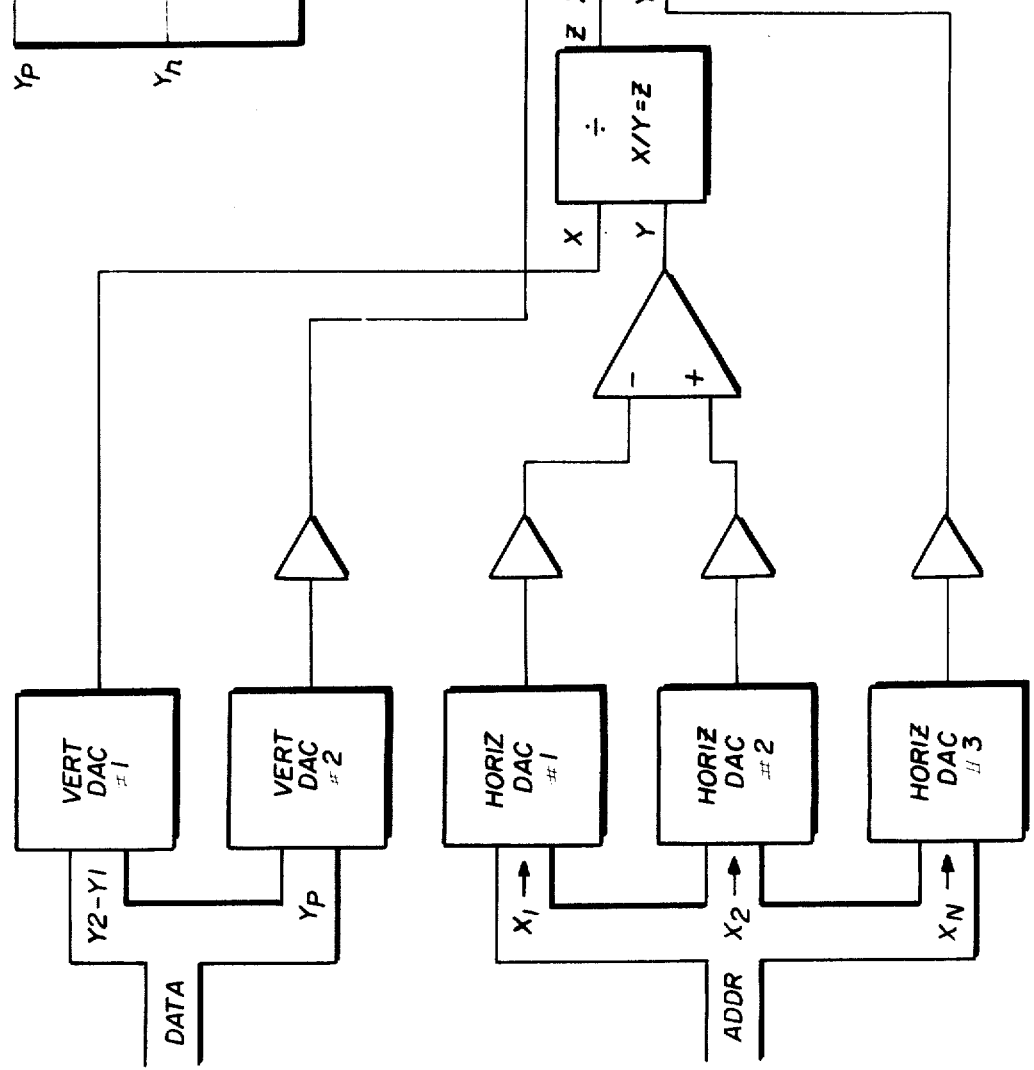

The slope function is brought about by the user depressing the slope key. The hardware for the slope function is shown in FIG. 40 and the computational circuitry therefore in FIG. 41. The data bus is brought to two vertical DAC's (1 and 2) with the address bus brought to three DAC's (1, 2 and 3). The DAC's drive the computational circuits with the end result digitized by the ADC.

The slope function is used to correct for a baseline offset that is brought about from a density gradient on the sample carrier or plate. If the density gradient is a linear change the offset area can be calculated from the two point formula for the line connecting the first fraction mark and the last fraction mark. Referring to the graph of FIG. 42, this area is shown as the area below the line $(X_1, Y_1)$ to $(X_2, Y_2)$. Therefore, any point along the line can be calculated if one of the values is known. (i.e., $X_n$).

The addresses of the data will serve as the X axis or the known values. Therefore, one may calculate the Y value and subtract it from the scan data at that X address to shift the scanned waveform down to the baseline at the X axis. If $Y_{ps}$ is the data point amplitude after the slope routine and $Y_p$ before the slope routine $Y_{ps}$ may be found from $Y_{ps}=Y_p-Y_n\,(Y_2-Y_1)/(X_2X_1)$ where $(X_n, Y_n)$ are derived from the address (X) and baseline error (Y).

To perform the calculations $Y_2-Y_1$ is performed by 9's COMPLEMENT and ADDER and sent to VERT DAC 1. The data point is sent to VERT DAC 2. The addresses $X_1$, $X_2$ and $X_n$ are sent to H DAC's 1, 2 and 3, respectively. The subtraction of $X_1$ from $X_2$ is provided by a op amp following the DAC buffers. This is applied to the divisor input (Y) of a divider module. The dividend is from VERT DAC 1 or $Y_2-Y_1$. The quotient output (Z) is applied to a multiplier input (X) providing $(Y_2-Y_1)/(X_2-X_1)$. This is multiplied by $X_n$ at the Y input of the multiplier via H DAC 3. The product output (Z) is the $X_n(X_2-Y_1)/(X_2-X_1)$. This is substracted at the op amp from $Y_p$ via VERT DAC 2 and the output transformed to a digital word by ADC. This is then directed to the RAM to replace the current data point.

The quence (QNCH) function is brought about by the user depressing the proper key at the keyboard. The sequencer then routes all data to the 9's COMPLEMENT (QNCH) register. This performs a conventional math inversion. Then the fractions and peaks are reselected by the sequencer switching the two shift registers contents (FR ADDR and PEAK ADDR).

It will be understood that many specific operations executed by the microprocessor under program control have not been discussed in detail and many procedures such as various test routines and the like have not been described since they are not necessary for an understanding of the present invention. The above description of the circuitry and the operation of the microprocessor-controlled densitometer system of the present invention teaches a vastly improved system over those of the prior art; greatly automates a large portion of the operations previously done manually; performs the operations with greater speed and accuracy; allows a wider variety of internal and external standards to be used and a wide variety of recorder formats depending upon the user's needs.

The microprocessor-controlled densitometer system of the present invention requires only a single one-time scan of the sample to be analyzed and enables the pattern to be displayed, over and over again, on an oscilloscope and modified, if desired, until the user is totally satisfied as to the shape, fraction boundaries, and other information to be recorded on a permanent medium. The system of the present invention also enables a batch of samples to be handled one at a time or by groups with each sample within a group being scanned and processed automatically, if desired.

With this detailed description of the specific apparatus, the program and an alternate hardware embodiment of the program used to explain the preferred embodiment of the present invention and the operation thereof, it will be obvious to those skilled in the art that various modifications can be made in both the method and apparatus of the present invention without departing from the spirit and scope of the invention which is limited only by the appended claims.

We claim:

1. A method of graphically displaying optical density patterns of a sample of blood or the like for subsequent evaluation comprising the steps of:

optically scanning a sample a single time to generate a time-varying analog waveform which is a function of the optical density of the scanned sample;

converting the generated analog waveform into a set of digital signals;

storing the set of digital signals in memory as raw sample data;

retrieving said stored raw sample data to reproduce said time-varying analog waveform and displaying a normalized version of said analog waveform on a CRT device for visual operator inspection without rescanning said sample;

editing the visually displayed normalized analog waveform to selectively modify portions thereof; and recording a graphical trace of said edited normalized analog waveform on a fixed medium for subsequent evaluation.

2. The method of claim 1 wherein said step of optically scanning a sample is preceded by the step of entering the total actual value of protein in said sample and said editing step is followed by the step of scaling said edited normalized analog waveform to said total actual value of protein in said sample prior to recording a scaled graphical trace thereof.

3. The method of claim 1 further including the steps of detecting the location of fraction boundaries which correspond to the negative peak values of said time-varying analog waveform, storing the values thereof in memory; retrieving said stored values for indicating the fraction boundaries on said CRT displayed normalized version of said analog waveform and wherein said step of editing the visually displayed analog waveform further includes the steps of manually selecting those fraction boundary values which are to be added, deleted, modified or the like.

4. The method of claim 3 wherein said step of editing further includes the steps of generating a cursor signal; manually positioning said cursor signal relative to said CRT displayed analog waveform; terminating cursor positioning whenever said cursor is positioned proximate a fraction boundary value to be modified; modifying the selected fraction boundary value by deleting the preselected value, adding a new value, or the like; storing the modified fraction boundary value in memory; and continuing to manually position the cursor signal relative to the CRT displayed analog waveform until the operator is satisfied with said CRT displayed waveform.

5. The method of claim 4 further including the steps of integrating the total area under the analog waveform and storing a first value indicative of the total integral in memory, selecting a particular portion of said analog waveform defined by the stored values of said fraction boundaries, integrating the area under the analog waveform of said selected portion and storing a second value indicative of the area of the selected fraction in memory, comparing the stored second value indicative of the selected fraction with the stored first value indicative of the total integral, computing a third value representative of said comparison and storing said third value in memory and wherein said recording step includes printing the digital value of said third stored value proximate said selected portion of said recorded graphical trace.

6. A method of graphically recording an analog profile trace indicative of variations in the optical density of a blood sample or the like on a fixed medium comprising the steps of:

(a) optically scanning a sample;

(b) generating an electrical analog waveform indicative of variations in the optical density of the scanned sample;

(c) converting said electrical analog waveform into digital data representing the original scanned sample values;

(d) storing said digital data representing the original scanned sample values in memory;

(e) retrieving said digital data while simultaneously maintaining said digital data unchanged in memory until the next actual scan occurs in case the original scanned sample values need to be reconstructed;

(f) normalizing the retrieved digital data such that the maximum peak value is as close to full scale as possible;

(g) reconverting the normalized digital data to display a normalized optical density analog waveform pattern on a CRT-type display for operator viewing without rescanning the original sample;

(h) editing the displayed normalized optical density analog waveform pattern by selectively altering portions thereof, as required; and (i) recording an analog profile trace representative of the edited normalized optical density analog waveform pattern on a fixed medium for subsequent evaluation.

7. The method of claim 6 further including the steps of detecting peaks in the generated electrical analog waveform and storing the maximum value thereof and wherein said normalizing step includes computing a multiplier value which, when applied to said stored maximum peak value, will cause said maximum peak value to be as close to full scale as possible and multiplying all of the original scan sample values by said computer multiplier value for normalizing same.

8. The method of claim 6 further including the step of detecting low points in said generated electrical analog waveform and storing the values thereof to automatically define fraction boundaries and wherein said step of editing the normalized optical density analog wave form pattern includes the step of selectively modifying said waveform pattern by deleting, adding, or otherwise changing the locations of said fraction boundaries and storing the edited fraction boundary values for future calculations.

9. The method of claim 8 wherein said step of editing includes:

(a) generating a CRT cursor signal;

(b) manually positioning said cursor signal along said CRT displayed optical density analog waveform pattern for locating positions therealong;

(c) stopping the cursor positioning at selected locations along said analog waveform pattern for addressing said locations;

(d) entering keyboard commands for controlling the addition, deletion or modification of fraction boundaries at said addressed locations;

(e) storing the new values of the modified fraction boundary locations in memory and continuing to position said cursor signal until the operator is satisfied with the CRT displayed normalized optical density analog waveform pattern and the fractional boundaries defined thereon.

10. The method of claim 9 further including the steps of integrating the total area under the displayed optical density analog waveform pattern and storing a first value indicative of said total area, integrating a selected portion of said normalized optical density analog waveform pattern between selected fractional boundaries and storing a second value indicative of said selected fractional area, comparing said first value with said second value, computing a third value representative of said comparison, and printing said third value in digital form on said fixed medium in proximity to a corresponding portion of said recorded analog profile trace.

11. The method of claim 6 further including the steps of initially entering the total value of protein contained in the sample to be scanned and then scaling the values of said normalized optical density analog waveform pattern to said actual total protein value and then recording a properly scaled analog profile trace on said fixed medium for subsequent evaluation.

12. A method of measuring optical density-related information on a blood sample or the like and recording a permanent record of at least one optical density relationship for subsequent evaluation purposes comprising the steps of:

entering an internal standard sample whose total protein value is known into memory;

optically scanning an unknown sample to generate an electrical analog waveform which is a function of the optical density of said scanned sample;

converting said electrical analog waveform into a series of digital signals and storing said digital signals in memory as raw sample data;

retrieving said raw sample data to reconstruct and visually display said analog waveform for operator inspection without rescanning said unknown sample and while simultaneously maintaining said stored raw sample data unchanged in memory;

editing said displayed analog waveform to modify, add or delete fraction boundaries or the like;

scaling the values of said edited analog waveform to the total protein value of said stored internal standard sample; and recording a graphical plot of at least one selected fraction of said scaled analog waveform for subsequent evaluation.

13. A method of measuring optical density-related information on a blood sample or the like and recording a permanent record of at least one optical density relationship for subsequent evaluation purposes comprising the steps of:

entering a first internal standard sample whose total protein value is known as a first digital value in a first memory location;

entering a second internal standard sample whose total protein value is known as a second digital value in a second memory location;

optically scanning an unknown sample to generate an electrical analog waveform which is a function of the optical density of said scanned sample;

converting said electrical analog waveform into a series of digital signals and storing said digital signals in memory as raw sample data;

retrieving said raw sample data to reconstruct and visually display said analog waveform for operator inspection without rescanning said unknown sample and while simultaneously maintaining said stored raw sample data in memory;

editing said displayed analog waveform to modify, add, or delete fractional boundaries or the like;

computing the total value of the edited analog waveform and storing the total value thereof as a third total value in memory;

comparing the third stored total value to the first stored total value;

identifying said first stored total value as a scaling modifier if said third stored total value is less than or equal to said first stored total value;

identifying said second stored total value as said scaling modifier if said third stored total value is greater than first stored total value;

scaling the values of said edited analog waveform with said identified scaling modifier; and recording a graphical plot of at least a selected fraction of said scaled analog waveform for subsequent evaluation.

14. A method of measuring optical density-related information on a blood sample or the like and recording a permanent record of at least one optical density relationship for subsequent evaluation purposes comprising the steps of:

scanning a standard sample of known optical density;

storing the known optical density value of said scanned standard sample for future scaling purposes;

optically scanning an unknown sample to generate an electrical analog waveform which is a function of the optical density thereof;

converting said electrical analog waveform into a series of digital signals and storing said digital signals in memory as raw sample data;

retrieving said raw sample data to reconstruct and visually display said analog waveform for operator inspection without rescanning said unknown sample and while simultaneously maintaining said stored raw sample data in memory unchanged;

editing said displayed analog waveform to selectively add, delete, or otherwise modify fraction boundaries or the like;

selecting a desired one of relative and absolute optical densities;

scaling the edited analog waveform to said stored value of said standard optical density sample such that the amplitude of the scanned analog waveform represents said selected relative and absolute optical density measurements; and recording a graphical plot of said selected fraction of said analog waveform scaled to said selected one of relative and absolute optical densities on a permanent medium for subsequent evaluation or the like.

15. A method for graphically recording optical density functions of a scanned blood sample or the like comprising the steps of:

optically scanning and unknown sample and generating an electrical analog signal which is a function of the optical density of said scanned sample;

converting said generated electrical analog signal into digital data representative thereof and storing said digital data in memory as original raw sample data;

detecting the amplitude peaks of said generated electrical analog signal and storing the value of the maximum peak as a first modifier value;

detecting low points in said generated electrical analog signal and storing the values thereof to subsequently define fraction boundaries in the waveform pattern of said electrical analog signal;

retrieving the stored digital data representing said electrical analog signal, said stored modifier value, and said values defining fraction boundaries to reconstruct a normalized analog waveform pattern representing said signal wherein the maximum amplitude peak comes as close to full scale as possible and wherein said stored values representing low points are used to define fraction boundaries therein;

visually displaying said reconstructed normalized analog waveform pattern on a CRT-type display for operator inspection without rescanning said original sample and without disturbing the values of the raw sample data stored in memory;

editing the CRT-displayed analog waveform pattern to selectively modify fraction boundary decisions and the like; and recording the normalized waveform pattern as an analog profile trace on a fixed medium for subsequent evaluation.

16. The method of claim 15 further comprising the steps of selecting a portion of the displayed analog waveform pattern between selected fraction boundaries for which desired information is required;

integrating the selected portion of the analog waveform pattern between said selected boundary values and storing the integration value in memory;

integrating the entire displayed analog waveform pattern and storing a total integral value in memory;

comparing the stored integral value of said selected portion to said stored total integral value;

computing a third value representative of said comparison; and printing said computed third value on said fixed medium in proximity to a corresponding portion of said recorded analog profile trace.

17. The method of claim 16 further including the steps of initially entering the actual protein value of the sample into a keyboard, transferring the keyboard-entered value of total protein into a storage location in memory and scaling said edited analog waveform pattern and said computed value so that a scaled analog profile trace is recorded on said medium and a scaled computed third value is printed on said medium for evaluation purposes.

18. The method of claim 15 further including the steps of initially scanning a standard sample of known total protein and storing the value thereof in memory and subsequently scaling said edited analog waveform pattern to said stored standard value prior to recording the scaled analog profile trace.

19. The method of claim 15 wherein said step of recording the normalized waveform as an analog profile trace on a fixed medium includes graphing an analog profile trace of at least a selected fraction of said analog waveform pattern and printing values of digital information relating thereto on said fixed medium proximate said graphed analog profile trace.

20. A densitometer for graphically recording the relevant optical density patterns of a blood sample or the like comprising:

means for optically scanning a sample and generating an electrical analog waveform pattern which is a function of the optical density of said scanned sample;

means for converting said generated electrical analog waveform pattern into digital sample data;

memory means for storing said digital sample data;

means for retrieving said stored digital sample data and reconstructing a normalized version of said analog waveform pattern without rescanning said sample or affecting the stored values of said digital sample data;

CRT means for displaying said reconstructed analog waveform pattern for visual inspection by an operator;

editing means for selectively modifying portions of said analog waveform pattern to alter fraction boundary decisions and the like; and means for graphically recording at least a selected portion of said edited optical density waveform pattern.

21. The densitometer of claim 20 wherein said means for generating said electrical analog waveform pattern includes a photomultiplier tube for transforming light from said sample into an electrical analog signal which is a function of the optical density of said sample;

- input amplifier means for receiving and amplifying said electrical analog signal generated by said photomultiplier tube, said input amplifier means including first and second feedback paths, said first feedback path including means for operating said amplifier in a linear mode and said second feedback path including means for operating said linear amplifier in a logarithmic mode;
- means for selecting one of said first and second feedback paths for selecting the desired mode of amplifier operation;
- a gain control amplifier for receiving the output of said input amplifier and controlling the gain as well as the offset of the amplifier chain;
- low pass filter means at the output of said control amplifier;
- sample and hold means for receiving said amplified and filtered electrical analog signal and maintaining the level thereof for a predetermined time interval;
- a memory for storing digital information; and
- microprocessor means for controlling the rate of sampling the signal maintained at said sample and hold means and for converting a sampled analog signal into digital values indicative thereof and storing same in said memory so that at the end of one complete scan of said sample, digital information representative of the generated electrical analog waveform representing a function of the optical density of said scanned sample is stored as raw sample data in said memory and maintained therein in an unchanged state until the next different sample is scanned.

22. The densitometer of claim 20 wherein said means for retrieving said stored digital sample data and reconstructing a normalized version of said analog waveform pattern without rescanning said sample includes microprocessor means, means for initially detecting the peak values of said electrical analog waveform and storing the maximum peak value in a memory location, said microprocessor retrieving said maximum peak value from said memory location and multiplying said maximum peak value by a computed modifier value sufficient to increase said maximum peak value as close as possible to a full scale reading, said microprocessor then multiplying all sampled portions of said electrical analog waveform pattern by said modifier value for normalizing said analog waveform pattern, and control circuitry responsive to command signals from said microprocessor for driving said CRT means for displaying said reconstructed analog waveform pattern for operator viewing.

23. The densitometer of claim 20 wherein said editing means includes means for generating a cursor signal on said CRT display means; circuit means to enable the manual positioning of said cursor signal along said normalized analog waveform pattern for addressing a specific waveform pattern location when said cursor signal is stopped; keyboard means for at least one of selectively adding and deleting fraction integral boundary marks, automatically clearing all preselected fraction boundary marks, controlling the starting and ending points of a scan, removing predetermined areas of a scan from computations, adjusting sensitivity, and commanding that the displayed and edited waveform pattern be recorded on said fixed medium.

24. The densitometer of claim 20 wherein said means for graphically recording said edited and normalized optical density waveform pattern further includes printing means for printing alphanumeric information proximate said waveform graph to supply required relative, scaled, absolute or percentage information related thereto.

25. A microprocessor-based densitometer for measuring and recording information relating to the optical density of a sample which is scanned only once, said densitometer comprising:

- means for optically scanning a sample and generating an electrical analog waveform which is a function of the optical density of said scanned sample;
- means for converting said generated electrical analog waveform into digital sample data;
- memory means for storing said digital sample data until the next subsequent sample is scanned;
- means for detecting the peak values of the optical density waveform and storing the maximum peak value in said memory means;
- means for detecting the value of the valleys of said optical density waveform and storing said values in said memory means as an indication of the boundaries between successive fractions of said optical density waveform;
- microprocessor means including means for multiplying the peak value of said optical density waveform stored in said memory means with a computer multiplier value sufficient to bring said peak value as close as possible to a full scale reading;
- microprocessor-controlled means for retrieving said digital sample data from said memory means;
- microprocessor-controlled means for multiplying the values of said digital sample data by said computer modifier value to reconstruct a normalized optical density waveform;
- CRT display means for visually displaying said reconstructed normalized optical density waveform as a curve on the CRT display for operator inspection, said microprocessor retrieving said stored fraction boundary values and inserting same into said normalized optical density waveform for visually displaying said fraction boundaries on said CRT displayed curve;
- manually operable means for editing said curve and selectively modifying portions thereof by adding, deleting or otherwise modifying said boundary values or the like;
- means for detecting the manually selected added, deleted, or modified fraction boundary values and storing the new values thereof in said memory means under the control of said microprocessor means;
- means for manually selecting a portion of said optical density curve for which information is required;
- integrating the total area under said curve and storing a total area value in said memory means;
- integrating the area under said selected portion of said curve and storing a selected area value in said memory means;
- said microprocessor means comparing said total integral area value with said selected portion integral area value and computing a numerical value representative of said comparison;
- recording at least the selected portion of said optical density curve as an analog profile trace on a fixed medium; and printing said computed numerical value on said fixed medium in proximity to said recorded profile trace for evaluation purposes.

26. The densitometer of claim 25 further including means for entering a standard total value into said memory means, said microprocessor means subsequently utilizing said stored standard total value for scaling said analog profile trace and said computed numerical value thereto.

27. In an apparatus for graphically displaying optical density patterns of a scanned sample of blood or the like, including means for optically scanning said sample and generating an electrical analog signal as a function of the optical density of said scanned sample, CRT display means for visually displaying a normalized waveform version of said electrical analog signal, means for editing said displayed waveform and graphical display means for recording at least a selected portion of the said edited analog waveform as an analog profile trace on a fixed medium, the improvement comprising:

analog-to-digital conversion means for converting said electrical analog signal into digital data representing said optical density waveform pattern;

memory means for storing said digital data until the next subsequent sample is optically scanned;

microprocessor means for retrieving said digital data from said memory means and reconstructing said optical density waveform pattern without a second scan of said sample and without disturbing the digital data in said memory means, said microprocessor generating commands for controlling said CRT to visually display said reconstructed and normalized optical density waveform pattern for operator inspection and editing, said microprocessor means further controlling scaling calculations, ratio and percentage calculations, the integration of the area under the optical density waveform pattern, and the printing of alphanumeric information on said fixed record medium in relation to said recorded analog profile trace for ease of evaluation and the like.

28. In a densitometer comprising means for optically scanning a sample of blood or the like and generating an electrical analog signal waveform which is a function of the optical density of said scanned sample and means for graphically recording at least one selected function of said optical density waveform as an analog profile trace on a fixed medium and printer means for printing alphanumeric information relating to said recorded profile trace on said fixed medium and in proximate relation to said recorded profile trace to facilitate subsequent evaluation, the improvement comprising A/D converter means for converting said electrical analog signal into digital data representing said electrical analog signal waveform, memory means for storing said digital data, microprocessor control means, CRT display means for visually displaying a reconstructed version of the original electrical analog waveform under the control of said microprocessor means to enable an operator to visually inspect the reconstructed analog waveform, editing means for selectively modifying the displayed analog waveform, said editing means including means for generating a cursor signal, manually operable means for positioning said cursor signal along said optical density analog waveform for addressing particular positions thereon, keyboard entry means for selectively modifying any portion of said displayed optical density analog waveform addressed by said manually positionable cursor signal and means for graphically recording at least one selected function of said edited optical density analog waveform and printing numerical data relevant thereto for evaluation purposes.

29. A microprocessor-based densitometer system comprising:

microprocessor means;

memory means;

program means stored in said memory means for execution by said microprocessor means to perform mathematical computations, control functions and the like;

optical scanning means for optically scanning a sample of blood to be analyzed and generating an analog waveform signal related to the optical density of said scanned sample;

means for converting said analog waveform signal into digital data indicative thereof and storing said digital data in said memory means;

means for retrieving said digital data from said memory means and reconstructing said analog waveform signal without the need for rescanning said sample;

CRT means for visually displaying said reconstructed analog waveform signal as a CRT trace indicative of the optical density waveform pattern represented by said analog waveform signal for operator inspection;

means for generating fraction boundary markers corresponding to the negative peaks along said optical density waveform pattern to identify the boundaries between sample fractions;

means for editing said displayed optical density waveform pattern for selectively deleting, adding and changing the location of said fraction boundary marks, as desired;

means for generating a Draw command whenever the operator is satisfied with the edited CRT trace and the edited fraction boundaries of said optical density waveform pattern represented by said CRT trace;

means responsive to said Draw command for retrieving and reconstructing a normalized and properly scaled version of said optical density waveform pattern and generating an analog output indicative thereof;

recorder means responsive to said analog output for graphically recording said optical density waveform pattern as a graphical trace on a fixed record media with said edited fraction boundary marks properly positioned thereon for subsequent evaluation purposes.

30. A densitometer system comprising:

memory means;

program means stored in said memory means;

microprocessor means for executing said program means to control the operation of said densitometer system;

optical scanning means for scanning a sample to be analyzed and generating an analog signal which is a function of the optical density of said scanned sample;

means responsive to said microprocessor means for converting said analog signal into digital data indicative of the optical density waveform pattern represented thereby and storing said digital data in said memory means;

peak detector means for monitoring the amplitude of said analog signal;

means responsive to said microprocessor means for converting the maximum value of said analog signal detected by said peak detector means into digital data and storing same in said memory means, said microprocessor means executing said program means to normalize said optical density waveform pattern using said stored maximum value;

slope monitoring means for detecting the position of valleys in said analog signal and generating negative peak signals indicative of the boundary position between fractions;

means responsive to said microprocessor means for converting said signals indicative of the position of said valleys into digital data representing the location of said fraction boundaries and storing same in said memory means;

means responsive to said microprocessor means for retrieving said digital data from said memory means and reconstructing a normalized analog signal indicative of said normalized optical density waveform pattern;

CRT means responsive to said normalized analog signal for displaying a CRT trace indicative of said optical density waveform pattern and including fraction boundary marks indicating the position of said fraction boundaries along said CRT trace for operator inspection;

means for generating a cursor signal;

means for selectively positioning said cursor signal along said displayed CRT trace to address any given position thereon;

keyboard means for entering operator commands to edit said optical density waveform pattern trace by selectively deleting, adding, or modifying the position of said fraction boundaries, said keyboard means including manually operable means for generating a Draw command whenever the operator is satisfied with said displayed and edited CRT trace and the position of said fraction boundary markers on said optical density waveform pattern;

recorder means responsive to said microprocessor means for graphically recording said edited optical density waveform pattern including said fraction boundary marks as a graphical trace on a permanent record medium for subsequent evaluation;

means for integrating the area under the optical density waveform pattern and the area under specific fractions thereof and storing values indicative of said integrated areas as digital data in said memory means;

means for entering scaling values, said microprocessor means performing numerical computations to generate desired numerical data relating to said stored integrated values and scaled versions thereof; and printing means responsive to said microprocessor means for printing said desired computed numerical data on said permanent record medium adjacent said optical density waveform pattern trace to aid in the subsequent evaluation thereof.

* * * * *